United States Patent
Yudin et al.

(10) Patent No.: US 9,260,479 B2
(45) Date of Patent: Feb. 16, 2016

(54) CYCLIC AMINO ACID MOLECULES AND METHODS OF PREPARING THE SAME

(75) Inventors: Andrei Yudin, Oakville (CA); Ryan Hili, Summerville, MA (US)

(73) Assignee: The Governing Council of the University of Toronto, Toronto (CA)

( * ) Notice: Subject to any disclaimer, the term of this patent is extended or adjusted under 35 U.S.C. 154(b) by 845 days.

(21) Appl. No.: 13/257,159

(22) PCT Filed: Mar. 16, 2010

(86) PCT No.: PCT/CA2010/000408
§ 371 (c)(1),
(2), (4) Date: Nov. 21, 2011

(87) PCT Pub. No.: WO2010/105363
PCT Pub. Date: Sep. 23, 2010

(65) Prior Publication Data
US 2012/0065366 A1      Mar. 15, 2012

Related U.S. Application Data

(60) Provisional application No. 61/160,571, filed on Mar. 16, 2009.

(51) Int. Cl.
| | |
|---|---|
| *C07K 5/12* | (2006.01) |
| *C07K 7/00* | (2006.01) |
| *C07K 1/02* | (2006.01) |
| *C07D 487/04* | (2006.01) |
| *C07D 487/14* | (2006.01) |
| *C07K 7/64* | (2006.01) |

(52) U.S. Cl.
CPC .............. *C07K 5/12* (2013.01); *C07D 487/04* (2013.01); *C07D 487/14* (2013.01); *C07K 5/123* (2013.01); *C07K 5/126* (2013.01); *C07K 7/64* (2013.01)

(58) Field of Classification Search
CPC .............. C07K 5/12; C07K 7/00; C07K 1/02
USPC .................................. 530/317, 333, 338, 339
IPC .................... C07D 203/00, 203/08; C07K 7/50, C07K 7/52, 1/02, 1/08
See application file for complete search history.

(56) References Cited

U.S. PATENT DOCUMENTS

| | | | | |
|---|---|---|---|---|
| 5,693,325 | A * | 12/1997 | Kahn ........................... | 424/188.1 |
| 5,693,612 | A * | 12/1997 | Jonczyk et al. .............. | 514/21.1 |
| 5,693,750 | A * | 12/1997 | Ohki et al. ................... | 530/317 |
| 5,696,084 | A * | 12/1997 | Lartey et al. ................. | 514/3.6 |
| 5,705,481 | A * | 1/1998 | Jonczyk et al. ............... | 514/1.9 |
| 5,731,286 | A * | 3/1998 | Harbeson et al. ............ | 514/18.1 |
| 2008/0200398 | A1 * | 8/2008 | Smyth et al. ................. | 514/18 |

FOREIGN PATENT DOCUMENTS

| | | |
|---|---|---|
| WO | 0110799 | 2/2001 |
| WO | 2008046232 | 4/2008 |

OTHER PUBLICATIONS

Hili, R. et al., "Macrocyclization of linear peptides enabled by amphoteric molecules", J. Am. Chem. Soc., 2010, 132:2889-2891.
Vercilio, O.E. et al., "Design and synthesis of cyclic RGD pentapeptoids by consecutive Ugi reactions", Org. Lett., 2007, 10:205-208.
Baktharaman, S. et al., "Amino carbonyl compounds in organic synthesis", Aldrichimica Acta, 2008, 41:109-117.
Yudin, A.K. et al., "Overcoming the demons of protecting groups with amphoteric molecules", Chemistry. Eur. J., 2007, 13:6539-6542.
Hili, R. and Yudin, A.K., "Readily available unprotected amino aldehydes", J. Am. Chem. Soc., 2006, 128:14772-14773.
Achmatowicz and Jurczak, The synthesis of L-proline derived hexaazamacrocyclic ligands of C3 symmetry via intramolecular methyl ester aminolysis, Tetrahedron: Asymmetry 12 (2001) 487-495.
Burden et al., Synthesis and biological activities of YkFA analogues: effects of position 4 substitutions and altered ring size on in vitro opioid activity, Bioorganic & Medicinal Chem. Lett. 12 (2002) 213-216.
Hirose et al., Total synthesis and determination of the absolute configuration of guadinomines B and C2, Chem. Eur. J. 2008 14:8220-8238.
Murray et al., The synthesis of cyclic tetrapeptoid analogues of the antiprotozoal natural product apicidin, Bioorganic & Medicinal Chem. Lett. 22 (2001) 773-776.
Pil et al., Synthesis and electrophysiological characterization of cyclic morphiceptin analogues, Biochem. Pharma. 67 (2004) 1887-1895.
Quartara et al., Influence of lipophilicity on the biological activity of cyclic pseudopeptide NK-2 receptor antagonists, J. Med. Chem. 1994 37:3630-3638.

* cited by examiner

*Primary Examiner* — David Lukton
(74) *Attorney, Agent, or Firm* — Pepper Hamilton LLP

(57) ABSTRACT

Macrocyclization of amino acids or linear peptides upon reaction with amphoteric amino aldehydes and isocyanides is provided.

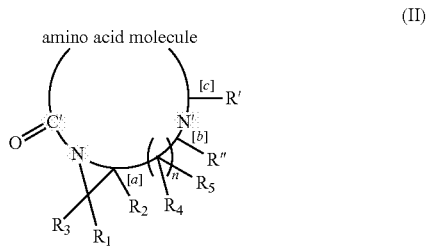

47 Claims, 33 Drawing Sheets

Crude reaction from D-Leu
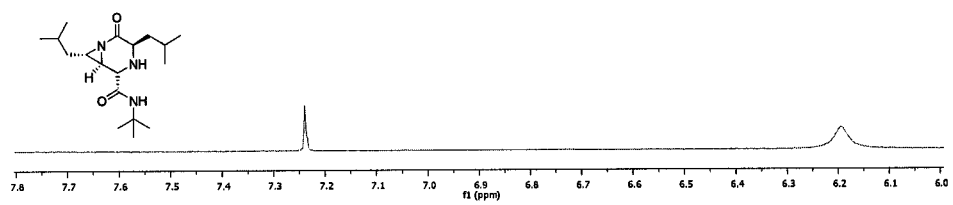
Crude reaction from L-Leu
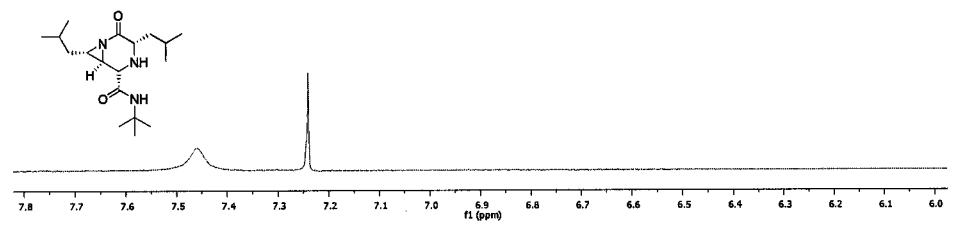
Mixture of isomers
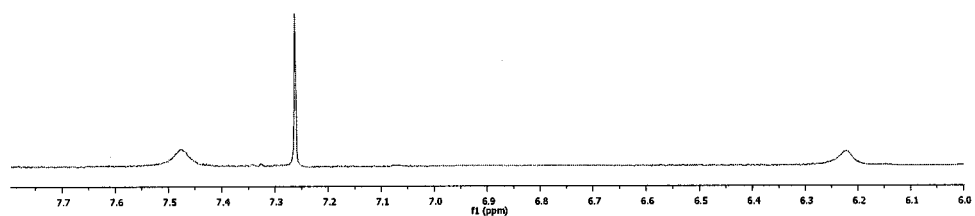
Figure 1. $^1$H NMR comparison of crude reactions mixtures using isomers of leucine.

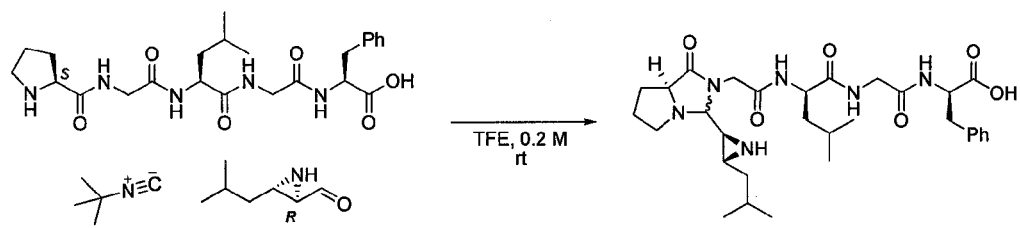
Figure 2. Mismatched reaction leads only to aminal products.

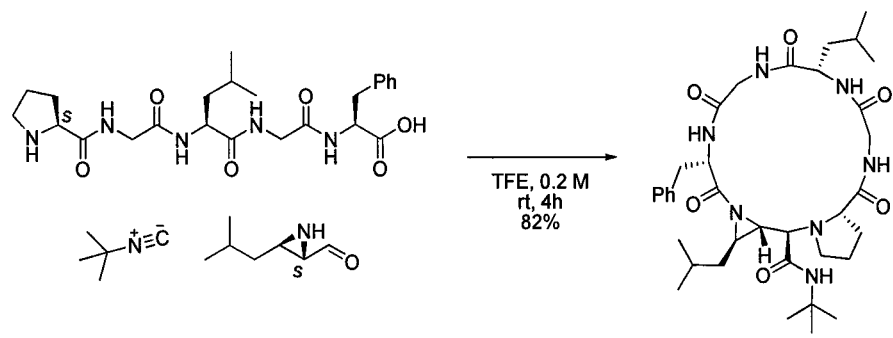
Figure 3. Matched reaction is fast and high yielding

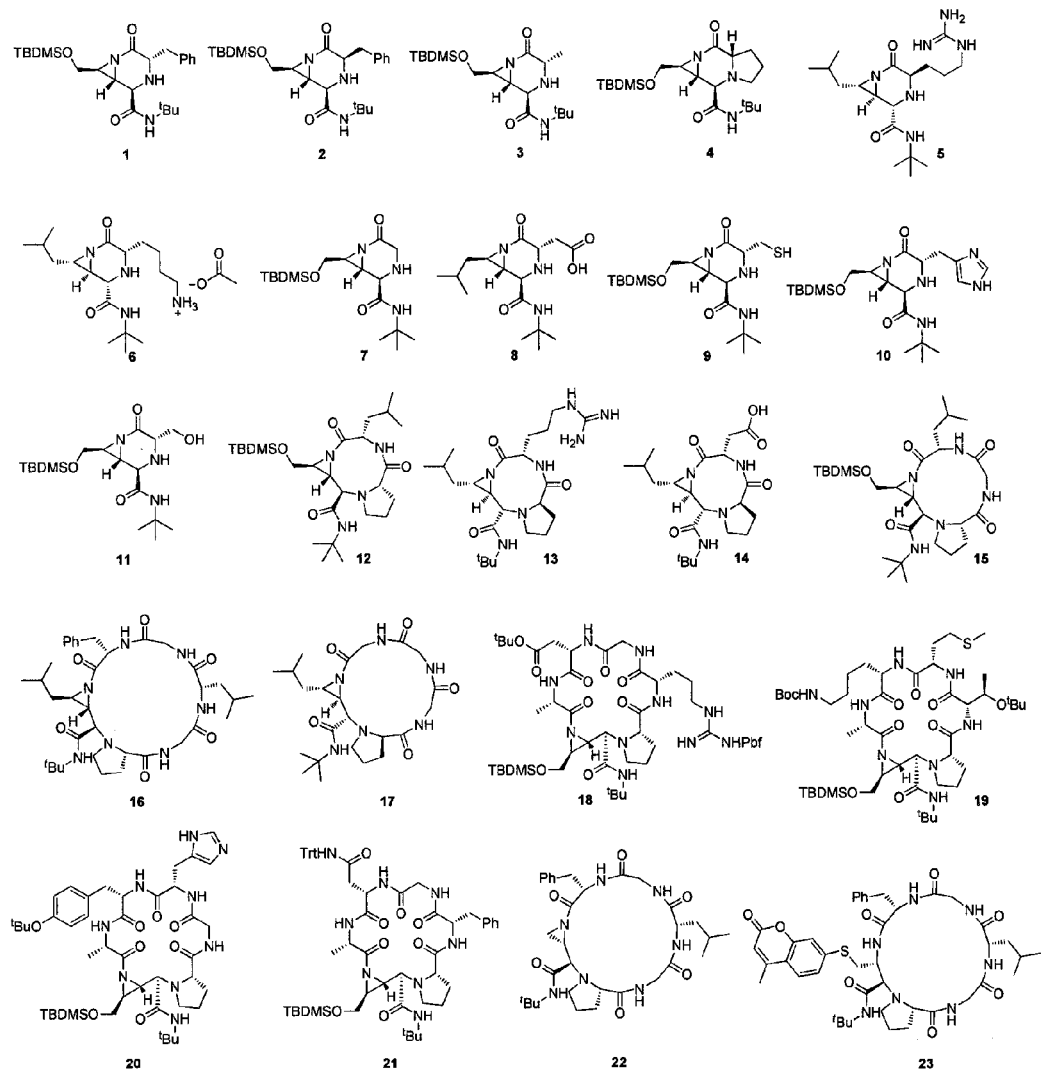
Figure 4. Chemical structures of cyclic products synthesized by Methods 1 – 3.

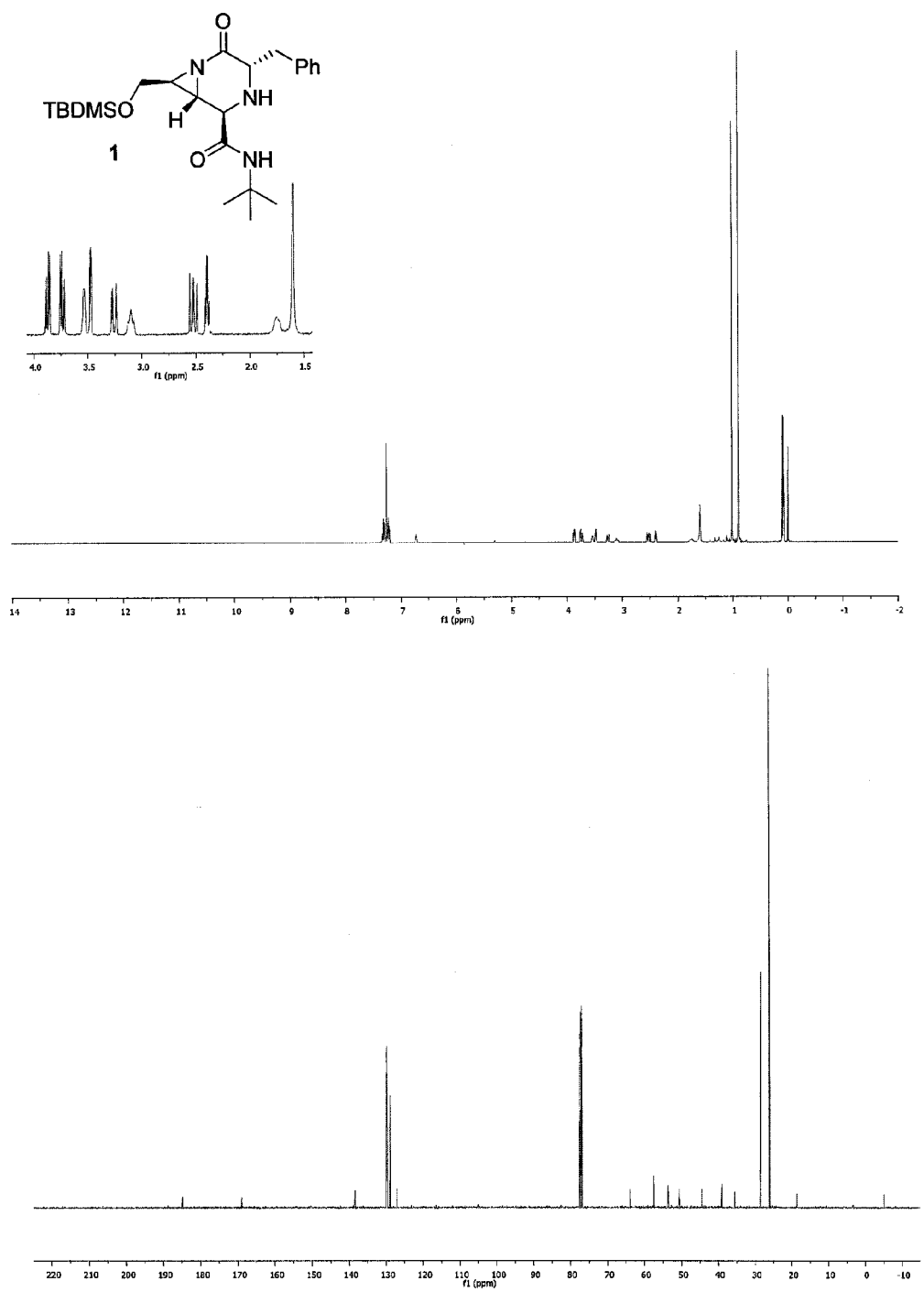
Figure 5. $^1$H and $^{13}$C NMR spectra for cyclic product 1.

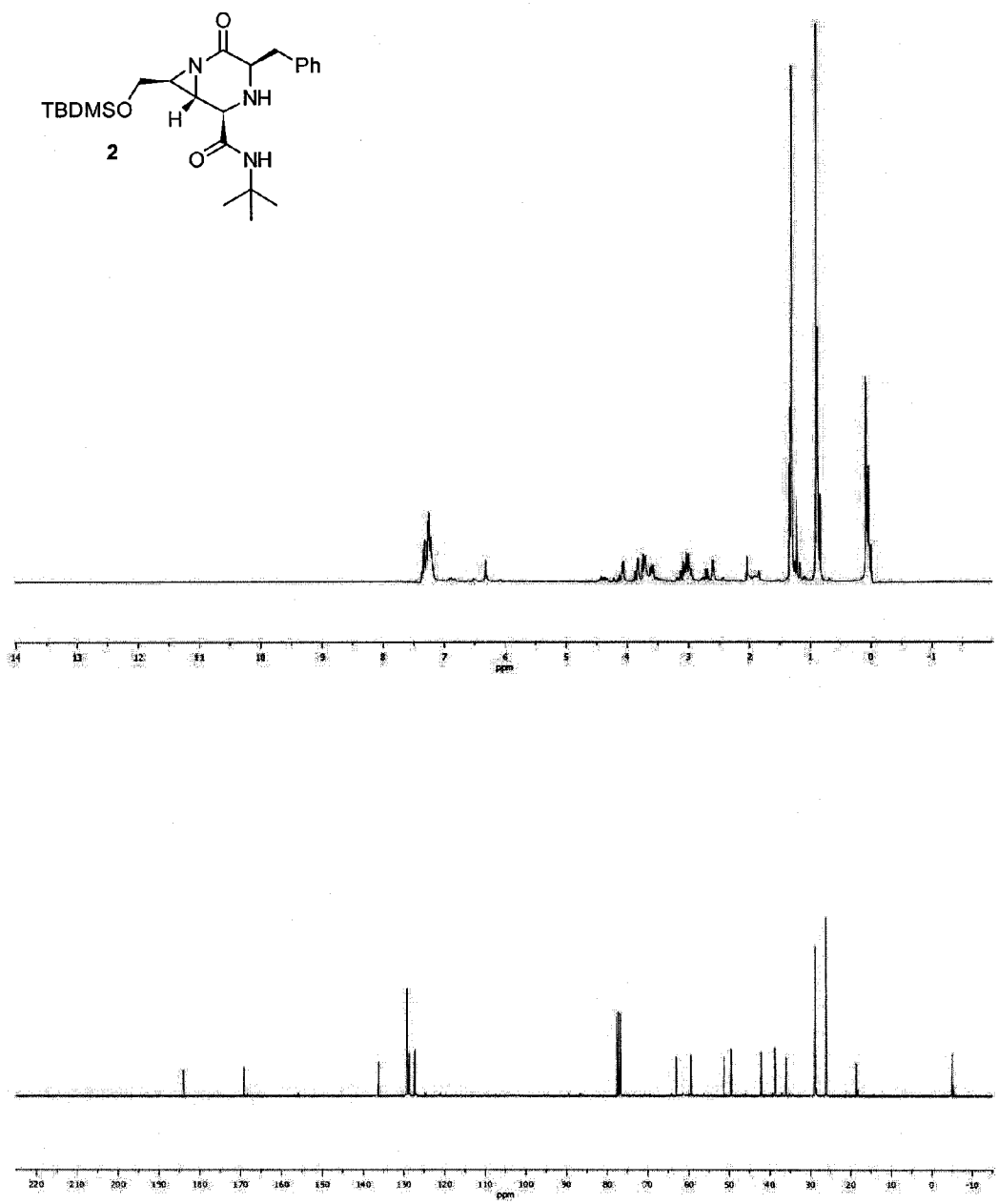
Figure 6. $^1$H and $^{13}$C NMR spectra for cyclic product 2.

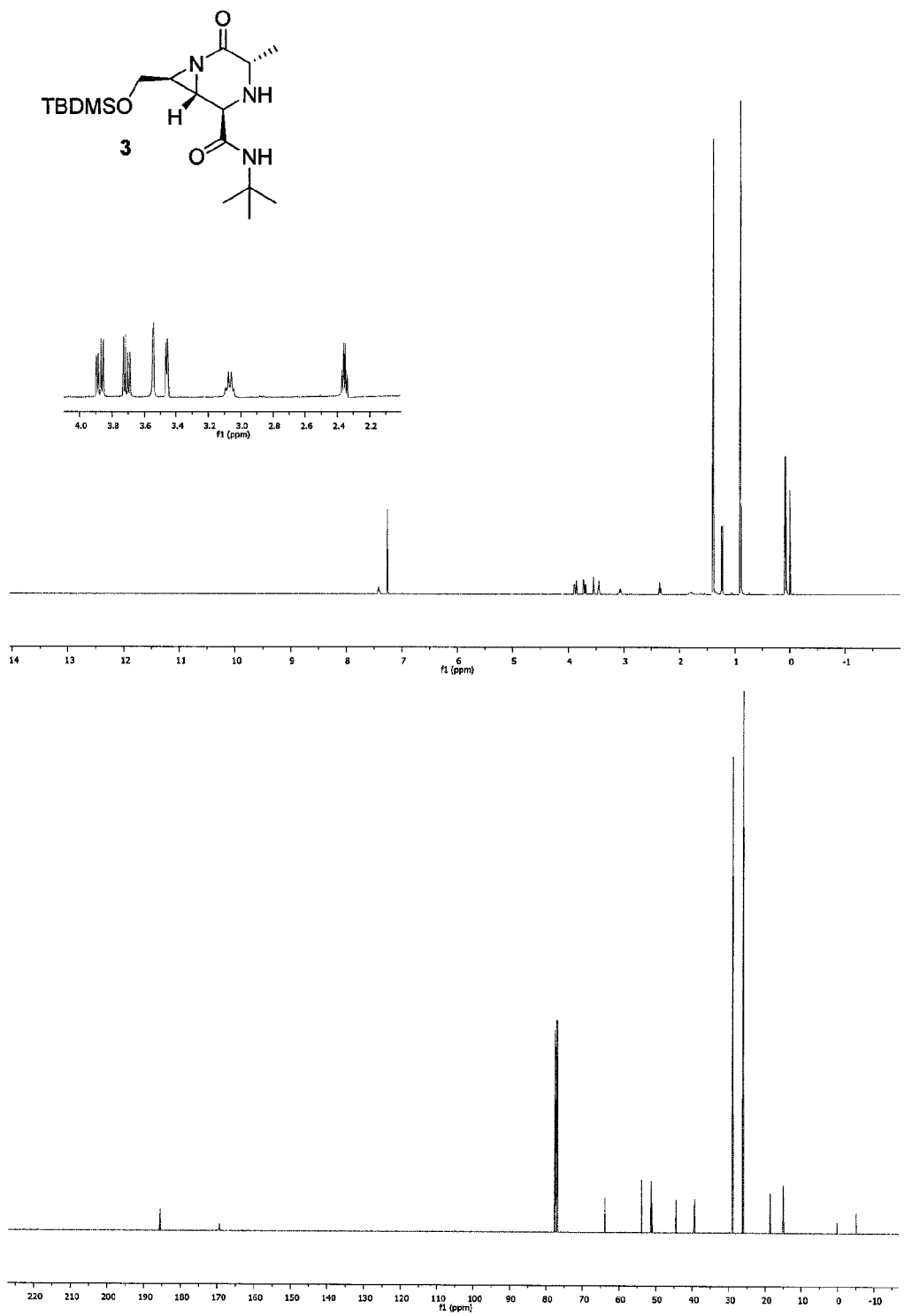
Figure 7. $^1$H and $^{13}$C NMR spectra for cyclic product 3.

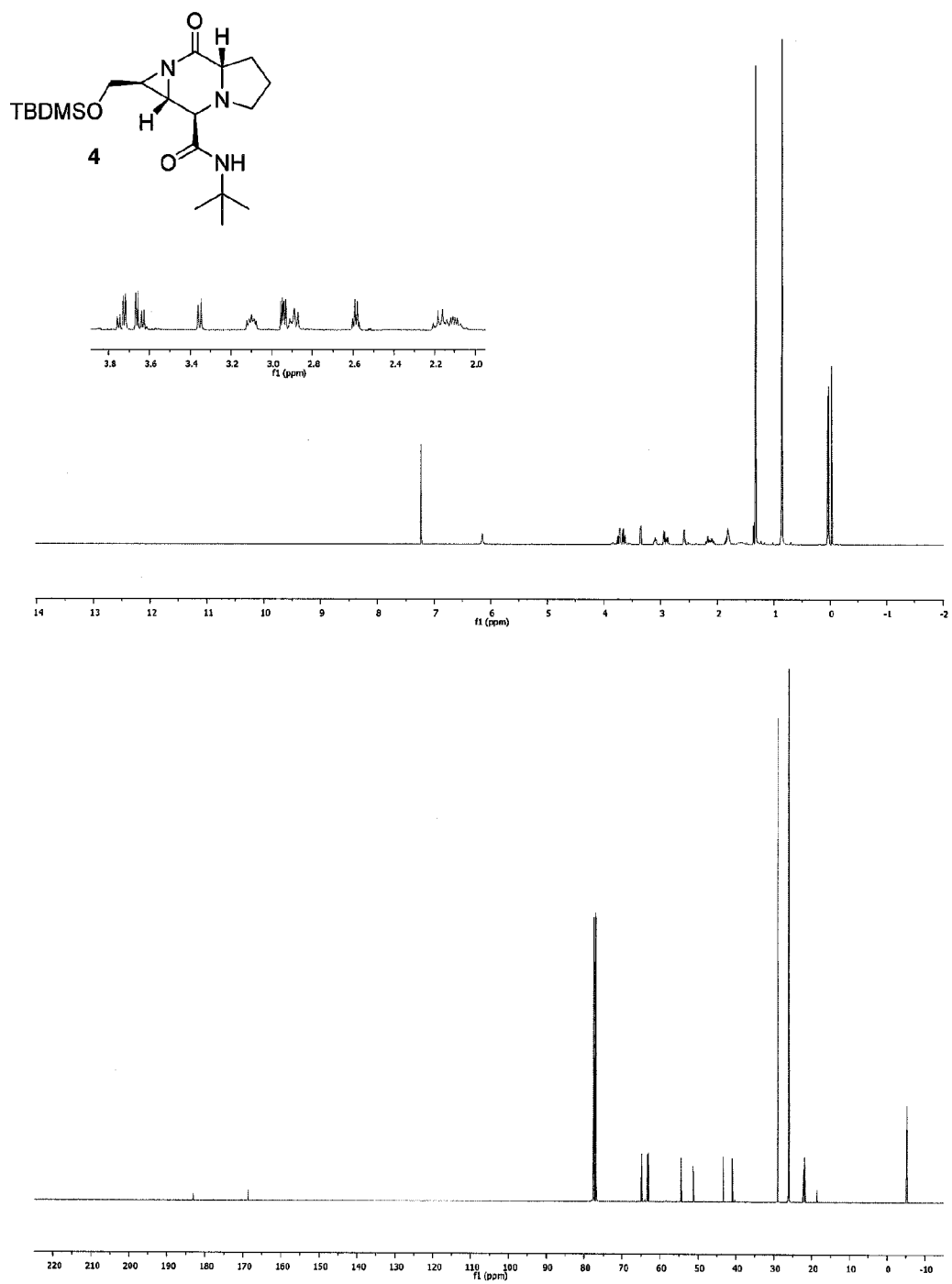
Figure 8. $^1$H and $^{13}$C NMR spectra for cyclic product 4.

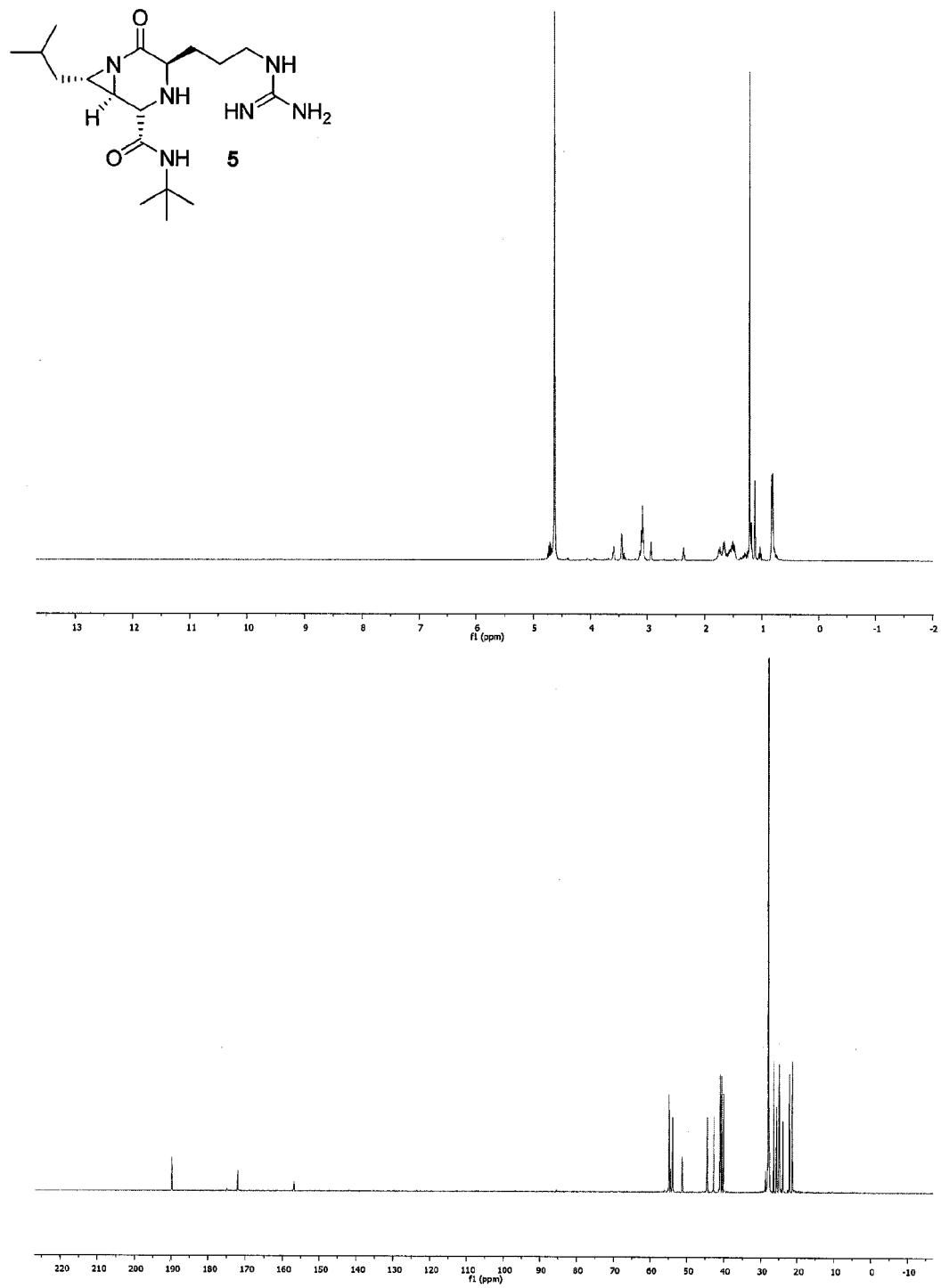
Figure 9. $^1$H and $^{13}$C NMR spectra for cyclic product 5.

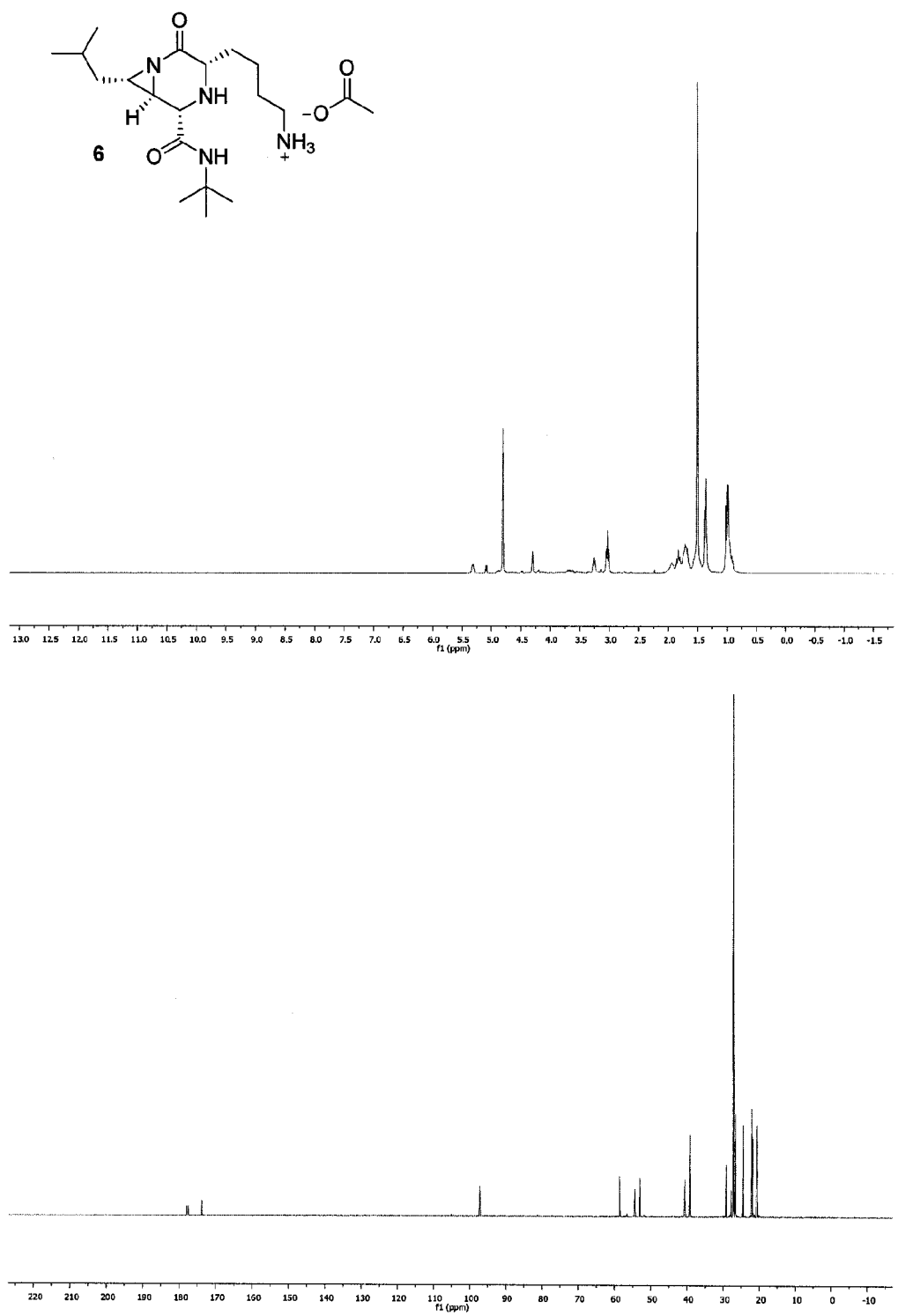
Figure 10. $^1$H and $^{13}$C NMR spectra for cyclic product 6.

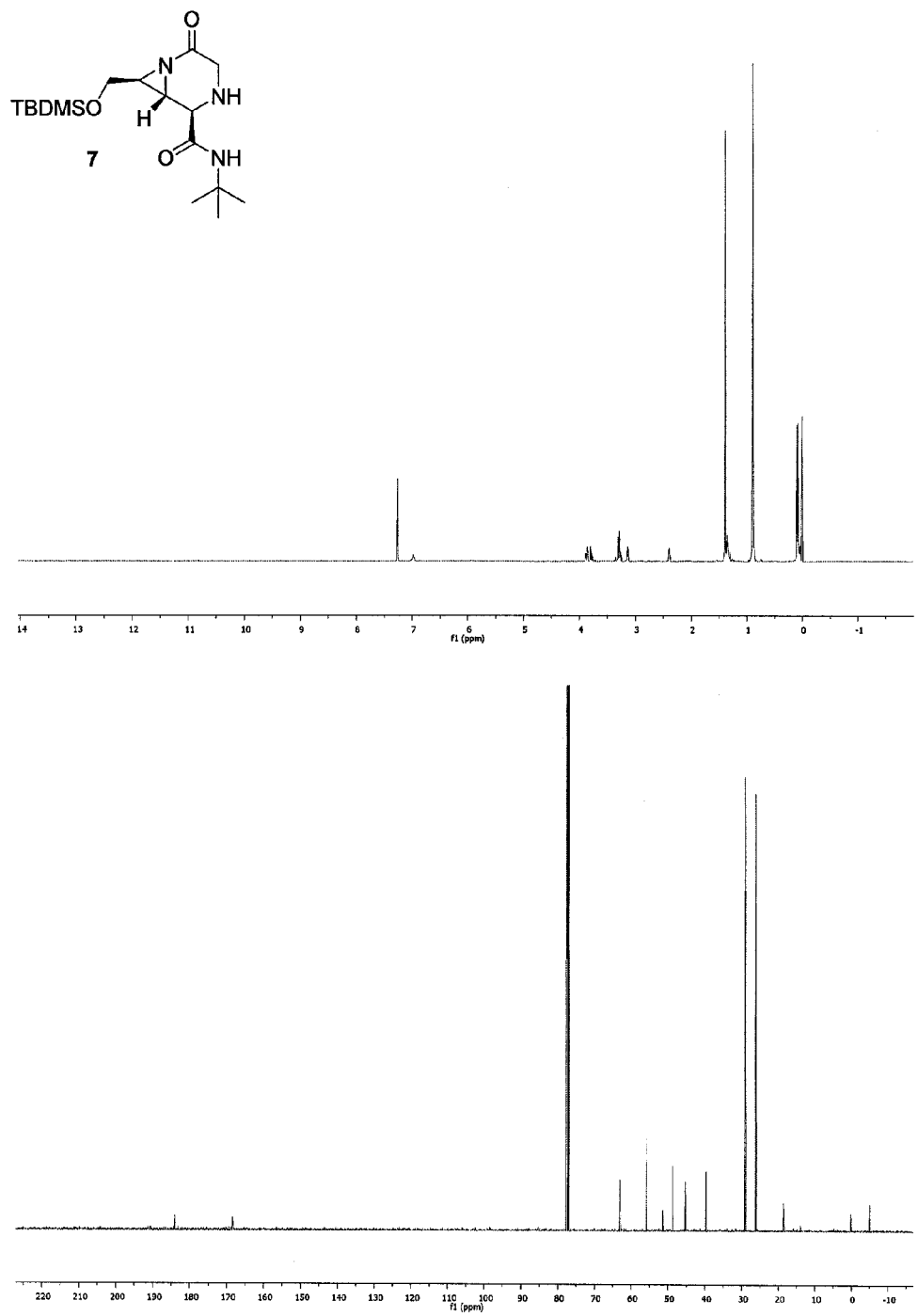
Figure 11. $^1$H and $^{13}$C NMR spectra for cyclic product 7.

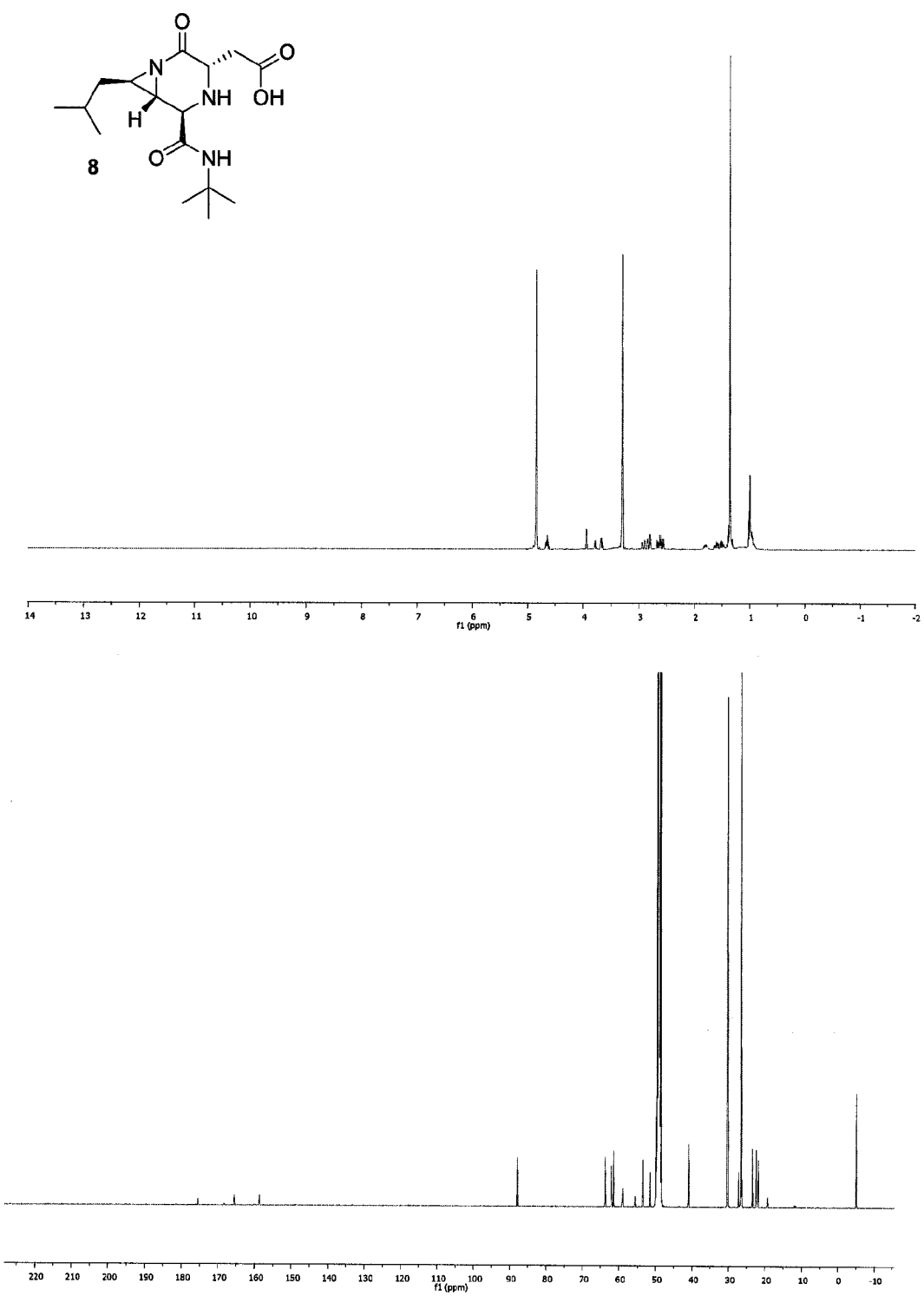
Figure 12. $^1$H and $^{13}$C NMR spectra for cyclic product 8.

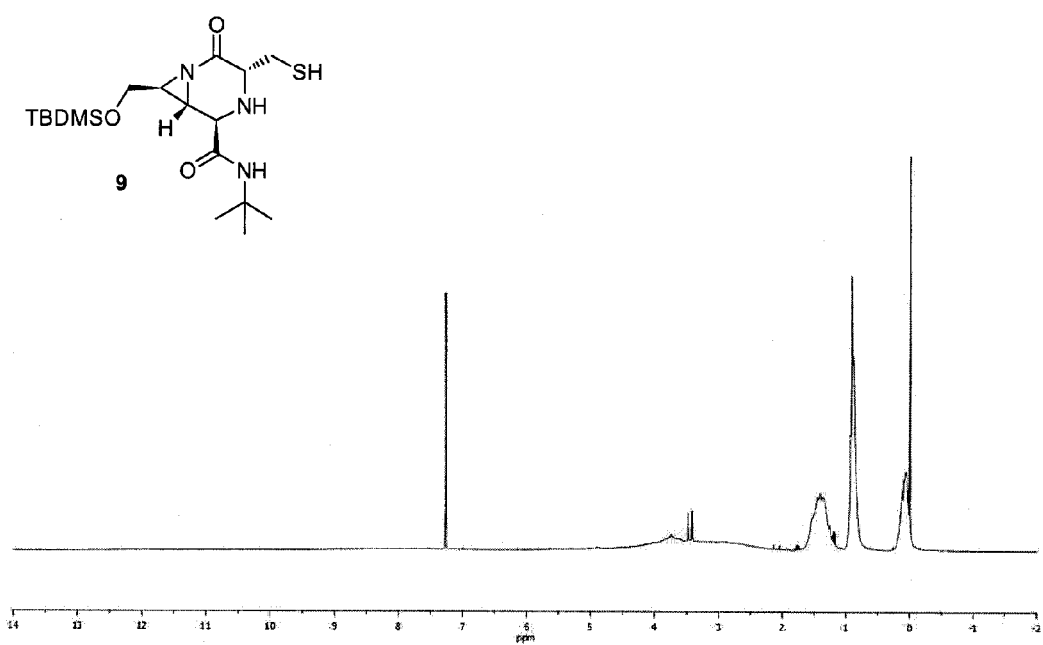
Figure 13. $^1$H NMR spectrum for cyclic product 9.

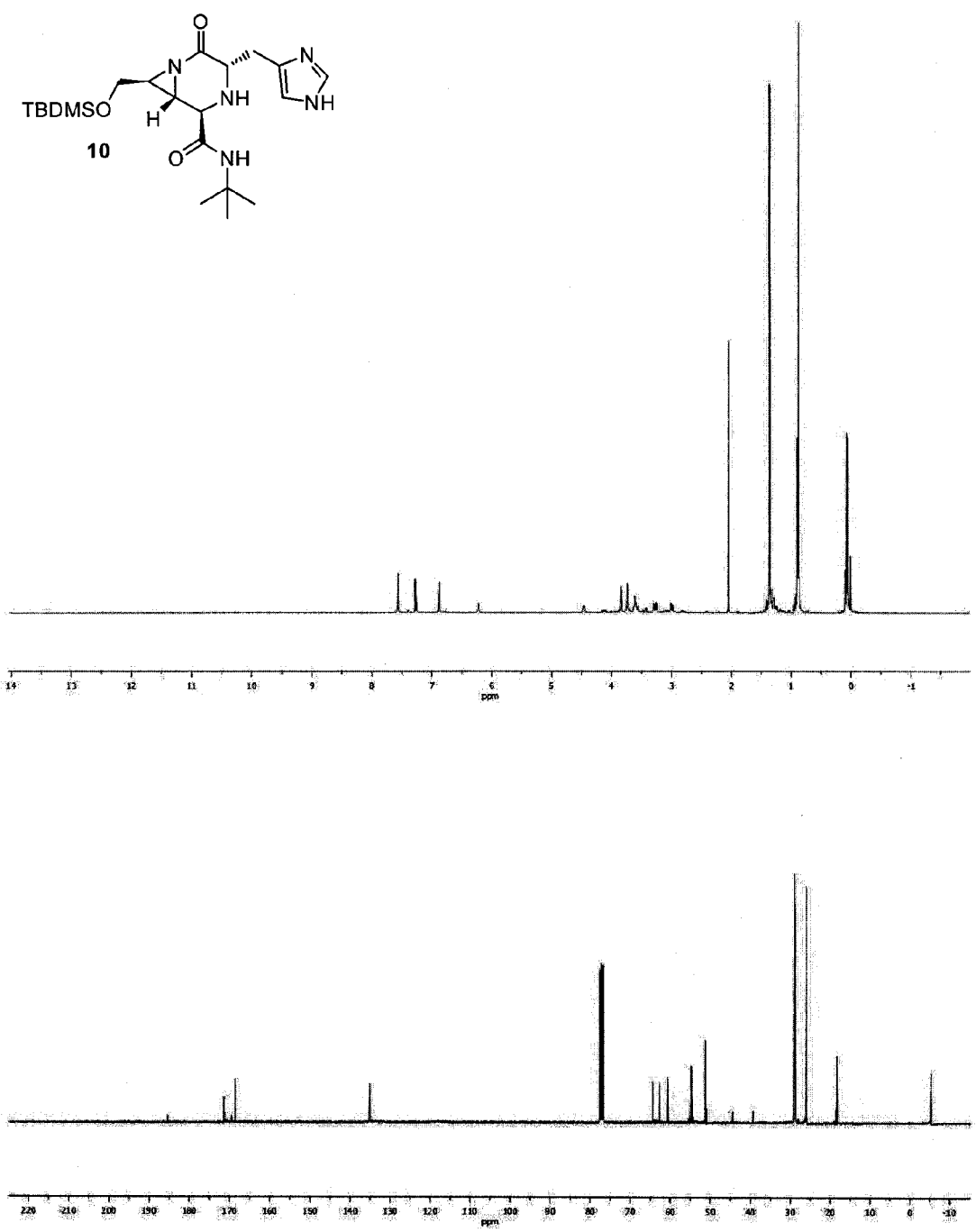
Figure 14. ¹H and ¹³C NMR spectra for cyclic product 10.

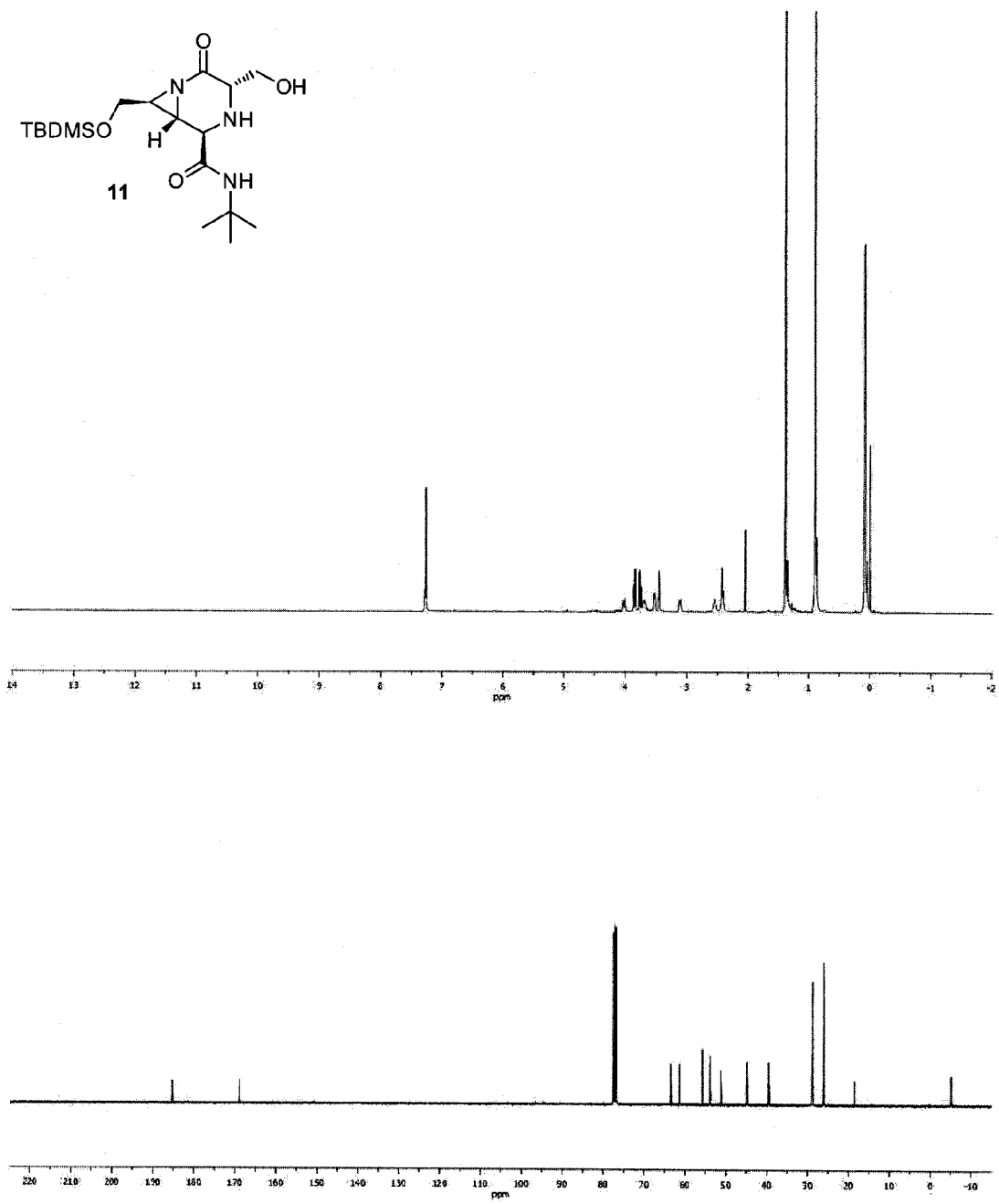
Figure 15. $^1$H and $^{13}$C NMR spectra for cyclic product 11.

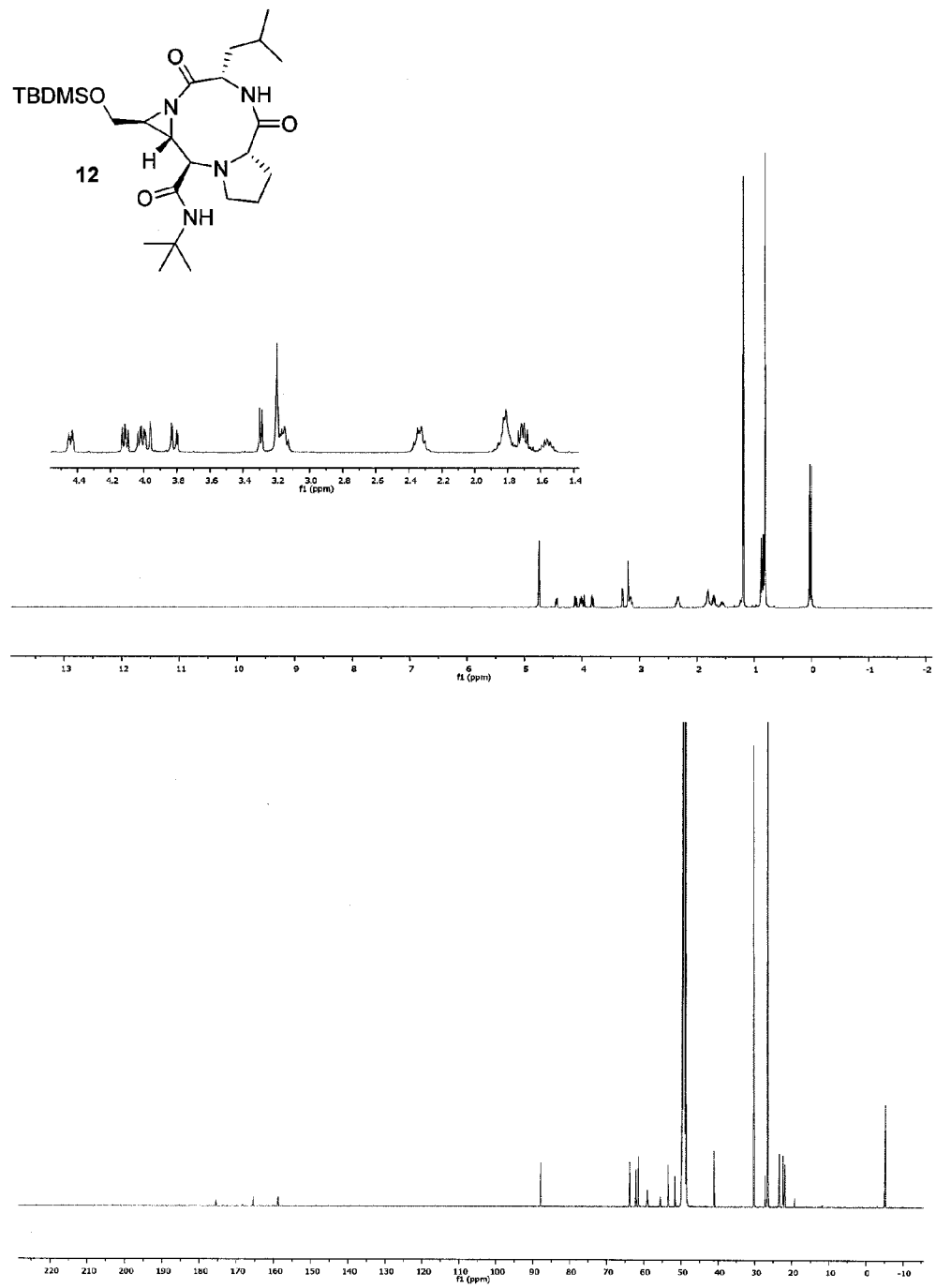
Figure 16. $^1$H and $^{13}$C NMR spectra for cyclic product 12.

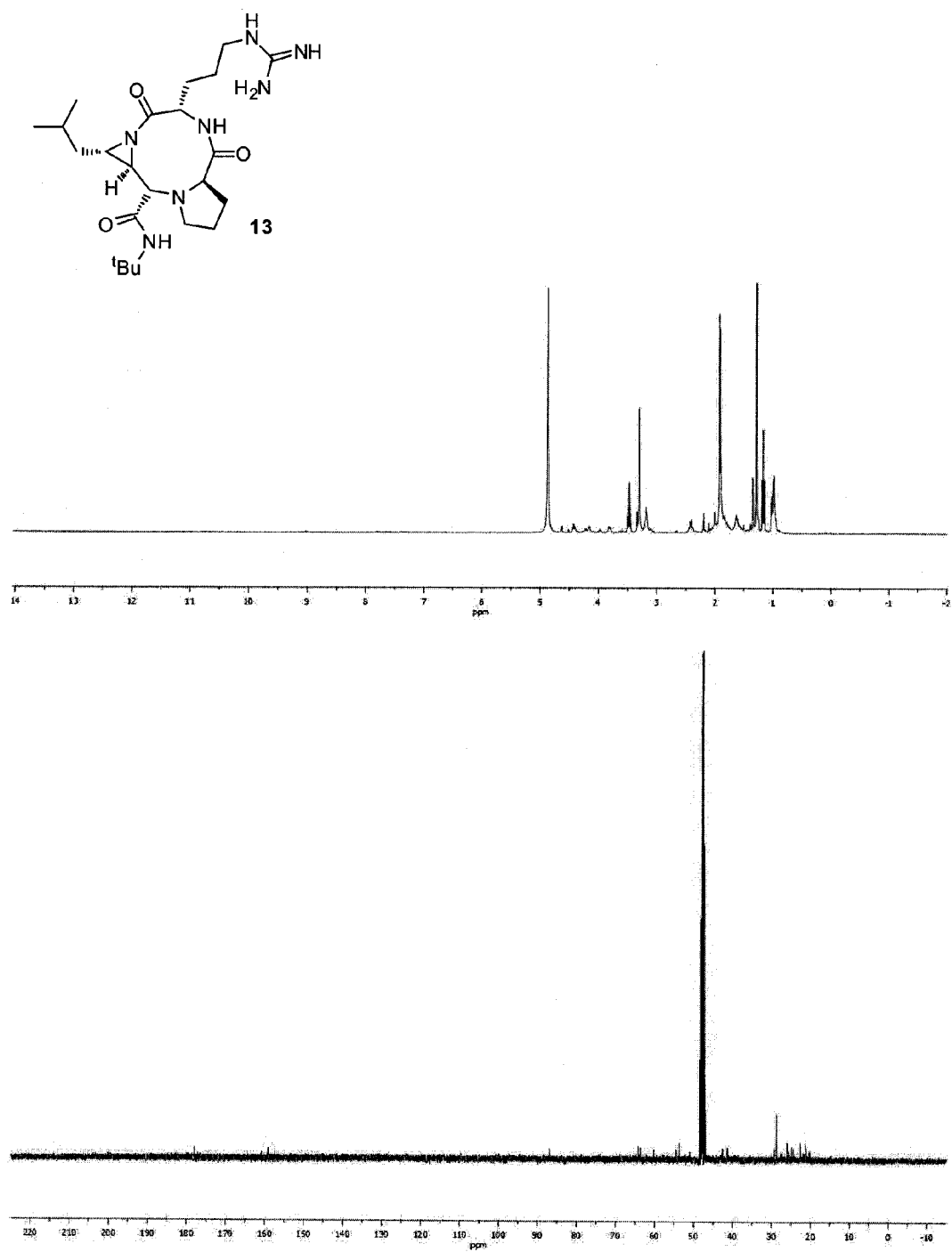
Figure 17. $^1$H and $^{13}$C NMR spectra for cyclic product 13.

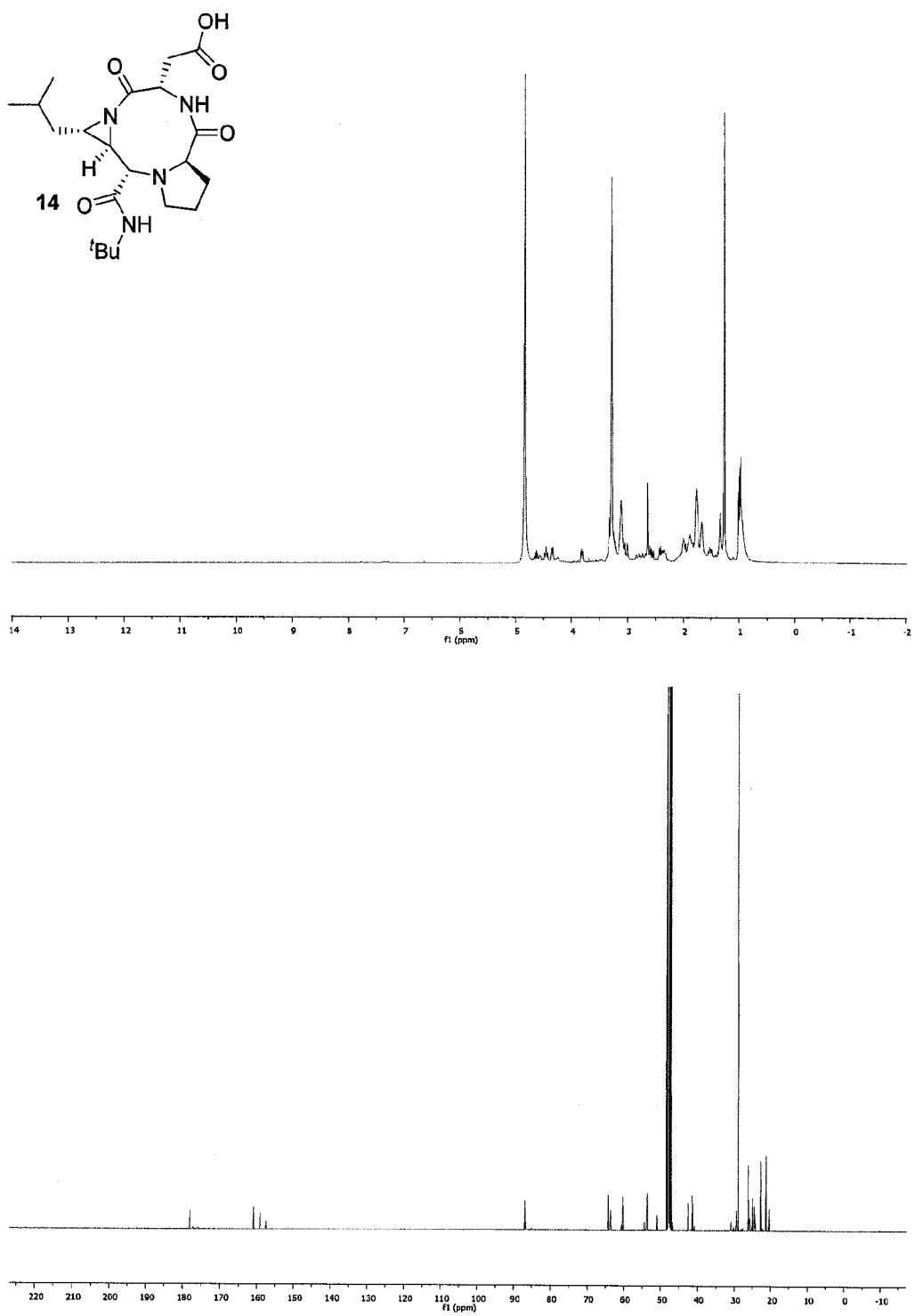
Figure 18. $^1$H and $^{13}$C NMR spectra for cyclic product 14.

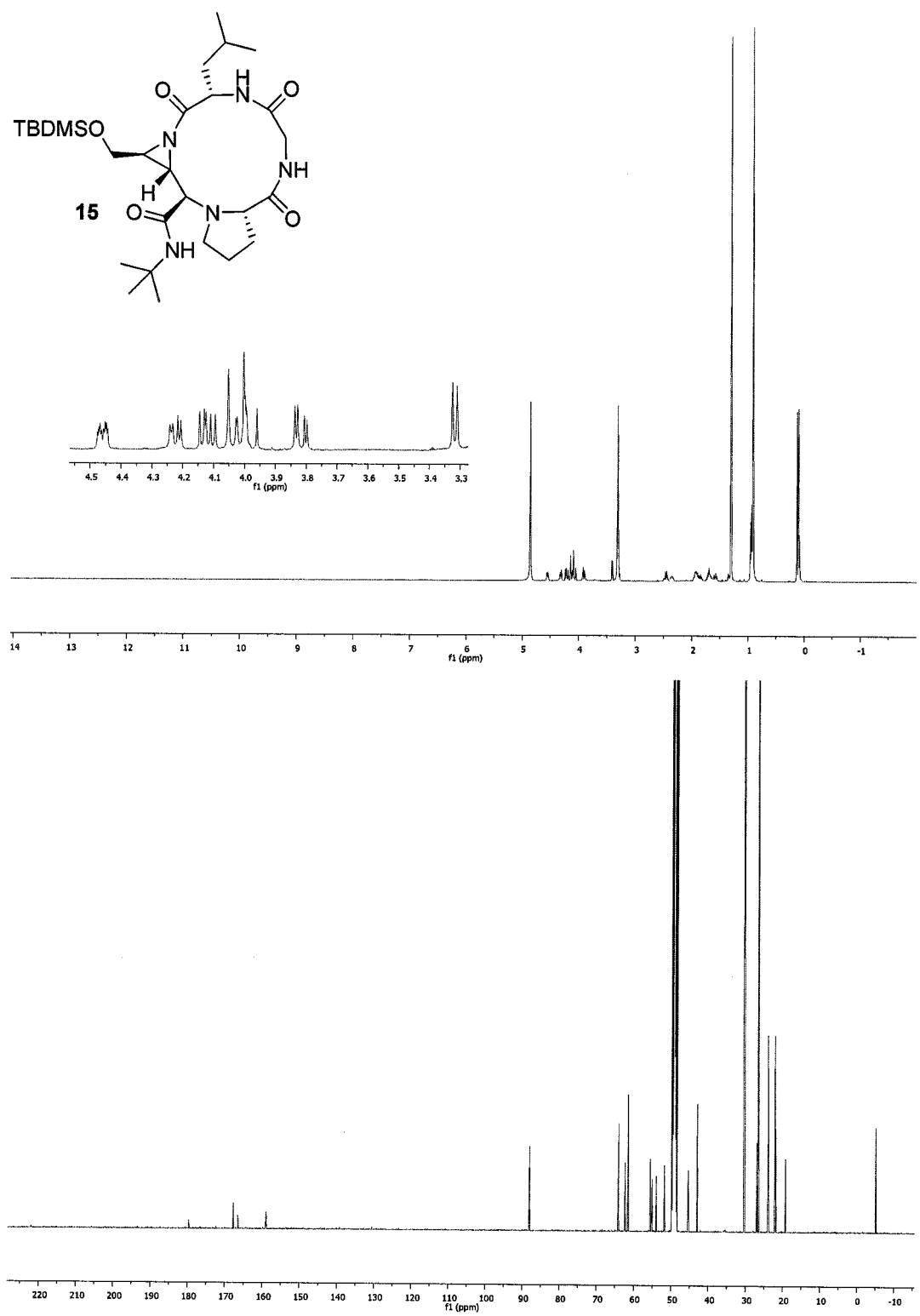
Figure 19. $^1$H and $^{13}$C NMR spectra for cyclic product 15.

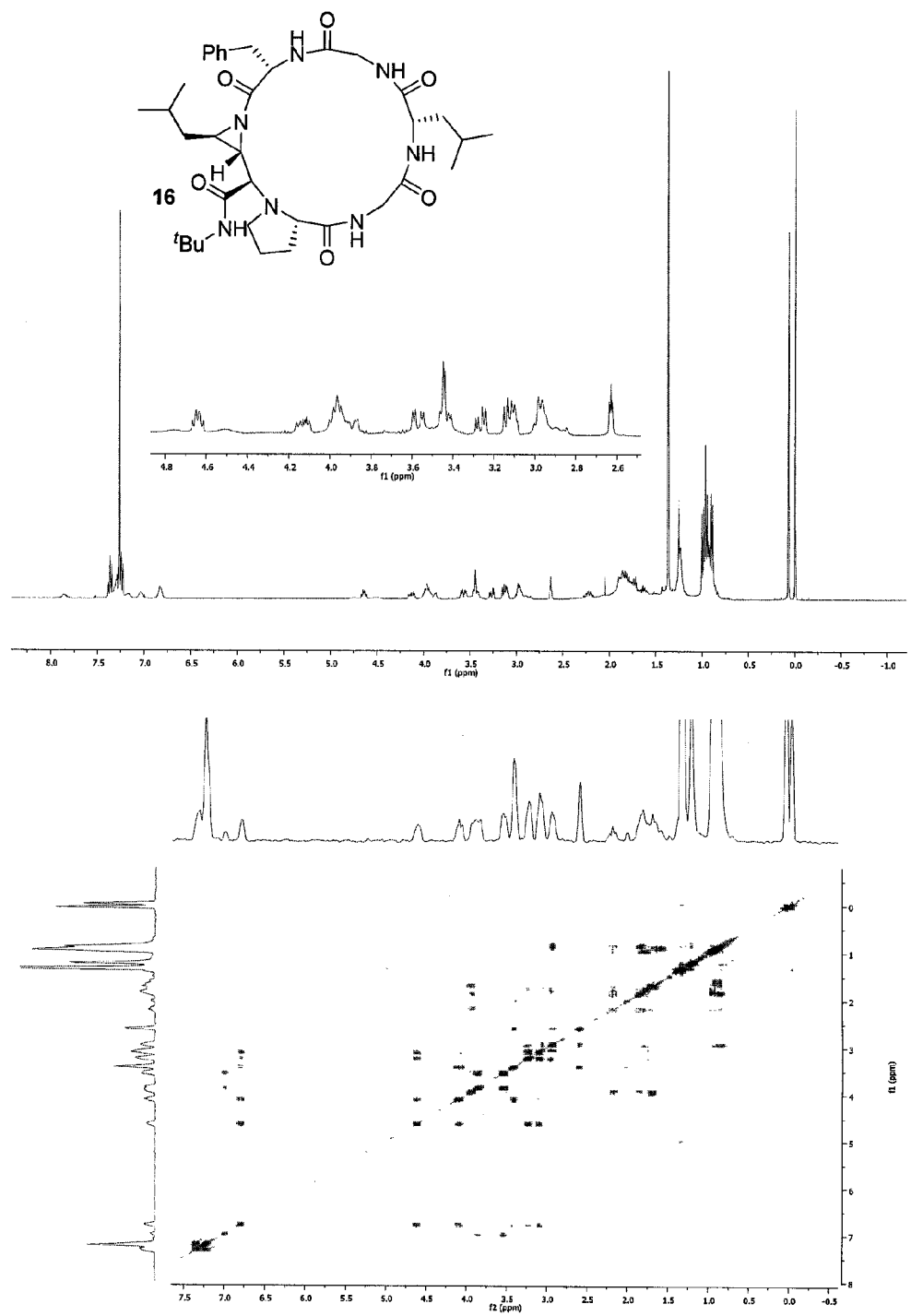
Figure 20. $^1$H, COSY and $^{13}$C NMR spectra for cyclic product 16.

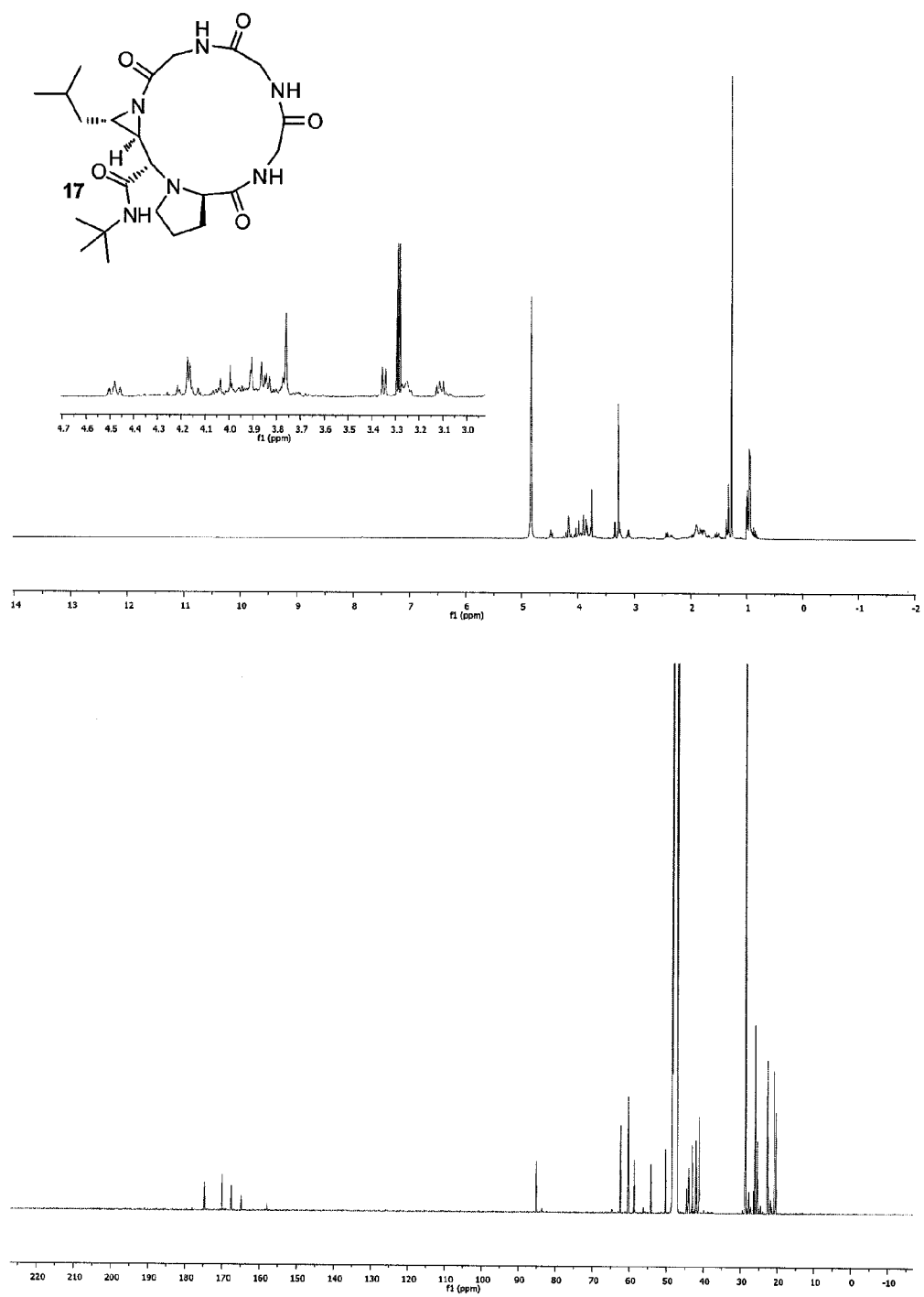
Figure 21. $^1$H and $^{13}$C NMR spectra for cyclic product 17.

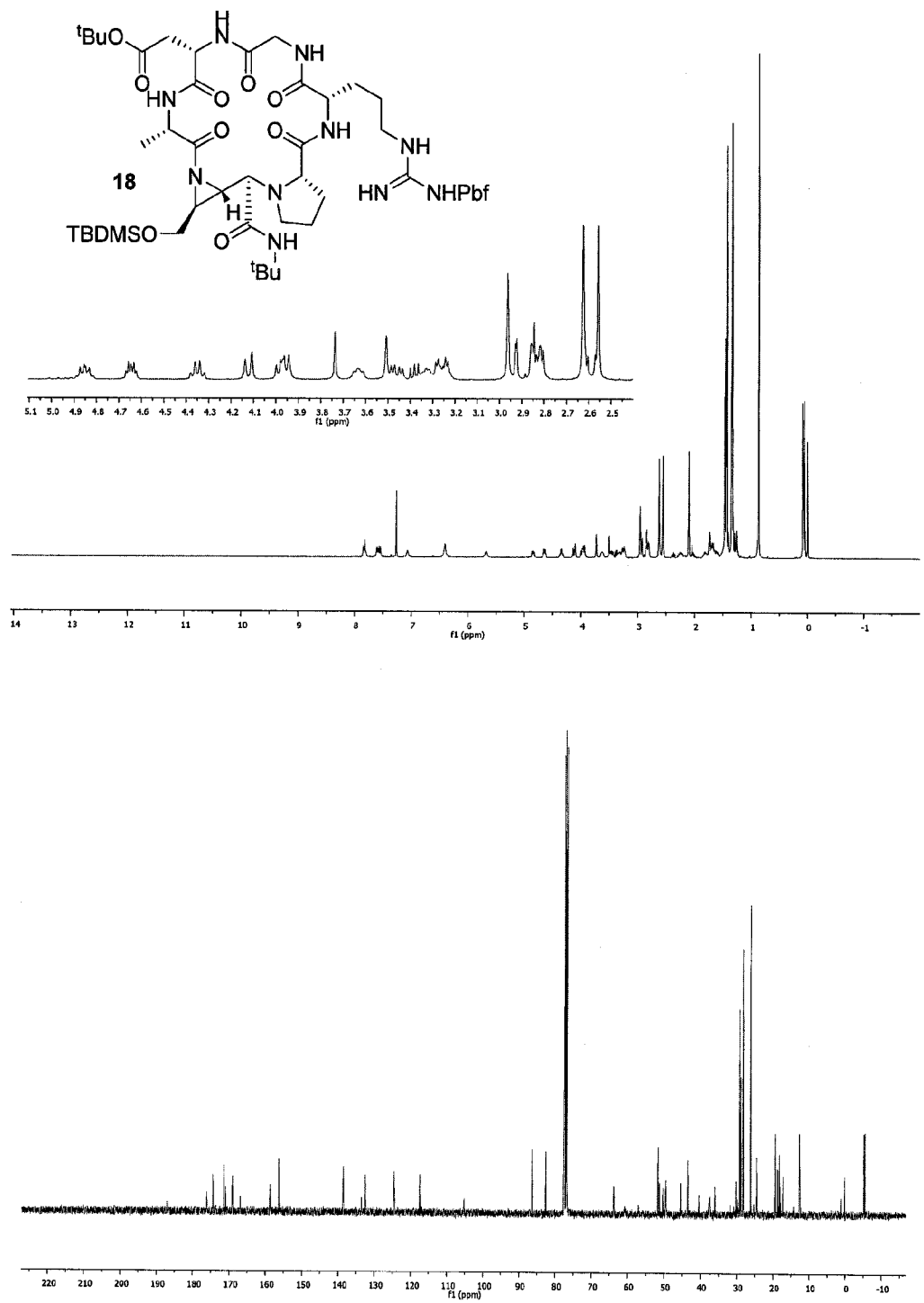
Figure 22. $^1$H and $^{13}$C NMR spectra for cyclic product 18.

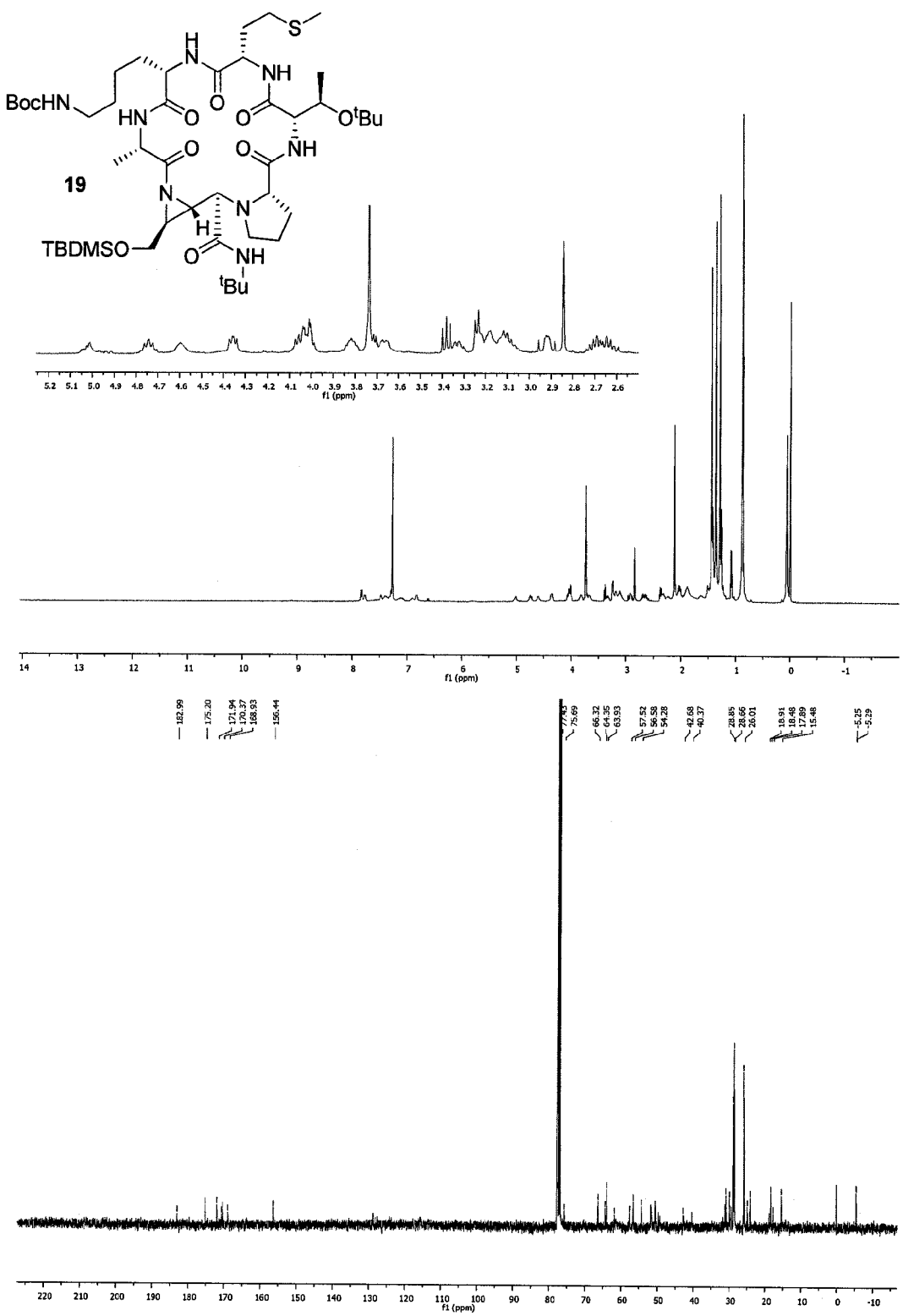
Figure 23. $^1$H and $^{13}$C NMR spectra for cyclic product 19.

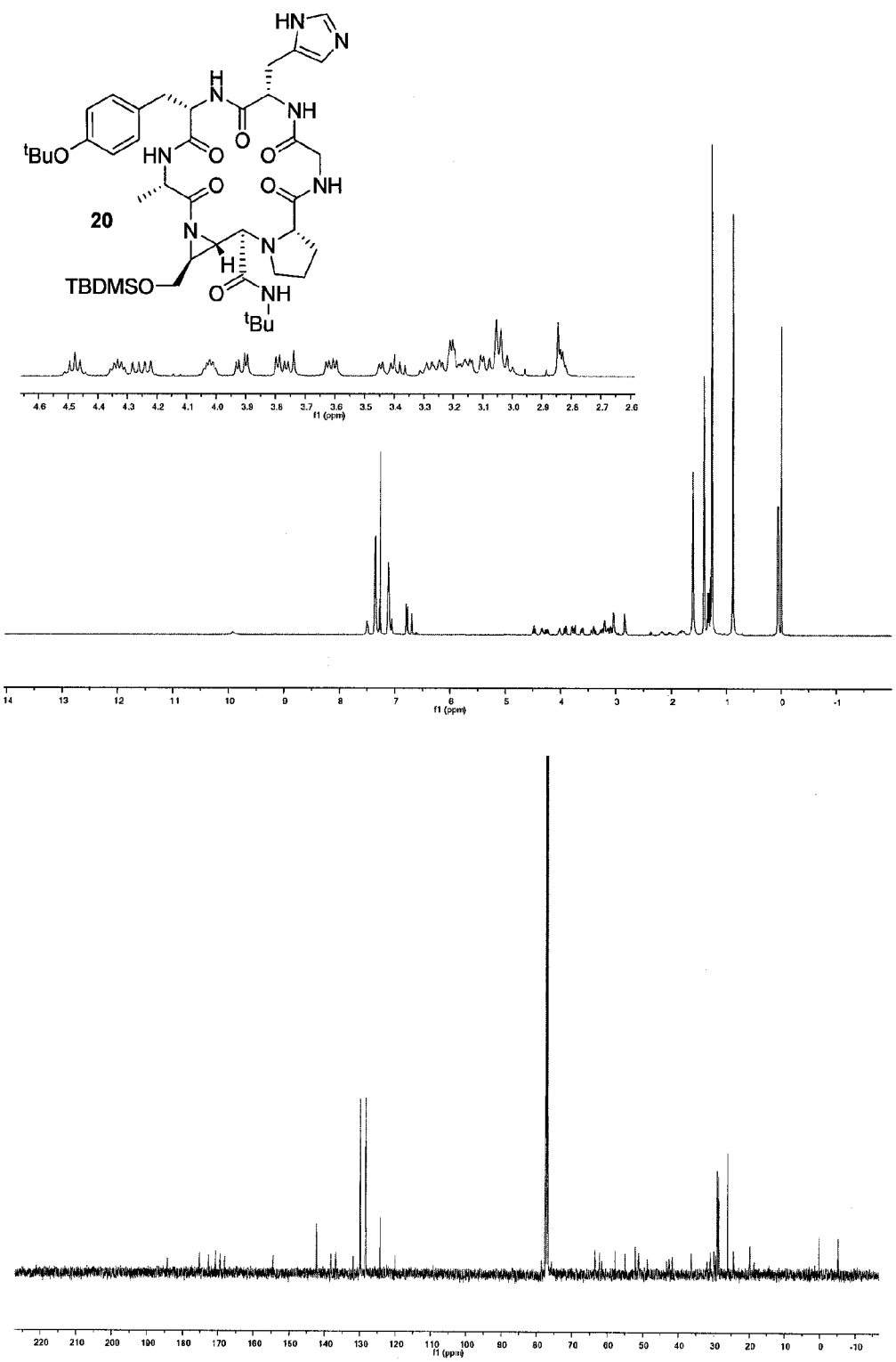
Figure 24. $^1$H and $^{13}$C NMR spectra for cyclic product 20.

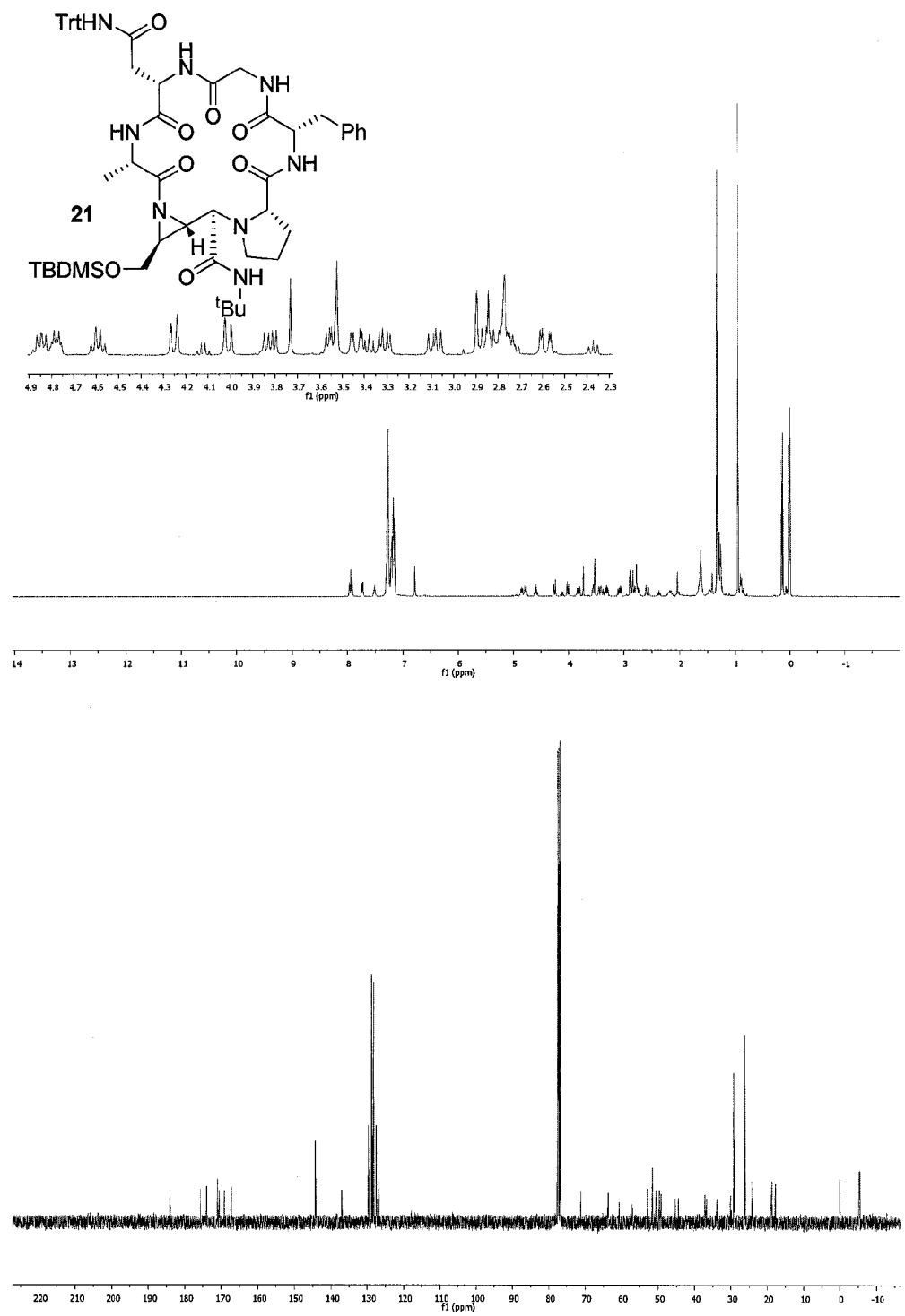
Figure 25. $^1$H and $^{13}$C NMR spectra for cyclic product 21.

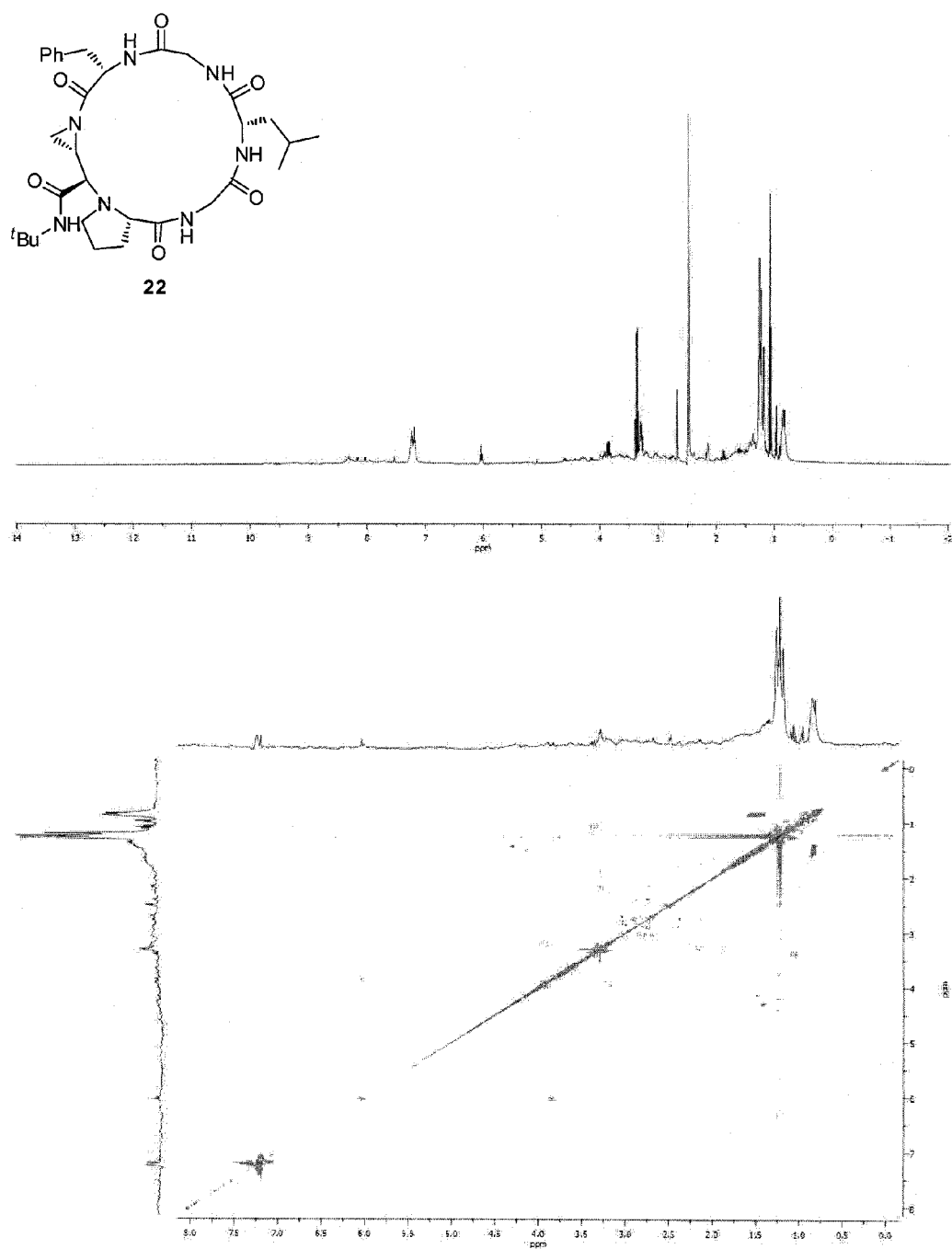
Figure 26. ¹H and COSY NMR spectra for cyclic product 22.

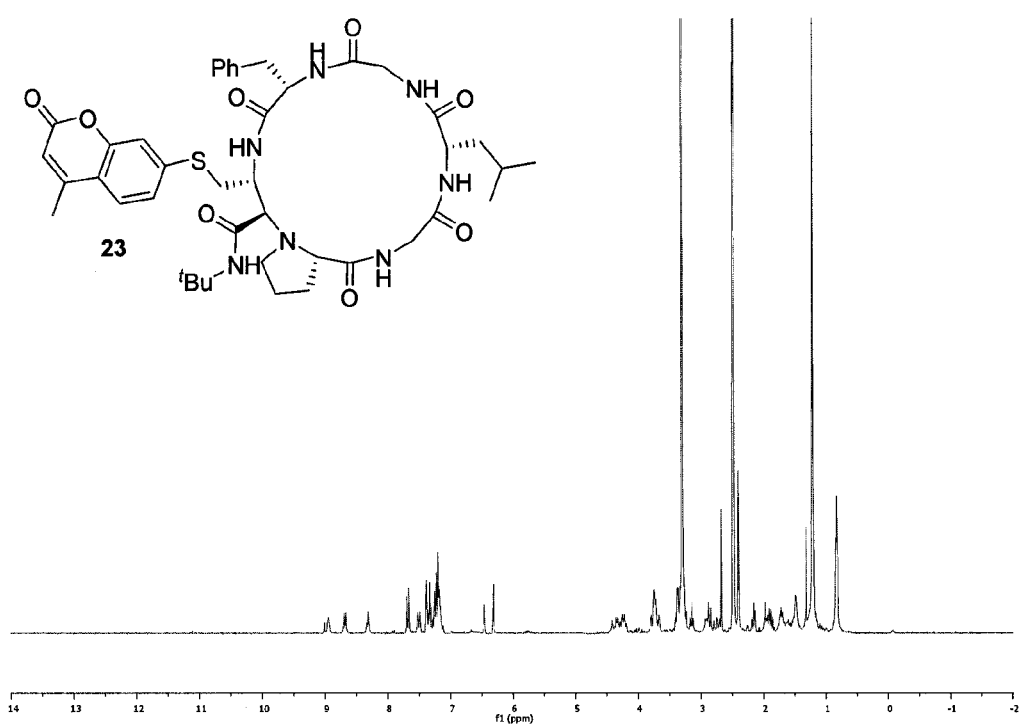
Figure 27. ¹H NMR spectrum for cyclic product 23.

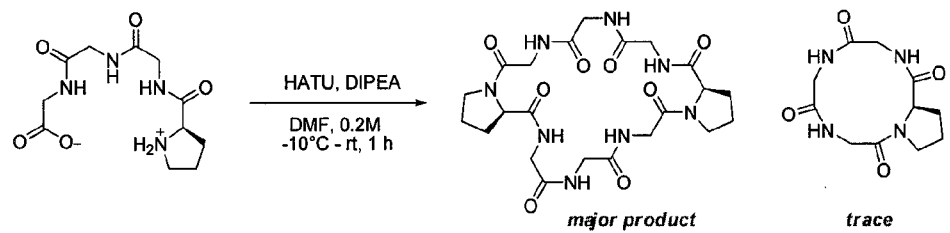
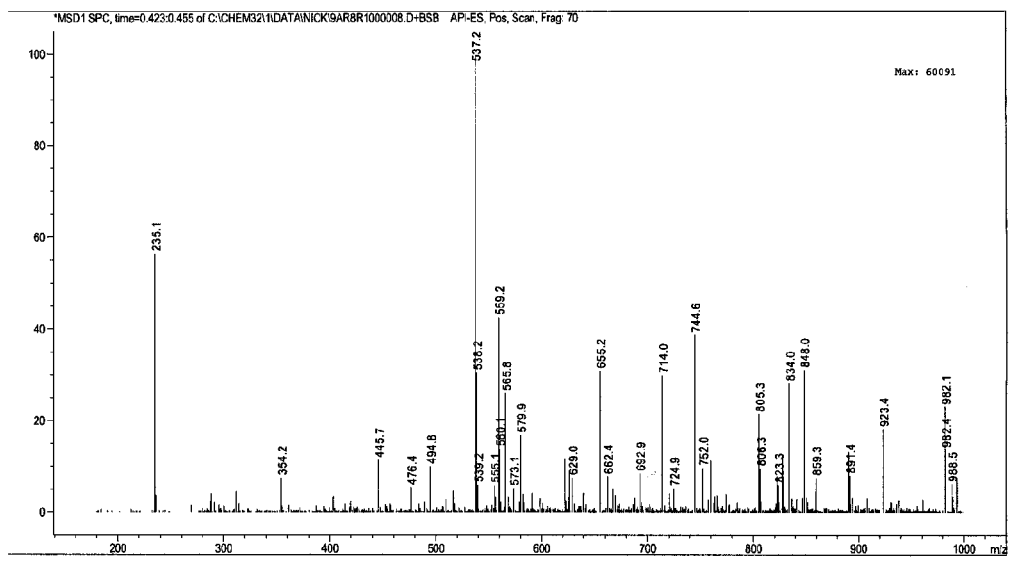
Figure 28. Crude LC-MS(ESI) analysis of HATU-mediated cyclization of Pro-Gly-Gly-Gly at 0.2M

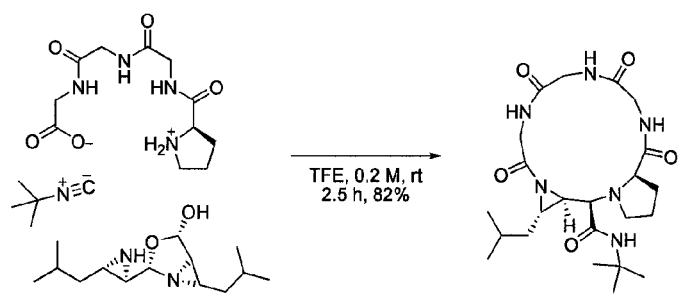
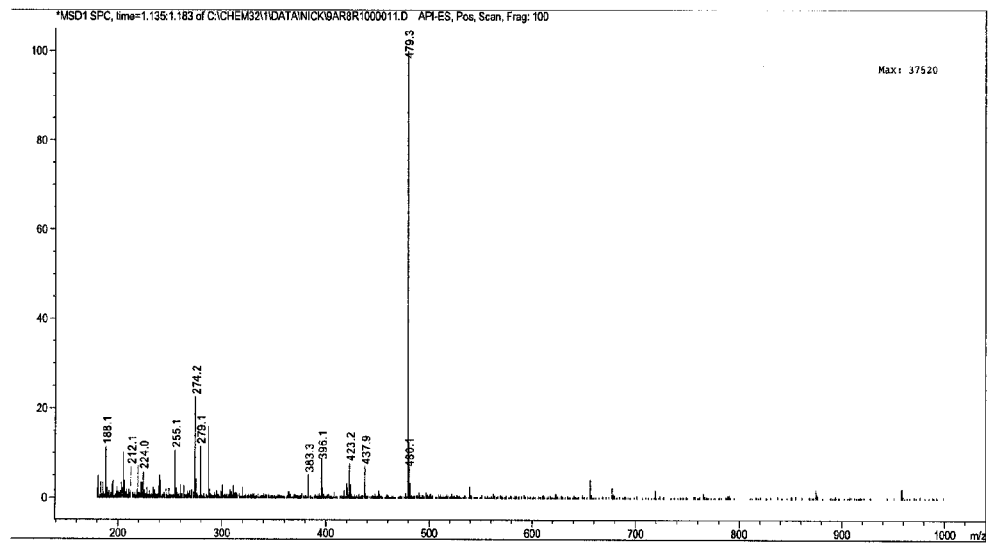
Figure 29. Crude LC-MS(ESI) analysis of isocyanide/amino aldehyde-mediated cyclization of Pro-Gly-Gly-Gly at 0.2M

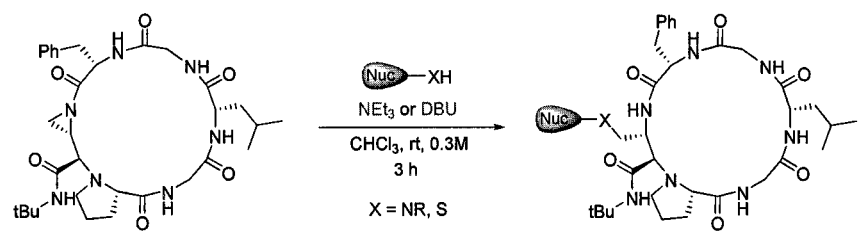
Figure 30. Nucleophilic ring-opening of aziridine-containing cyclic peptides.

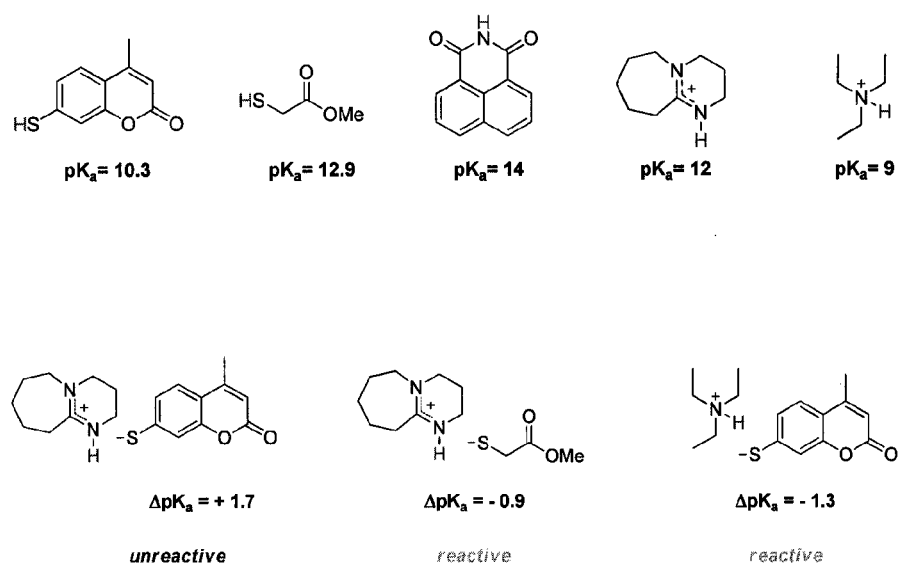
Figure 31. pK$_a$'s of thiols and ammonium ions and ΔpK$_a$ of ion pairs.

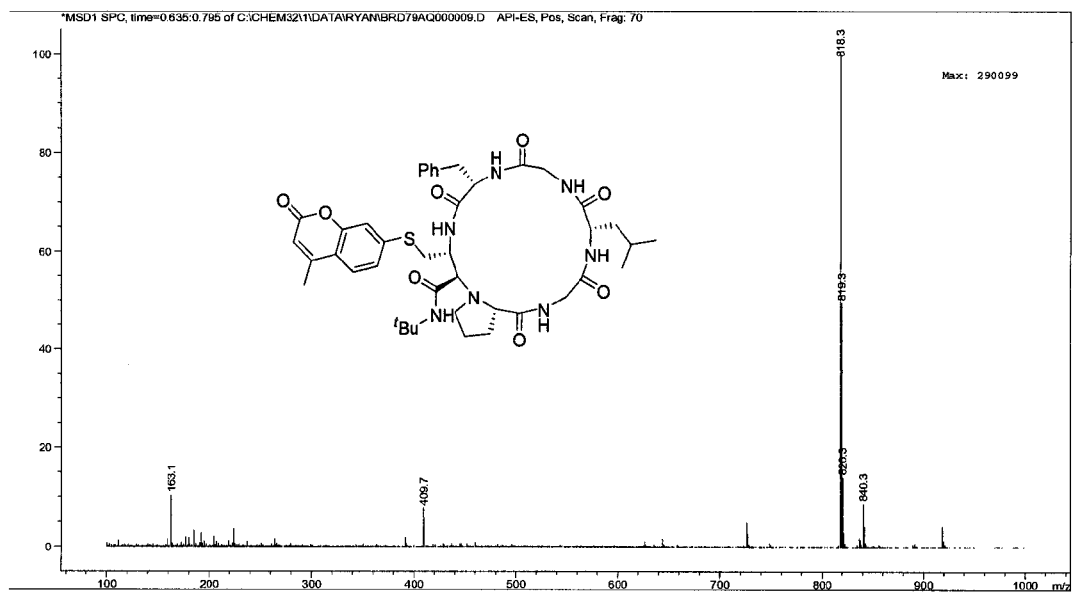
Figure 32. Crude reaction mixture of thiol opened product.

CYCLIC AMINO ACID MOLECULES AND METHODS OF PREPARING THE SAME

CROSS-REFERENCE TO RELATED APPLICATIONS

This application is the U.S. National Stage filing of International Application Ser. No. PCT/CA2010/000408, filed Mar. 16, 2010, which claims priority to U.S. Provisional Application Ser. No. 61/160,571, filed Mar. 16, 2009, which is incorporated herein by reference in its entirety.

FIELD

The present invention relates to cyclic amino acid molecules and methods of preparing the same, and in particular the macrocyclization of amino acids or linear peptides upon reaction with amphoteric amino aldehydes and isocyanides.

BACKGROUND

Peptides play vital roles by mediating a wide range of biological processes, acting as hormones, antibiotics, and signaling molecules. Due to the highly specific interaction with their biological targets, peptides have been widely used in medicine. However, the enormous therapeutic potential of peptides is not always easy to realize due to their low bioavailability. This shortcoming is a consequence of the degradation of peptides by endo- and exopeptididases, which results in poor in vivo stability of peptides. Compared to their linear counterparts, cyclic peptides are more resistant to degradation. There are two main reasons for this stability. Firstly, exopeptidases cannot cleave the cyclic peptide at its (non-existent) ends. Secondly, cyclic peptides, especially those with a small-to-medium ring size, are protected against endopeptidases because the constrained cyclic peptide backbone prevents the adaptation of the required extended conformation during proteolysis. In addition, the reduced charge and intramolecular hydrogen bonding within cyclic peptides facilitate passive membrane permeability, which contributes to their enhanced bioavailability. Most significantly, conformational constraints imposed on the amino acid sequence by the cyclic topology maximize enthalpic interactions between cyclic peptides and their biochemical targets while ensuring favourable entropy of binding.

There has been enormous interest in both naturally occurring and synthetic cyclic peptides as scaffolds that pre-organize an amino acid sequence into a rigid conformation.[1] Amongst the vast number of known cyclic peptides, rigid small-to-medium sized rings have been of particular interest. Various cyclolactamization and non-peptidic cyclization methods[2] have been developed.

The macrocyclization of linear precursors is afflicted by several thermodynamic and kinetic challenges that arise from the conformational preferences of linear peptides. The chain/ring conformational equilibrium is the central obstacle facing synthesis of cyclic molecules from acyclic precursors. Short linear peptides can easily adopt a circular conformation, which is driven by ion pairing between the N- and C-termini (Scheme 1, A).[3] Despite the unfavorable entropy, these circular conformations are thermodynamically favoured due to the enthalpy garnered through electrostatic and other polar interactions. As shown in Scheme 1. conventional activation reagents tend to remove the zwitterionic character of the peptide, rendering it incapable of forming ion pairs. Consequently, without enthalpic contribution from electrostatics and other polar interactions, the activated peptide adopts a random linear conformation (Scheme 1. B). In order for macrocyclization to occur, the activated peptide must adopt a pre-cyclization conformation (C) prior to forming the desired cyclic molecule (D). High dilution, on the order of $10^{-4}$ or greater, is essential to limiting the formation of by-products arising from cyclodimerization,[4] cyclotrimerization, and polymerization.[5] Unfortunately, dilution brings about long reaction times, which in turn provoke background processes such as epimerization. Amongst the most challenging cyclizations are those attempted on linear peptides containing less than seven residues.[6,7]

Scheme 1. A common peptide macrocyclization strategy.

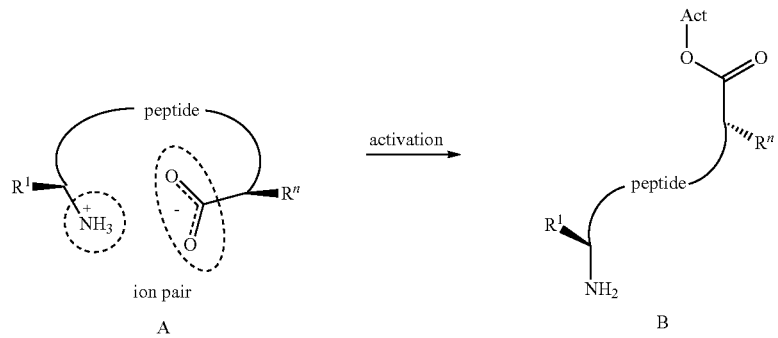

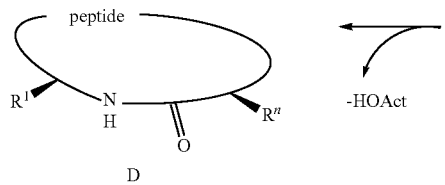

D

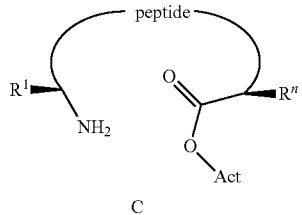

C

Another common challenge in exploring macrocyclic chemistry space has to do with late-stage modification. This is a historic challenge for macrocyclic compound libraries built in the biotechnology and pharmaceutical companies. Their typical cyclization techniques (ring-closing metathesis, Huisgen cycloaddition) do not naturally lend themselves to further elaboration. Functional group handles must be built in prior to cyclization to achieve this goal.

SUMMARY OF THE INVENTION

In one aspect, there is provided a process to produce a cyclic amino acid molecule comprising reacting an amino acid molecule, having an amino terminus and a carboxyl terminus, with an isocyanide and a compound having formula (Ia) and/or (Ib):

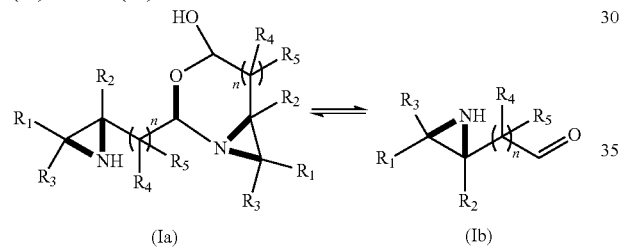

wherein:
n=0 or 1. and $R_1$, $R_2$, $R_3$, $R_4$ and $R_5$ are independently selected from H; lower alkyl; alkenyl; heterocycle; cyckoalkyl; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -lower alkyl-aryl, or NR$_a$R$_b$, where R$_a$ and R$_b$ are independently selected from H, lower alkyl, aryl or -lower alkyl-aryl; —C(O)R$_c$, wherein R$_c$ is selected from lower alkyl, aryl or -lower alkyl-aryl; or -lower alkyl-OR$_d$, wherein R$_d$ is a suitable protecting group or OH group; all of which are optionally substituted at one or more substitutable positions with one or more suitable substituents; and
the aldehyde component thereof may optionally be in its bisulfate adduct form;
and the amino acid molecule is an amino acid, a linear peptide or a salt of the foregoing, provided that if the amino acid molecule is a linear peptide, the compound comprises an aziridine chiral center proximal to the aldehyde with matching stereochemistry to the carbon atom proximal to the amino terminus of the peptide.

In another aspect, there is provided a cyclic amino acid molecule prepared using the process described herein.

In another aspect, there is provided a cyclic amino acid molecule of formula (II):

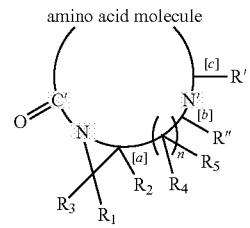

wherein,
n=0 or 1. and $R_1$, $R_2$, $R_3$, $R_4$ and $R_5$ are independently selected from H; lower alkyl; aryl; heteroaryl; alkenyl; heterocycle; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -loweralkyl-aryl, or NR$_a$R$_b$, where R$_a$ and R$_b$ are independently selected from H, lower alkyl, aryl or -loweralkyl-aryl; —C(O)R$_c$, wherein R$_c$ is selected from lower alkyl, aryl or -lower alkyl-aryl; or -lower alkyl-OR$_d$, wherein R$_d$ is a suitable protecting group or OH group; all of which are optionally substituted at one or more substitutable positions with one or more suitable substituents,
bonds [a] and [b] are syn to each other;
R' is an amino acid side chain of the amino terminus amino acid;
R" is an optionally substituted amide;
and the amino acid molecule is an amino acid or a linear peptide, wherein N' is the nitrogen at the amino terminus end of the amino acid molecule and C' is the carbon at the carboxy terminus end of the amino acid molecule, and provided that if the amino acid molecule is a linear peptide, bonds [a] and [c] are anti to each other.

In another aspect, there is provided use of a compound for cyclizing an amino acid molecule, wherein the compound has the formula (Ia)/(Ib):

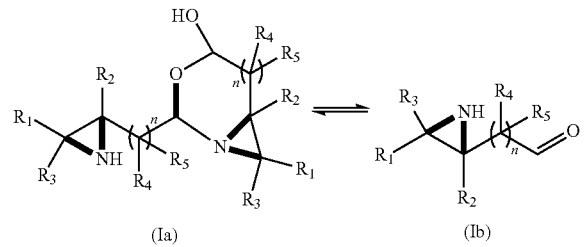

comprises an α-stereocenter at the carbon atom proximal to the aldehyde group with matching stereochemistry to the carbon atom proximal to the amino terminus of the amino acid molecule; and n=0 or 1. and $R_1$, $R_2$, $R_3$, $R_4$ and $R_5$ are independently selected from H; lower alkyl; aryl; heteroaryl; alkenyl; heterocycle; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -loweralkyl-aryl, or —NR$_a$R$_b$, where R$_a$ and R$_b$ are independently selected from H, lower alkyl, aryl or -loweralkyl-aryl; —C(O)R$_c$, wherein R$_c$ is selected from lower alkyl, aryl or -loweralkyl-aryl; or -lower alkyl-OR$_d$, wherein R$_d$ is a suitable protecting group; all of which are optionally substituted at one or more substitutable positions with one or more suitable substituents; and the amino acid molecule is an amino acid, a linear peptide or a salt of the foregoing, provided that if the amino acid molecule is a linear peptide, the compound comprises an aziridine chiral center proximal to the aldehyde with matching stereochemistry to the carbon atom proximal to the amino terminus of the peptide.

BRIEF DESCRIPTION OF THE FIGURES

Embodiments of the invention may best be understood by referring to the following description and accompanying drawings. In the description and drawings, like numerals refer to like structures or processes. In the drawings:

FIG. 1 is a $^1$H NMR comparison of crude reaction mixtures using isomers of leucine.

FIG. 2 is a scheme depicting a mismatched reaction leading to aminal products.

FIG. 3 is a matched reaction leading to a cyclic product.

FIG. 4 shows the chemical structures of the cyclic products synthesized by Methods 1-3.

FIG. 5 is the $^1$H and $^{13}$C NMR spectra for cyclic product 1.
FIG. 6 is the $^1$H and $^{13}$C NMR spectra for cyclic product 2
FIG. 7 is the $^1$H and $^{13}$C NMR spectra for cyclic product 3.
FIG. 8 is the $^1$H and $^{13}$C NMR spectra for cyclic product 4.
FIG. 9 is the $^1$H and $^{13}$C NMR spectra for cyclic product 5.
FIG. 10 is the $^1$H and $^{13}$C NMR spectra for cyclic product 6.
FIG. 11 is the $^1$H and $^{13}$C NMR spectra for cyclic product 7.
FIG. 12 is the $^1$H and $^{13}$C NMR spectra for cyclic product 8.
FIG. 13 is the $^1$H NMR spectrum for cyclic product 9
FIG. 14 is the $^1$H and $^{13}$C NMR spectra for cyclic product 10.
FIG. 15 is the $^1$H and $^{13}$C NMR spectra for cyclic product 11.
FIG. 16 is the $^1$H and $^{13}$C NMR spectra for cyclic product 12.
FIG. 17 is the $^1$H and $^{13}$C NMR spectra for cyclic product 13.
FIG. 18 is the $^1$H and $^{13}$C NMR spectra for cyclic product 14.
FIG. 19 is the $^1$H and $^{13}$C NMR spectra for cyclic product 15.
FIG. 21 is the $^1$H and $^{13}$C NMR spectra for cyclic product 17.
FIG. 22 is the $^1$H and $^{13}$C NMR spectra for cyclic product 18.
FIG. 23 is the $^1$H and $^{13}$C NMR spectra for cyclic product 19.
FIG. 24 is the $^1$H and $^{13}$C NMR spectra for cyclic product 20.
FIG. 25 is the $^1$H and $^{13}$C NMR spectra for cyclic product 21.
FIG. 26 is the $^1$H and COSY NMR spectra for cyclic product 22.
FIG. 27 is the $^1$H NMR spectrum for cyclic product 23.
FIG. 28 depicts a crude LC-MS(ESI) analysis of HATU-mediated cyclization of Pro-Gly-Gly-Gly at 0.2M.
FIG. 29 depicts a crude LC-MS(ESI) analysis of isocyanide/amino aldehyde-mediated cyclization of Pro-Gly-Gly-Gly at 0.2M.
FIG. 30 shows the nucleophilic ring-opening of aziridine-containing cyclic peptides.
FIG. 31 depicts the pK$_a$'s of thiols and ammonium ions and ΔpK$_a$ of ion pairs.
FIG. 32 depicts a crude LC-MS(ESI) analysis for a reaction mixture of thiol opened product.

DETAILED DESCRIPTION

Figure 20:
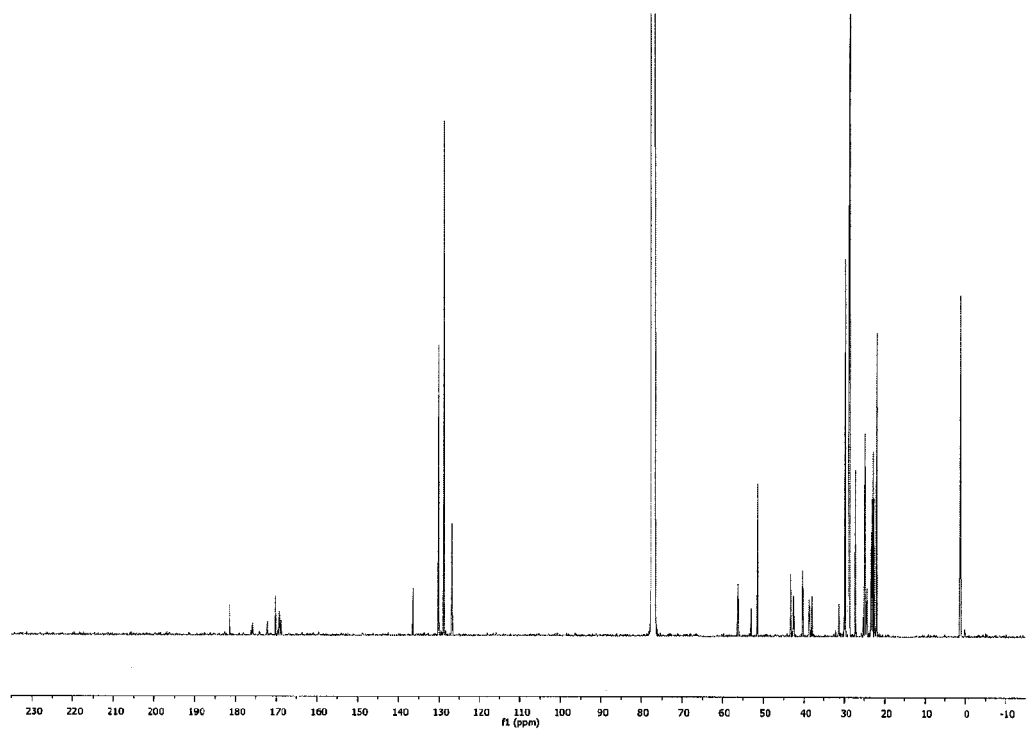
FIG. 20 is the $^1$H, COSY, and $^{13}$C NMR spectra for cyclic product 16.

There is described herein a one-step process that provides cyclic peptides in high yields and selectivities while evading the problems typically encountered during traditional cyclization reactions. The late stage diversification of macrocyclic molecules can now be achieved in a seamless fashion. The products of the macrocyclization are equipped with specific modification sites, which enable late-stage structural modification of cyclic peptides. The post cyclization diversification has been a historic challenge for macrocycle libraries in both biotechnology and pharmaceutical industries. The present macrocyclization approach solves this problem, among others.

There is demonstrated herein a use for a class of stable amphoteric amino aldehydes that contain synthetically useful unprotected aziridine and aldehyde groups.[8] Amphoteric amino aldehydes are coaxed into undergoing a reversible reaction with the amine and carboxyl ends of the peptide. The resulting electrophilic intermediate rapidly reacts with the nucleophilic aziridine portion due to the high effective molarity. As a result, the unfavorable chain/ring equilibrium is shifted using the Le Chatelier principle, securing efficient conversion to cyclic products. In another aspect, the cyclization tolerates aliphatic, acidic, and basic amino acid side chain residues. In particular, peptides, including those containing both acidic and basic residues, are found to be within the scope of this process, delivering a single diastereomeric product in each case. Trifluoroethanol ("TFE"), known for its capacity to stabilize peptide secondary structure and promote polar interactions,[9] is the preferred reaction medium. The Ugi four-component condensation, a well-known reaction involving carboxylic acids, amines, aldehydes, and isocyanides[10], is the preferred means of generating zwitterionic macrocyclization precursors. Mechanistically, the Ugi reaction is known to proceed through a series of reversible transformations that tend towards the thermodynamic driving force of amide bond formation. When an α-amino acid, aldehyde, and isocyanide are used as starting materials, the reaction traverses a zwitterionic iminium ion intermediate, which upon attack by the isocyanide produces an electrophilic mixed anhydride. Subsequent reaction with methanol gives a linear peptide ester as a mixture of diastereoisomers.[11] This reaction has been attempted in the synthesis of cyclic peptides from linear peptides and conventional (monofunctional) aldehydes. However, low yields are accompanied by lack of diastereoselectivity and dominant cyclodimerization products.[12,13]

In one aspect, there is provided a process to produce a cyclic amino acid molecule comprising reacting an amino acid molecule, having an amino terminus and a carboxyl terminus, with an isocyanide and a compound having formula (Ia) and/or (Ib):

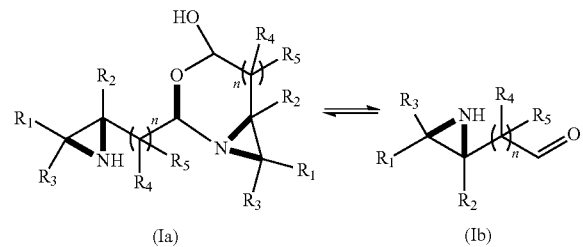

(Ia)  (Ib)

wherein:
n=0 or 1. and $R_1$, $R_2$, $R_3$, $R_4$ and $R_5$ are independently selected from H; lower alkyl; alkenyl; heterocycle; cyckoalkyl; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -lower alkyl-aryl, or —NR$_a$R$_b$, where R$_a$ and R$_b$ are independently selected from H, lower alkyl, aryl or -lower alkyl-aryl; —C(O)R$_c$, wherein R$_c$ is selected from lower alkyl, aryl or -lower alkyl-aryl; or -lower alkyl-OR$_d$, wherein R$_d$ is a suitable protecting group or OH group; all of which are optionally substituted at one or more substitutable positions with one or more suitable substituents; and the aldehyde component thereof may optionally be in its bisulfite adduct form;

and the amino acid molecule is an amino acid, a linear peptide or a salt of the foregoing, provided that if the amino acid molecule is a linear peptide, the compound comprises an aziridine chiral center proximal to the aldehyde with matching stereochemistry to the carbon atom proximal to the amino terminus of the peptide.

Preferably, if the amino acid molecule is an amino acid then the amino terminus is a primary amino group or a secondary amino group but wherein the amino acid molecule is a peptide, then the amino terminus is a secondary amino group.

In one embodiment, any one of $R_1$-$R_5$ is H. Preferably, n=0 and $R_2$ and $R_3$ is H or $R_1$-$R_3$ is H.

In a particular embodiment $R_1$ is CH$_2$OTBDMS or CH$_2^i$Pr.

In one embodiment, the amino acid molecule is a linear peptide. Preferably, the amino terminus amino acid of the linear peptide is selected from the group consisting of proline and an amino acid with an amino group substituted with NHBn, NHCH$_2$CH$_2$SO$_2$Ph or NHCH$_2$CH$_2$CN.

In another embodiment, the amino acid molecule is a D or L amino acid selected from the group consisting of alanine, arginine, asparagine, aspartic acid, cysteine, glutamic acid, glutamine, glycine, histidine, isoleucine, leucine, lysine, methionine, phenylalanine, proline, selenocysteine, serine, tyrosine, threonine, tryptophan and valine.

The amino acid molecule may be an alpha-amino acid, beta-amino acid or gamma-amino acid.

In one embodiment the isocyanide is selected from the group consisting of: (S)-(−)-α-Methylbenzyl isocyanide; 1,1,3,3,-Tetramethylbutyl isocyanide; 1-Pentyl isocyanide; 2,6-Dimethylphenyl isocyanide; 2-Morpholinoethyl isocyanide; 2-Naphthyl isocyanide; 2-Pentyl isocyanide; 4-Methoxyphenyl isocyanide; Benzyl isocyanide; Cutyl isocyanide; Cyclohexyl isocyanide; Isopropyl isocyanide; p-Toluenesulfonylmethyl isocyanide; Phenyl isocyanide dichloride; tert-Butyl isocyanide; (Trimethylsilyl)methyl isocyanide; 1H-Benzotriazol-1-ylmethyl isocyanide; 2-Chloro-6-methylphenyl isocyanide; Di-tert-butyl 2-isocyanosuccinate; tert-Butyl 2-isocyano-3-methylbutyrate; tert-Butyl 2-isocyano-3-phenylpropionate; tert-Butyl 2-isocyanopropionate; and tert-Butyl 3-isocyanopropionate, preferably, tert-Butyl isocyanide.

In some embodiments, the process is conducted in a non-nucleophilic reaction medium, preferably trifluoroethanol or HFIP mixed with water.

In one embodiment, if the amino acid molecule is an amino acid, the process is conducted in water.

In some embodiments, the process further comprises conjugating a fluorescent tag to the cyclic amino acid molecule by nucleophilic ring-opening of the aziridine moiety.

In some embodiments, the peptide is between 2 and 30 amino acids in length.

In another aspect, there is provided a cyclic amino acid molecule prepared using the process described herein.

One would understand that cyclization, in some cases, may require and would include protecting certain peptide or amino acid side chains in manner known to a person skilled in the art.

In another aspect, there is provided a cyclic amino acid molecule of formula (II):

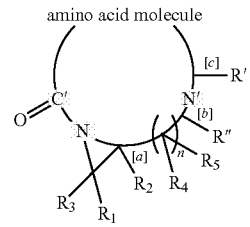

wherein,
n=0 or 1. and $R_1$, $R_2$, $R_3$, $R_4$ and $R_5$ are independently selected from H; lower alkyl; aryl; heteroaryl; alkenyl; heterocycle; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -loweralkyl-aryl, or NR$_a$R$_b$, where R$_a$ and R$_b$ are independently selected from H, lower alkyl, aryl or -loweralkyl-aryl; —C(O)R$_c$, wherein R$_c$ is selected from lower alkyl, aryl or -lower alkyl-aryl; or -lower alkyl-OR$_d$, wherein R$_d$ is a suitable protecting group or OH group; all of which are optionally substituted at one or more substitutable positions with one or more suitable substituents, bonds [a] and [b] are syn to each other;
R' is an amino acid side chain of the amino terminus amino acid;
R" is an optionally substituted amide;
and the amino acid molecule is an amino acid or a linear peptide, wherein N' is the nitrogen at the amino terminus end of the amino acid molecule and C' is the carbon at the carboxy terminus end of the amino acid molecule, and provided that if the amino acid molecule is a linear peptide, bonds [a] and [c] are anti to each other.

Preferably, if the amino acid molecule is an amino acid then the amino terminus is a primary amino group or a secondary amino group but wherein the amino acid molecule is a linear peptide, then the amino terminus is a secondary amino group.

In one embodiment, any one of $R_1$-$R_5$ is H. Preferably, n=0 and $R_2$ and $R_3$ is H or $R_1$-$R_3$ is H.

In a particular embodiment $R_1$ is $CH_2OTBDMS$ or $CH_2{}^iPr$.

In one embodiment, the amino acid molecule is a linear peptide. Preferably, the amino terminus amino acid of the linear peptide is selected from the group consisting of proline and an amino acid with an amino group substituted with $NHBn$, $NHCH_2CH_2SO_2Ph$ or $NHCH_2CH_2CN$.

In another embodiment, the amino acid molecule is a D or L amino acid selected from the group consisting of: alanine, arginine, asparagine, aspartic acid, cysteine, glutamic acid, glutamine, glycine, histidine, isoleucine, leucine, lysine, methionine, phenylalanine, proline, selenocysteine, serine, tyrosine, threonine, tryptophan and valine.

The amino acid molecule may be an alpha-amino acid, beta-amino acid or gamma-amino acid.

In one embodiment R" is tert-Butyl amide.

In another aspect, there is provided use of a compound for cyclizing an amino acid molecule, wherein the compound has the formula (Ia)/(Ib):

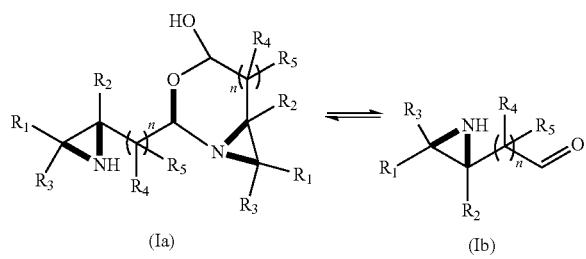

comprises an a-stereocenter at the carbon atom proximal to the aldehyde group with matching stereochemistry to the carbon atom proximal to the amino terminus of the amino acid molecule; and n=0 or 1, and $R_1$, $R_2$, $R_3$, $R_4$ and $R_5$ are independently selected from H; lower alkyl; aryl; heteroaryl; alkenyl; heterocycle; esters of the formula —C(O)OR* wherein R* is selected from alkyl and aryl; amides of the formula —C(O)NRR*, wherein R and R* are independently selected from alkyl and aryl; —$CH_2C(O)R$, wherein R is selected from —OH, lower alkyl, aryl, -loweralkyl-aryl, or —$NR_aR_b$, where $R_a$ and $R_b$ are independently selected from H, lower alkyl, aryl or -loweralkyl-aryl; —$C(O)R_c$, wherein $R_c$ is selected from lower alkyl, aryl or -loweralkyl-aryl; or -lower alkyl-$OR_d$, wherein $R_d$ is a suitable protecting group; all of which are optionally substituted at one or more substitutable positions with one or more suitable substituents; and the amino acid molecule is an amino acid, a linear peptide or a salt of the foregoing, provided that if the amino acid molecule is a linear peptide, the compound comprises an aziridine chiral center proximal to the aldehyde with matching stereochemistry to the carbon atom proximal to the amino terminus of the peptide.

As used herein, the term "amino acid molecule" is meant to include single amino acids and also peptides.

As used herein, the term "amino acid" refers to molecules containing an amine group, a carboxylic acid group and a side chain that varies. Amino acid is meant to include not only the twenty amino acids commonly found in proteins but also non-standard amino acids and unnatural amino acid derivatives known to those of skill in the art, and therefore includes, but is not limited to, alpha, beta and gamma amino acids. Peptides are polymers of at least two amino acids and may include standard, non-standard, and unnatural amino acids.

The term "suitable substituent" as used in the context of the present invention is meant to include independently H; hydroxyl; cyano; alkyl, such as lower alkyl, such as methyl, ethyl, propyl, n-butyl, t-butyl, hexyl and the like; alkoxy, such as lower alkoxy such as methoxy, ethoxy, and the like; aryloxy, such as phenoxy and the like; vinyl; alkenyl, such as hexenyl and the like; alkynyl; formyl; haloalkyl, such as lower haloalkyl which includes $CF_3$, $CCl_3$ and the like; halide; aryl, such as phenyl and napthyl; heteroaryl, such as thienyl and furanyl and the like; amide such as $C(O)NR_aR_b$, where $R_a$ and $R_b$ are independently selected from lower alkyl, aryl or benzyl, and the like; acyl, such as $C(O)$—$C_6H_5$, and the like; ester such as —$C(O)OCH_3$ the like; ethers and thioethers, such as O-Bn and the like; thioalkoxy; phosphino; and $NR_aR_b$, where $R_a$ and $R_b$ are independently selected from lower alkyl, aryl or benzyl, and the like. It is to be understood that a suitable substituent as used in the context of the present invention is meant to denote a substituent that does not interfere with the formation of the desired product by the processes of the present invention.

As used in the context of the present invention, the term "lower alkyl" as used herein either alone or in combination with another substituent means acyclic, straight or branched chain alkyl substituent containing from one to six carbons and includes for example, methyl, ethyl, 1-methylethyl, 1-methylpropyl, 2-methylpropyl, and the like. A similar use of the term is to be understood for "lower alkoxy", "lower thioalkyl", "lower alkenyl" and the like in respect of the number of carbon atoms. For example, "lower alkoxy" as used herein includes methoxy, ethoxy, t-butoxy.

The term "alkyl" encompasses lower alkyl, and also includes alkyl groups having more than six carbon atoms, such as, for example, acyclic, straight or branched chain alkyl substituents having seven to ten carbon atoms.

The term "aryl" as used herein, either alone or in combination with another substituent, means an aromatic monocyclic system or an aromatic polycyclic system. For example, the term "aryl" includes a phenyl or a napthyl ring, and may also include larger aromatic polycyclic systems, such as fluorescent (e.g. anthracene) or radioactive labels and their derivatives.

The term "heteroaryl" as used herein, either alone or in combination with another substituent means a 5, 6. or 7-membered unsaturated heterocycle containing from one to 4 heteroatoms selected from nitrogen, oxygen, and sulphur and which form an aromatic system. The term "heteroaryl" also includes a polycyclic aromatic system comprising a 5, 6. or 7-membered unsaturated heterocycle containing from one to 4 heteroatoms selected from nitrogen, oxygen, and sulphur.

The term "cycloalkyl" as used herein, either alone or in combination with another substituent, means a cycloalkyl substituent that includes for example, but is not limited to, cyclopropyl, cyclobutyl, cyclopentyl, cyclohexyl and cycloheptyl.

The term "cycloalkyl-alkyl-" as used herein means an alkyl radical to which a cycloalkyl radical is directly linked; and includes, but is not limited to, cyclopropylmethyl, cyclobutylmethyl, cyclopentylmethyl, 1-cyclopentylethyl, 2-cyclopentylethyl, cyclohexylmethyl, 1-cyclohexylethyl and 2-cyclohexylethyl. A similar use of the "alkyl" or "lower alkyl" terms is to be understood for aryl-alkyl-, aryl-loweralkyl- (e.g. benzyl), -lower alkyl-alkenyl (e.g. allyl), heteroaryl-alkyl-, and the like as used herein. For example, the term "aryl-alkyl-" means an alkyl radical, to which an aryl is bonded. Examples of aryl-alkyl- include, but are not limited to, benzyl (phenylmethyl), 1-phenylethyl, 2-phenylethyl and phenylpropyl.

As used herein, the term "heterocycle", either alone or in combination with another radical, means a monovalent radical derived by removal of a hydrogen from a three- to seven-membered saturated or unsaturated (including aromatic) heterocycle containing from one to four heteroatoms selected from nitrogen, oxygen and sulfur. Examples of such heterocycles include, but are not limited to, aziridine, epoxide, azetidine, pyrrolidine, tetrahydrofuran, thiazolidine, pyrrole, thiophene, hydantoin, diazepine, imidazole, isoxazole, thiazole, tetrazole, piperidine, piperazine, homopiperidine, homo-piperazine, 1,4-dioxane, 4-morpholine, 4-thiomorpholine, pyridine, pyridine-N-oxide or pyrimidine, and the like.

The term "alkenyl", as used herein, either alone or in combination with another radical, is intended to mean an unsaturated, acyclic straight chain radical containing two or more carbon atoms, at least two of which are bonded to each other by a double bond. Examples of such radicals include, but are not limited to, ethenyl (vinyl), 1-propenyl, 2-propenyl, and 1-butenyl.

The term "alkynyl", as used herein is intended to mean an unsaturated, acyclic straight chain radical containing two or more carbon atoms, at least two of which are bonded to each other by a triple bond. Examples of such radicals include, but are not limited to, ethynyl, 1-propynyl, 2-propynyl, and 1-butynyl.

The term "alkoxy" as used herein, either alone or in combination with another radical, means the radical —O—($C_{1-n}$)alkyl wherein alkyl is as defined above containing 1 or more carbon atoms, and includes for example methoxy, ethoxy, propoxy, 1-methylethoxy, butoxy and 1,1-dimethylethoxy. Where n is 1 to 6. the term "lower alkoxy" applies, as noted above, whereas the term "alkoxy" encompasses "lower alkoxy" as well as alkoxy groups where n is greater than 6 (for example, n=7 to 10). The term "aryloxy" as used herein alone or in combination with another radical means —O-aryl, wherein aryl is defined as noted above.

A peptide is a polymer of two or more amino acids.

The following examples are illustrative of various aspects of the invention, and do not limit the broad aspects of the invention as disclosed herein.

EXAMPLES

Example 1

Materials and Methods

Anhydrous toluene and dimethylformamide (DMF) were purchased and used as received. Tetrahydrofuran (THF) was distilled from sodium benzophenone ketyl under argon. All other solvents including TFE (2,2,2,-trifluoroethanol) and HFIP (1,1,1,3,3,3-hexafluoro-2-isopropanol) were of reagent grade quality. Melting points were obtained on a MelTemp melting-point apparatus and are uncorrected.

Method 1: amino acid/peptide cyclization reaction was conducted using the following method. In a screw-cap vial equipped with a magnetic stirring bar was added peptide (0.2 mmol) and 1 ml of TFE and stirred until a homogeneous solution has been obtained. Aziridine aldehyde dimer (0.1 mmol) and isocyanide (0.2 mmol) were then added sequentially and the resulting mixture was stirred for the time specified in Table 1. Reactions were monitored by electrospray ionization mass spectrometry ("ESI-MS") at 60 eV and/or thin layer chromatography ("TLC") analysis. After completion of the reaction, 1 ml of water and 1 ml of $Et_2O$ were added and the mixture was shaken vigorously and then cooled on ice. The resulting precipitate was filtered and washed with hexanes and cold $Et_2O$ (1 ml) to afford the cyclic peptide. For products that are water soluble or do not precipitate, the reaction mixture was concentrated under reduced pressure and then triturated with $Et_2O$ and hexanes (0.2 ml) to afford the cyclic peptide product.

Method 2: amino acid/peptide cyclization reaction was conducted using HFIP in place of TFE (Method 2). In a screw-cap vial equipped with a magnetic stirring bar was added peptide (0.2 mmol) and 1 ml of HFIP and stirred until homogeneous solution has been obtained. Aziridine aldehyde dimer (0.1 mmol) and isocyanide (0.2 mmol) were then added sequentially and the resulting mixture was stirred for the time specified in Table 1. Reactions were monitored by ESI-MS at 60 eV and/or TLC analysis. After completion of the reaction, the mixture was concentrated under reduced pressure and then triturated with $Et_2O$ and hexanes (0.2 ml) to afford the cyclic peptide product.

Method 3: amino acid/peptide cyclization reaction was carried out using HFIP and water. In a screw-cap vial equipped with a magnetic stirring bar was added peptide (0.2 mmol) and 1 ml of HFIP and 47 microliters of $H_2O$ and stirred until homogeneous. Aziridine aldehyde dimer (0.1 mmol) and isocyanide (0.2 mmol) were then added sequentially and the resulting mixture was stirred for the time specified in Table 1. Reactions were monitored by ESI-MS at 60 eV and/or TLC analysis. After completion of the reaction, the mixture was concentrated under reduced pressure and then triturated with $Et_2O$ and hexanes to afford the cyclic peptide product.

Note: In reactions involving either cysteine or peptides containing thiol residues, the solvent was degassed with argon for two hours prior to reaction. The reaction was thereafter carried out under an atmosphere of argon.

Some of the cyclic products that may be synthesized from each of Methods 1-3 are summarized in Table 3 and depicted in FIG. 4

TABLE 3

Methods used for amino acid/peptide cyclization reactions.

| Method | Cyclic Products |
|---|---|
| 1 | 1, 2, 3, 4, 7, 9, 11, 12, 15, 16, 17, 18, 19, 20, 21, 22 |
| 2 | 5, 8, 10, 13, 14 |
| 3 | 6 |

The relative stereochemistry of each cyclic product listed in Table 3 was established by correlating the methine region of each $^1$H NMR spectrum with that of piperazinone 1.

Chromatography: Flash column chromatography was carried out using Silicycle 230-400 mesh silica gel. Thin-layer chromatography (TLC) was performed on Macherey Nagel pre-coated glass backed TLC plates (SIL G/UV254, 0.25 mm) and visualized using a UV lamp (254 nm) and iodine stain.

Nuclear magnetic resonance spectra: $^1$H and $^{13}$C NMR spectra were recorded on Varian Mercury 400 or 500 MHz spectrometers. $^1$H NMR spectra were referenced to TMS (0 ppm) and $^{13}$C NMR spectra were referenced to CDCl3 (77.23 ppm). Peak multiplicities are designated by the following abbreviations: s, singlet; bs, broad singlet; d, doublet; t, triplet; q, quartet; m, multiplet; ds, doublet of singlets; dd, doublet of doublets; ddd, doublet of doublet of doublets; bt, broad triplet; td, triplet of doublets; tdd, triplet of doublets of doublets.

Mass Spectroscopy: High-resolution mass spectra were obtained on a VG 70-250S (double focusing) mass spectrometer at 70 eV or on an ABI/Sciex Qstar mass spectrometer with ESI source, MS/MS and accurate mass capabilities. Low resolution mass spectra (ESI) were obtained at 60 eV, 70 eV and 100 eV.

Synthetic routes toward aziridine aldehyde dimers: All dimeric amino aldehydes used in this study were prepared according to the synthetic route outlined in Supplementary FIGS. 1 and 2.

Results

Diverse piperazinones were produced in a one-step process (Table 1).

TABLE 1

The scope of piperazinone synthesis
(L-amino acid-derived product is shown).

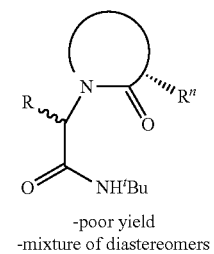

| Entry[a] | R[1] | Amino Acid | Time | Product[b] |
|---|---|---|---|---|
| 1 | CH$_2$OTBDMS | L-Phe | 1 | 1 (92) |
| 2 | CH$_2$OTBDMS | D-Phe | 1.5 | 2 (90) |
| 3 | CH$_2$OTBDMS | L-Ala | 1.5 | 3 (82) |
| 4 | CH$_2$OTBDMS | L-Pro | 1 | 4 (98) |
| 5 | CH$_2$$^i$Pr | D-Arg | 1 | 5 (83) |
| 6[c] | CH$_2$$^i$Pr | L-Lys HCl[g] | 1 | 6 (76) |
| 7 | CH$_2$OTBDMS | L-Gly | 1 | 7 (80) |
| 8[e] | CH$_2$$^i$Pr | L-Asp | 3 | 8 (76) |
| 9[f] | CH$_2$OTBDMS | L-Cys | 2 | 9 (82) |
| 10[d] | CH$_2$OTBDMS | L-His | 1 | 10 (88) |
| 11 | CH$_2$OTBDMS | L-Ser | 3 | 11 (77) |

[a]Unless specified otherwise, reactions were performed at room temperature using 0.2 mmol of isocyanide and amino acid, and 0.1 mmol of amino aldehyde dimer in TFE (0.2 M).
[b]% isolated yield.
[c]HFIP/H$_2$O (20:1) was used as solvent (0.2 M).
[d]HFIP was used as solvent (0.2 M).
[e]Cyclization occurs at the more acidic α-carboxylic acid.
[f]TFE was degassed prior to use.
[g]Lysine side chain amine is protonated.

The step that shifts the ring/chain equilibrium is transannular collapse of the nucleophilic NH aziridine onto the electrophilic mixed anhydride generated when an amphoteric amino aldehyde is subjected to the Ugi reaction condition (Scheme 2). The reaction takes place under stoichiometric conditions and delivers cyclic peptide product. High dilution, a critical condition normally required in order to achieve high yields in cyclic peptide synthesis, is not necessary.

Scheme 2.

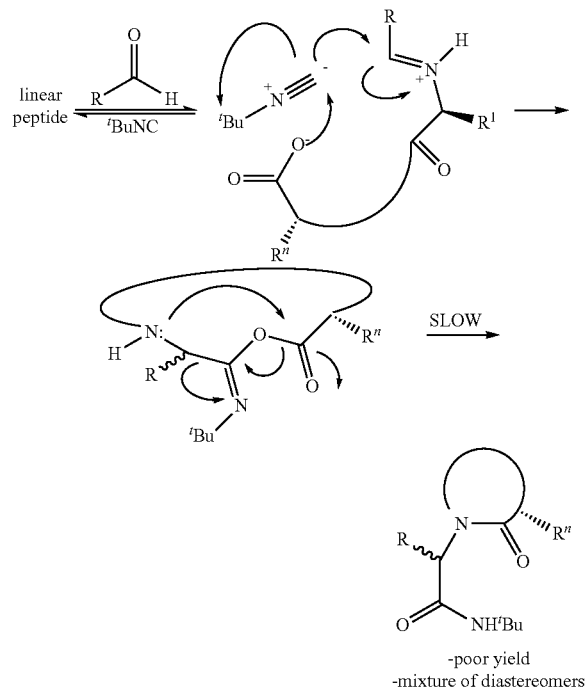

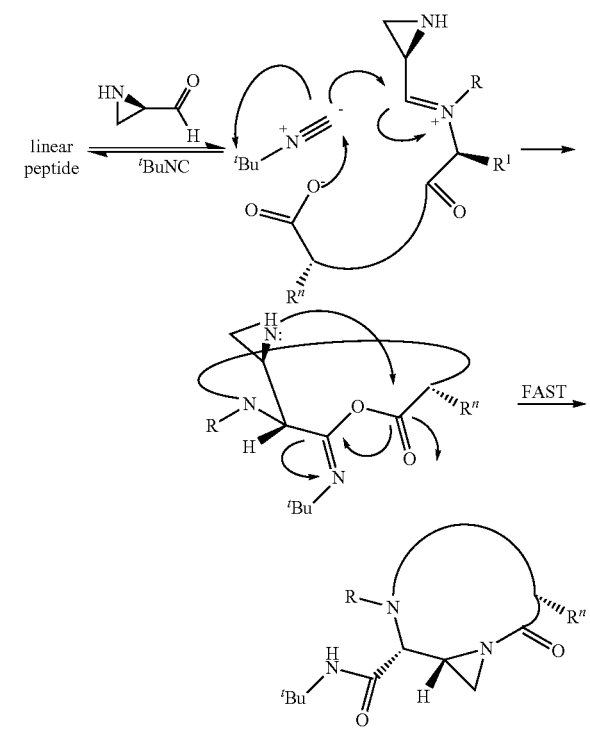

A. Macrocyclization with a monofunctional aldehyde;
B. macrocyclization mediated by an amphoteric amino aldehyde.

The normally challenging medium-sized rings can be made with great facility and in good yields within several hours (Table 2).

TABLE 2
Representative scope of linear peptide macrocyclization.
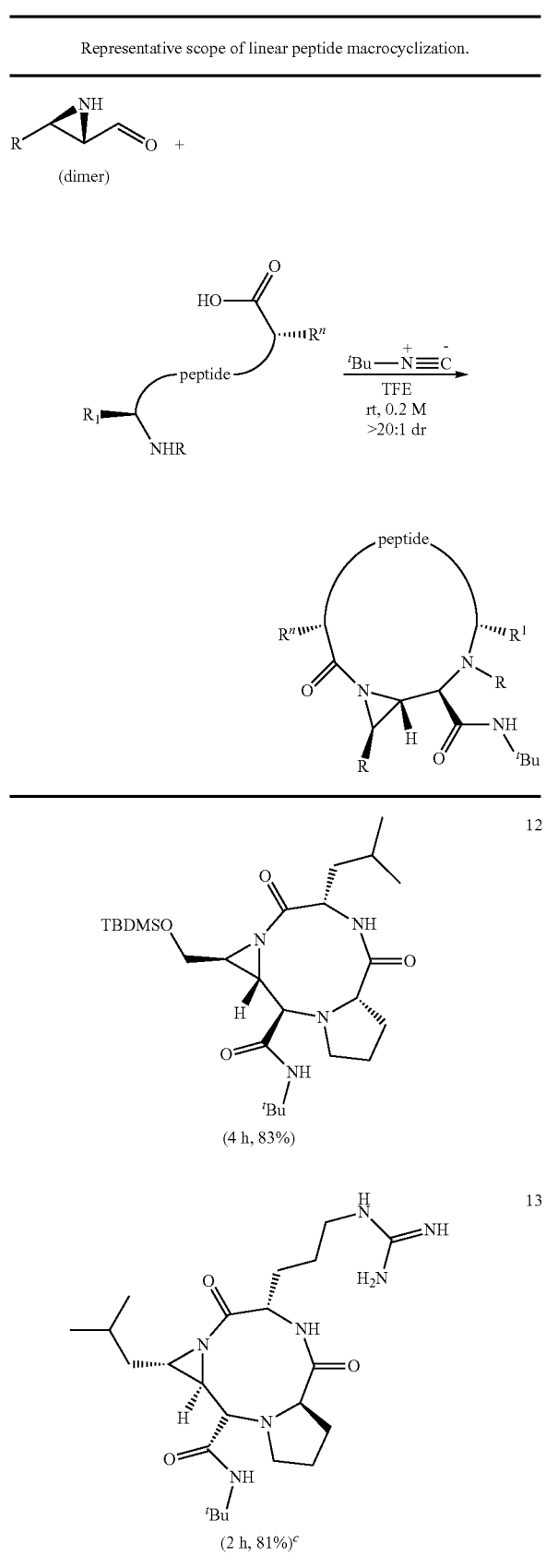
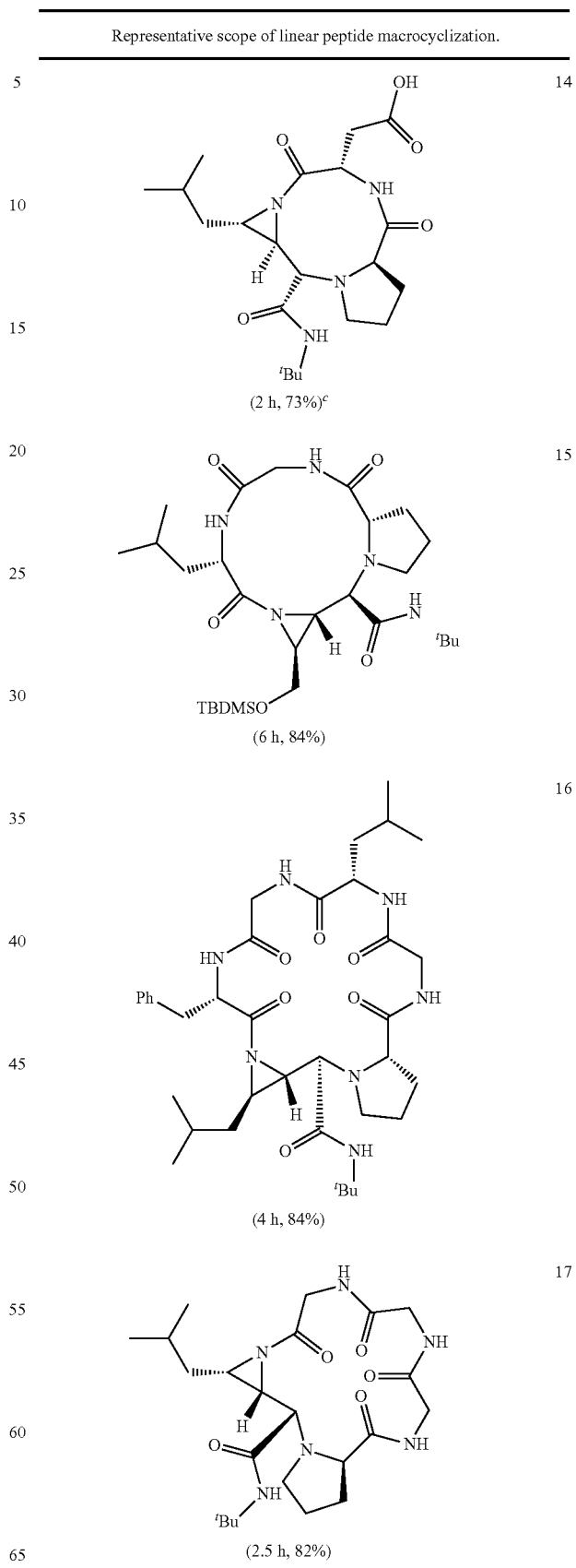

TABLE 2-continued

Representative scope of linear peptide macrocyclization.

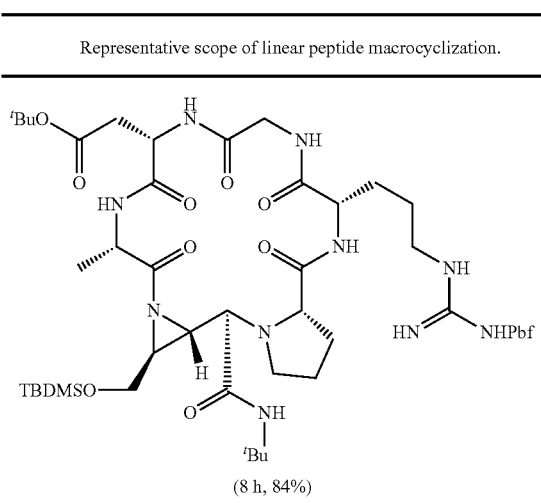

(8 h, 84%)

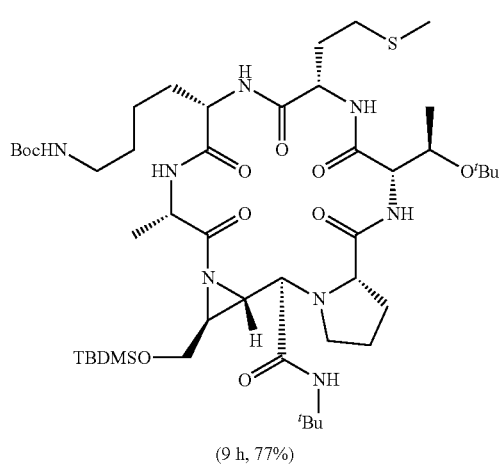

(9 h, 77%)

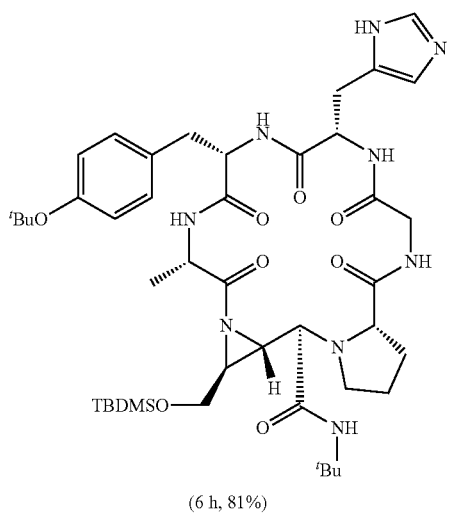 [SMILES: C[C@@H]1NC(=O)[C@H](Cc2ccc(OC(C)(C)C)cc2)NC(=O)[C@H](Cc2cnc[nH]2)NC(=O)CNC(=O)[C@@H]2CCCN2[C@@H](C(=O)NC(C)(C)C)[C@@H]2[C@@H](CO[Si](C)(C)C(C)(C)C)N2C1=O ; "(6 h, 81%)"]

(6 h, 81%)

TABLE 2-continued

Representative scope of linear peptide macrocyclization.

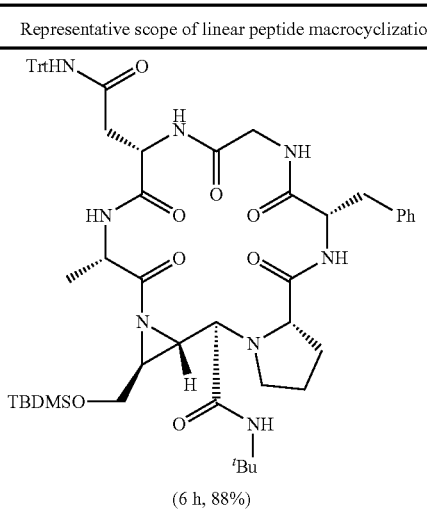

(6 h, 88%)

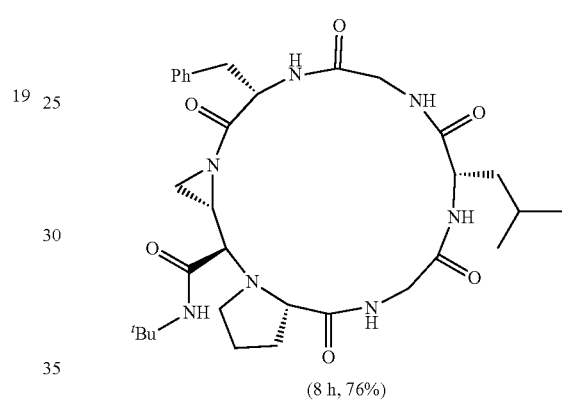

(8 h, 76%)

[a] Unless specified otherwise, reactions were performed at room temperature using 0.2 mmol of isocyanide and amino acid, and 0.1 mmol of amino aldehyde dimer in TFE (0.2 M).
[b] Isolated yield.
[c] Diastereoselectivity of >20:1 was confirmed by $^1$H NMR analysis of each crude reaction mixture. The relative stereochemistry was established by correlating the methine region of each $^1$H NMR spectrum with that of piperazinone 1 (see X-ray crystal structure of 1).
[d] HFIP was used as solvent (0.2 M).

$^1$H and $^{13}$C NMR spectra for the cyclic products of Table 3 are shown in FIGS. 5-27.

A one-step process for making versatile cyclic peptides with high stereo- and chemoselectivity for linear peptides, isocyanides, and amphoteric amino aldehydes is provided. The Ugi reaction is run with an amphoteric amino aldehyde in place of a monofunctional aldehyde. When L-phenyl alanine was reacted with tert-butyl isocyanide, and an aziridine aldehyde, a cyclic piperazinone was obtained in 92% yield in approximately one hour (Table 1. Entry 1). The relative stereochemistry of 1 was established using X-ray analysis. A range of amino acids were subjected to this reaction and in all cases the corresponding piperazinone products were obtained as single diastereoisomers without formation of linear peptides (FIG. 1).

The existence of epimeric products were investigated through the use of $^1$H NMR (DMSO-d$_6$ or CDCl$_3$) analysis of crude reaction mixtures. In all of the reactions studied, there were no detectable signals corresponding to the epimer. As such, the resulting crude cyclic peptides were obtained in >20:1 selectivity.

The effect of medium-sized peptide chain length on the reaction outcome was studied (Table 2). The challenging medium-sized rings are readily prepared; the reaction times are less than 10 hours, proceeding with high yields and diastereoselectivities. The preferred work-up procedure involves product precipitation from diethyl ether and hexanes. The cyclic peptides require no further purification by HPLC. In addition, racemization was not detected throughout the course of the reaction or during product isolation. The lack of epimerization is further evidenced by high stereoselectivity; aziridine aldehydes with S stereocenters next to the carbonyl group undergo macrocyclization with the peptides that contain an L-amino acid residue at the N-terminus. The "mismatched" reaction with the D-amino acid-terminated peptide is unproductive, leading to the formation of stable aminals.

It has been determined that the α-stereocenter of the N-terminal amino acid, in this case proline, should match the α-stereocenter of the aziridine aldehyde in order for cyclization to occur, with respect to peptides. In a mismatched reaction, the only product formed is the corresponding aminal (FIG. 2). Even after an extended reaction time and additional equivalents of isocyanide, cyclic peptide formation was not observed. This restriction is not present for cyclization of single amino acids.

When the opposite enantiomer of amino aldehyde was used in the same reaction, the proline and the amino aldehyde both had S-configuration at their α-stereocenters. This matched case readily underwent peptide cyclization to yield the corresponding cyclic product in high yield (FIG. 3).

This stereoselectivity process is significant in the context of possible epimerization at the N-terminus. Since matched stereochemistry is required for the cyclization to occur, the resulting cyclic peptides will necessarily contain matching stereocenters. Furthermore, the fact that no cyclic peptide formation was observed in mismatched reactions suggests that no epimerization, which would result in matched substrates, occurs under our macro conditions.

Consistent yields in this chemistry are likely obtained due to the mechanism that governs cyclization. It is at this point that a departure from the Ugi reaction with monofunctional aldehydes becomes apparent. When monofunctional aldehydes are used in the reaction with isocyanides and peptides, low diastereoselectivities are observed. More importantly, the undesired cyclodimerization occurs during the cyclization of linear peptides containing less than six residues; the cyclization of tripeptides yields only the cyclodimers.[13] This low selectivity is due to a slow transannular attack of the amine onto the mixed anhydride (Scheme 2. A), thus allowing the intermolecular process to be kinetically competitive. By adding an amphoteric amino aldehyde to the cyclization reaction mixture containing a secondary amine-terminated peptide, the slow transannular attack is being replaced with a fast attack by the nucleophilic aziridine, which is positioned exocyclic to the mixed anhydride (Scheme 2. B). This provides an unencumbered trajectory of attack. Since TFE is a non-nucleophilic solvent, premature solvolysis of the mixed anhydride is not observed. The reaction mechanism ensures that the C-terminus is activated only upon formation of the intermediate cyclic mixed anhydride, which is then attacked by the exocyclic aziridine. This not only secures selectivity for the intramolecular macrocyclization, but also avoids prolonged C-terminus activation and potential epimerization. Accordingly, high dilution, a critical condition normally required in order to achieve high yields in conventional cyclic peptide synthesis, is not necessary.[6] Furthermore, no oligomeric or polymeric by-products were detected in the subject experiments. A side-by side comparison of the subject reaction with the traditional lactamization of a linear tetrapeptide, widely used in the synthesis of cyclic peptides, was conducted. The amino aldehyde mediated macrocyclization delivered rapid, selective, and efficient formation of the cyclic peptide. In contrast, only trace amount of the cyclic peptide was detected among myriad structures formed in the course of the lactamization. The undesired cyclodimerization[5] has dominated this process, which is a testament to sluggish kinetics of the conventional intramolecular process. Peptide macrocyclization reactions are normally performed under extremely dilution. Typical protocols necessitate molar concentrations of $10^{-4}$ M. This large dilution increases the selectivity for intramolecular cyclizations, thereby limiting undesired cyclodimerization and trimerization.

Characterization of the relative stereochemistry of each cyclic product listed in Table 3 is set out below.

(3S,5R,6R,7S)-3-benzyl-N-tert-butyl-7-((tert-butyldimethylsilyloxy)methyl)-2-oxo-1,4-diazabicyclo [4.1.0]heptane-5-carboxamide (1)

$^1$H NMR (CDCl$_3$, 400 MHz) δ: 7.36-7.18 (m, 5H), 6.75 (bs, 1H), 3.86 (dd, J=11.6 Hz, 4.8 Hz, 1H), 3.74 (dd, J=11.2 Hz, 4.8 Hz, 1H), 3.54 (bs, 1H), 3.47 (dd, J=3.6 Hz, 1.2 Hz, 1H), 3.25 (dd, J=14.4 Hz, 3.2 Hz, 1H), 3.10 (m, 1H), 2.52 (dd, J=14.4 Hz, 10.4 Hz, 1H), 2.40 (m, 1H), 1.80 (bs, 1H), 1.02 (s, 9H), 0.90 (s, 9H), 0.10 (s, 3H), 0.08 (s, 3H) ppm. $^{13}$C NMR (CDCl$_3$, 100 MHz) δ: 184.8, 169.0, 138.5, 129.7, 128.9, 127.0, 63.9, 57.5, 53.6, 50.7, 44.6, 39.0, 35.5, 28.5, 26.1, 18.6, −5.0 ppm. HRMS (ESI) [MH]$^+$ calcd. 446.2833. found 446.2831

(3R,5R,6R,7S)-3-benzyl-N-tert-butyl-7-((tert-butyldimethylsilyloxy)methyl)-2-oxo-1,4-diazabicyclo [4.1.0]heptane-5-carboxamide (2)

$^1$H NMR (CDCl$_3$, 400 MHz) δ: 7.35-7.20 (m, 5H), 6.32 (bs, 1H), 3.86 (m, 1H),3.73 (dd, J=11.5 Hz, 4.2 Hz, 1H), 3.86 (bs, 1H), 3.73 (dd, J=11.5 Hz, 4.2 Hz, 1H), 3.25 (dd, J=14.4 Hz, 3.2 Hz, 1H), 3.10 (m, 1H), 2.52 (dd, J=14.4 Hz, 10.4 Hz, 1H), 2.40 (m, 1H), 1.80 (bs, 1H), 1.31 (s, 9H), 0.90 (s, 9H), 0.10 (s, 3H), 0.08 (s, 3H) ppm. $^{13}$C NMR (CDCl$_3$, 75 MHz) δ: 184.0, 169.1, 136.2, 129.2, 129.1, 127.3, 63.0, 59.5, 51.4, 49.6, 42.2, 38.7, 36.0, 28.8, 26.1, 18.7, −5.1 ppm. MS (ESI) [MH]$^+$ calcd. 446.3. found 446.3

(3S,5R,6R,7S)-N-tert-butyl-7-((tert-butyldimethylsilyloxy)methyl)-3-methyl-2-oxo-1,4-diazabicyclo [4.1.0]heptane-5-carboxamide (3)

$^1$H NMR (CDCl$_3$, 400 MHz) δ: 7.42 (s, NH), 3.88 (dd, J=11.2 Hz, 4.8 Hz, 1H),3.70 (dd, J=11.2 Hz, 5.2 Hz, 1H), 3.55 (d, J=0.8 Hz, 1H), 3.46 (dd, J=3.6 Hz, 1.6 Hz, 1H), 3.07 (m, 1H), 2.36 (td, J=4.8 Hz, 3.6 Hz, 1H), 1.8 (bs, NH), 1.39 (s, 9H), 1.23 (d, J=6.8 Hz, 3H), 0.90 (s, 9H), 0.09 (s, 3H), 0.08 (s, 3H) ppm. $^{13}$C NMR (CDCl$_3$,100 MHz) δ; 185.5, 169.3, 63.9, 53.8, 51.2, 51.0, 44.5, 39.3, 28.9, 26.1, 16.6, 15.0, −5.0 ppm. HRMS (ESI) [MH]$^+$ calcd. 370.2520. found 370.2520

(1S,3aS,8R,8aS)-N-tert-butyl-1-((tert-butyldimethylsilyloxy)methyl)-3-oxooctahydroazirino [1,2-a] pyrrolo[1,2-d]pyrazine-8-carboxamide (4)

$^1$H NMR (CDCl$_3$, 400 MHz) δ: 6.17 (s, 1H), 3.76 (dd, J=11.6 Hz, 4.4 Hz, 1H), 3.67 (dd, J=11.6 Hz, 4.8 Hz, 1H), 3.70 (d, J=6.2 Hz, 1H), 3.12 (dt, J=4.8 Hz, 9.2 Hz, 1H), 2.97 (dd, J=6.4 Hz, 3.6 Hz, 1H), 2.93-2.89 (m, 1H), 2.60 (q, J=4.4 Hz, 1H), 2.25-2.05 (m, 2H), 1.90-1.75 (m, 3H), 1.70-1.51 (m, 1H), 1.48 (s, 9H), 0.85 (s, 9H), 0.09 (s, 3H), 0.08 (s, 3H) ppm. $^{13}$C NMR (CDCl$_3$, 100 MHz) δ: 183.0, 168.6, 65.0, 63.4, 63.2, 54.6, 51.3, 43.4, 41.0, 29.0, 26.1, 22.2, 22.0, 18.9, −5.1 ppm. HRMS (ESI) [MH]$^+$ calcd. 396.2676. found 396.2656

(3R,5S,6S,7S)-N-tert-butyl-3-(3-guanidinopropyl)-7-isobutyl-2-oxo-1,4 diazabicyclo[4.1.0]heptane-5-carboxamide (5)

$^1$H NMR (D$_2$O, 400 MHz) δ: 3.59 (t, J=5.6 Hz, 1H), 3.46 (m, 1H), 3.13 (m, 1H), 2.94 (m, 1H), 3.37 (m, 1H), 1.78-1.44 (m, 8H), 1.22 (s, 9H), 0.83 (d, J=2.8 Hz,3H), 0.81 (d, J=2.8 Hz, 3H) ppm. $^{13}$H NMR (D$_2$O, 400 MHz) δ: 186.7, 172.0, 156.9, 54.9, 54.5, 54.0, 44.5, 42.8, 28.7, 27.9, 26.5, 25.7, 25.0, 24.1, 22.2, 21.5 ppm. MS (ESI) [MH]$^+$ calcd. 367.3. found 367.2 and 184.1 for [M+2H]$^{2+}$/2.

(3S,5S,6S,7S)-3-(4-aminobutyl)-N-tert-butyl-7-isobutyl-2-oxo-1,4-diazabicyclo[4.1.0]heptane-5-carboxamide (6)

NMR (D$_2$O with 10% v/v CD$_3$COOD, 400 MHz) δ: 5.14 (ddd, J=9.6 Hz, 4.4 Hz, 2.4 Hz, 1H), 4.12 (d, J=2.4 Hz, 1H), 3.07 (dd, J=7.6 Hz, 4.4 Hz, 1H), 2.85 (t, J=7.6 Hz, 2H), 1.82-1.46 (m, 10H), 1.32 (s, 9H), 0.83 (d, J=6.8 Hz, 3H), 0.81 (d, J=6.8 Hz, 3H) ppm. $^{13}$C NMR (D$_2$O with 10% v/v CD$_3$COOD, 100 MHz) δ: 178.0, 173.8, 97.2, 58.6, 54.5, 53.0, 40.6, 39.3, 29.3, 27.8, 27.6, 27.2, 26.8, 24.6, 22.2, 21.9, 20.8 ppm. MS (ESI) [MH]$^+$ calcd. 339.3. found 339.2 and 170.1 for [M+2H]$^{2+}$/2

(5R,6R,7S)-N-tert-butyl-7-((tert-butyldimethylsilyloxy)methyl)-2-oxo-1,4-diazabicyclo[4.1.0]heptane-5-carboxamide (7)

$^1$H NMR (400 MHz, CDCl$_3$) δ: 6.98 (s, 1H), 3.87 (dd, J=11.5, 4.5 Hz, 1H), 3.78 (dd, J=11.5, 4.5 Hz, 1H), 3.34-3.24 (m, 2H), 3.13 (d, J=4.6 Hz, 1H), 2.40 (td, J=4.5, 3.4 Hz, 1H), 2.17-1.96 (m, 1H), 1.43-1.36 (m, 9H), 0.94-0.86 (m, 9H), 0.13-0.05 (m, 6H). $^{13}$C NMR (101 MHz, CDCl$_3$) δ: 183.93, 168.37, 77.48, 77.16, 76.84, 63.02, 55.81, 51.25, 48.72, 45.27, 39.64, 28.87, 26.06, 18.55, 0.15, −5.09, −5.12.

2-((3S,5R,6R,7R)-5-(tert-butylcarbamoyl)-7-isobutyl-2-oxo-1,4-diazabicyclo[4.1.0]heptan-3-yl)acetic acid (8)

$^1$H NMR (400 MHz, CD$_3$OD) δ: 4.69-4.58 (m, 1H), 3.92 (d, J=2.0 Hz, 1H),3.76 (dd, J=9.8, 3.6 Hz, 1H), 3.66 (dd, J=7.8, 4.0 Hz, 1H), 2.90 (dd, J=17.5, 3.6 Hz, 1H), 2.81 (dd, J=16.7, 4.0 Hz, 1H), 2.69-2.53 (m, 2H), 1.36-1.32 (m, 9H), 0.98 (dt, J=8.5, 4.2 Hz, 6H). $^{13}$C NMR (101 MHz, CD$_3$OD) δ 188.21, 172.40, 158.66, 158.62, 56.05, 55.25, 55.23, 51.95, 44.17, 43.55, 43.35, 42.55, 42.39, 42.16, 41.98, 29.85, 28.90, 28.85, 28.10, 27.37, 27.16, 26.85, 26.51, 23.19, 22.63, 21.05.

(3R,5R,6R,7S)-N-(tert-butyl)-7-(((tert-butyldimethylsilyl)oxy)methyl)-3-(mercaptomethyl)-2-oxo-1,4-diazabicyclo[4.1.0]heptane-5-carboxamide (9)

Note: proper spectroscopic characterization of this compound is difficult as spectra are characterized by extremely broad peaks. This is attributed to inherent instability of 9 due to the presence of nucleophilic thiol and its susceptibility to oxidation and aziridine ring-opening.

$^1$H NMR (CDCl$_3$, 400 MHz) δ: 3.47 (s, 1H), 3.41 (d, J=6.5 Hz,1H), 4.35-2.42 (m, 7H), 1.70-1.42 (bs, 10H), 0.90 (s, 9H), 0.10 (s, 3H), 0.08 (s, 3H) ppm. MS (ESI) [MH]$^+$ calcd. 402.6. found 402.2

(3S,5R,6R,7S)-3-((1H-imidazol-4-yl)methyl)-N-(tert-butyl)-7-(((tert-butyldimethylsilyl)oxy)methyl)-2-oxo-1,4-diazabicyclo[4.1.0]heptane-5-carboxamide (10)

$^1$H NMR (CDCl$_3$, 400 MHz) δ: 7.56 (s, 1H), 7.25 (s, 1H), 6.87 (s, 1H), 6.22 (s, 1H), 4.46 (m, 1H), 3.72 (dd, J=11.2 Hz, 4.8 Hz, 1H), 3.60 (m, 1H), 3.44 (dd, J=3.6 Hz, 1.5 Hz, 1H), 3.27 (dd, J=14.1 Hz, 3.1 Hz, 1H), 2.99 (dd, J=14.7 Hz, 4.2 Hz, 1H), 2.80 (dd, J=15.2 Hz, 8.1 Hz, 1H), 2.40 (m, 1H), 2.05 (bs, 1H), 1.36 (s, 9H), 0.87 (s, 9H), 0.07 (s, 3H), 0.05 (s, 3H) ppm. $^{13}$C NMR (CDCl$_3$, 100 MHz) δ: 185.4, 171.4, 169.5, 168.6, 135.1, 64.3, 62.7, 60.6, 54.7, 51.2, 44.5, 39.3, 28.9, 26.0, 18.4, −5.3 ppm. MS (ESI) [MH]$^+$ calcd. 436.6. found 436.2

(3S,5R,6R,7S)-N-(tert-butyl)-7-(((tert-butyldimethylsilyl)oxy)methyl)-3-(hydroxymethyl)-2-oxo-1,4-diazabicyclo[4.1.0]heptane-5-carboxamide (11)

$^1$H NMR (CDCl$_3$, 400 MHz) δ: 6.80 (bs, 1H), 6.15 (bs, 1H), 4.02 (d, J=11.6 Hz, 1H), 3.85 (dd, J=13.3 Hz, 6.7 Hz, 1H), 3.76 (dd, J=14.2 Hz, 3.0 Hz, 1H), 3.68 (bs, 1H), 3.53 (d, J=5.0 Hz, 1H), 3.45 (dd, J=3.5 Hz, 2.4 Hz, 1H), 3.13 (m, 1H), 2.55 (m, 1H), 2.42 (m, 1H), 1.39 (s, 9H), 0.90 (s, 9H), 0.10 (s, 3H), 0.08 (s, 3H) ppm. $^{13}$C NMR (CDCl$_3$, 100 MHz) δ: 185.3, 168.9, 63.5, 61.4, 55.8, 53.9, 51.2, 44.9, 39.6, 28.9, 26.1, 18.6, −5.1 ppm. MS (ESI) [MH]$^+$ calcd. 386.6. found 386.2

(1S,4S,6aS,11R,11aS)-N-tert-butyl-1-((tert-butyldimethylsilyloxy)methyl)-4-isobutyl-3,6-dioxodecahydro-1H-azirino[1,2-a]pyrrolo[1,2-d][1,4,7]triazonine-11-carboxamide (12)

$^1$H NMR (CD$_3$OD, 400 MHz) δ: 4.47 (m, 1H), 4.14 (dd, J=8.4 Hz, 6 Hz, 1H), 4.07-3.99 (m, 2H), 3.84 (dd, J=12 Hz, 3.2 Hz, 1H), 3.32 (d, J=5.6 Hz, 1H), 3.26-3.15 (m, 2H), 2.42-2.30 (m, 2H), 1.92-1.78 (m, 3H), 1.74 (q, J=6.8 Hz, 2H), 1.59 (sept, J=6.8 Hz, 1H), 1.22 (s, 9H), 0.90 (d, J=6.8 Hz, 3H), 0.87 (d, J=6.4 Hz, 3H), 0.84 (s, 9H), 0.06 (s, 3H), 0.03 (s, 3H) ppm. $^{13}$C NMR (CD$_3$OD, 100 MHz) δ: 174.1, 164.1, 157.4, 86.5, 62.4, 60.7, 60.6, 57.7, 54.2, 52.1, 50.2, 39.6, 29.0, 25.8, 25.2, 25.1, 22.1, 21.0, 20.5, 17.9, −6.5 ppm. MS (ESI) calcd. 509.3. found 509.3

(1S,4S,6aR,11S,11aR)-N-tert-butyl-4-(3-guanidinopropyl)-1-isobutyl-3,6-dioxodecahydro-1H-azirino[1,2-a]pyrrolo[1,2-d][1,4,7]triazonine-11-carboxamide (13)

$^1$H NMR (CD$_3$OD, 400 MHz) δ: 4.26 (t, J=5.6 Hz, 1H), 4.18 (dd, J=8.8 Hz, 2.4 Hz, 1H), 3.58 (dd, J=8.8 Hz, 5.2 Hz, 1H), 3.28-3.24 (m, 2H), 3.00 (d, J=5.6 Hz, 1H), 2.70 (dd, J=10.4 Hz, 6.4 Hz, 1H), 2.32-2.18 (m, 2H), 1.98-1.52 (m, 11H), 1.28 (s, 9H), 1.01 (d, J=6.4 Hz, 3H), 0.96 (d, J=6.4 Hz, 3H) ppm. $^{13}$C NMR (CD$_3$OD, 100 MHz) δ: 178.0, 160.8, 159.1, 157.4, 86.9, 64.3, 63.5, 60.2, 54.5, 53.7, 51.0, 42.6, 41.4, 29.4, 28.8, 26.1, 24.9, 24.5, 22.7, 21.3, 20.4 ppm. MS(ESI) [MH]$^+$ calcd. 464.3. found 464.3 and 232.6 for [M+2H]$^{2+}$/2

2-((1S,4S,6aR,11S,11aR)-11-(tert-butylcarbamoyl)-1-isobutyl-3,6-dioxodecahydro-1H-azirino[1,2-a]pyrrolo[1,2-d][1,4,7]triazonin-4-yl)acetic acid (14)

$^1$H NMR (CD$_3$OD, 400 MHz) δ: 4.46 (t, J=9.2 Hz, 1H), 4.34 (dd, J=8.4 Hz, 2.0 Hz, 1H), 3.81 (dd, J=8.4 Hz, 5.6 Hz, 1H), 3.38-3.30 (m, 1H), 3.02 (dd, J=17.2 Hz, 2.4 Hz, 1H), 2.85-2.73 (m, 1H), 2.57 (dd, J=17.2 Hz, 8.4 Hz, 1H), 2.45-2.32 (m, 2H), 2.05-1.62 (m, 7H), 1.58-1.48 (m, 2H), 1.27 (s, 9H), 1.01 (d, J=6.4 Hz, 3H), 0.98 (d, J=6.4 Hz, 3H) ppm. MS (ESI) [MH]$^+$ calcd. 423.3. found 423.2

(1S,4S,9aS,14R,14aS)-N-tert-butyl-1-((tert-butyldimethylsilyloxy)methyl)-4-isobutyl-3,6,9-trioxotetradecahydroazirino[1,2-a]pyrrolo[1,2-d][1,4,7,10]tetraazacyclododecine-14-carboxamide (15)

$^1$H NMR (CD$_3$OD, 400 MHz) δ: 4.55 (ddd, J=8 Hz, 3.2 Hz, 1.6 Hz, 1H), 4.32 (dd, J=10.4 Hz, 4 Hz, 1H), 4.21 (dd, J=14 Hz, 6 Hz, 1H), 4.15-4.05 (m, 3H), 3.91 (dd, J=12 Hz, 3.2 Hz, 1H), 3.41 Hz (dd, J=6 Hz, 1H), 3.36-3.28 (m, 1H), 2.50-2.30 (m, 2H), 2.00-1.50 (m, 7H), 1.31 (s, 9 H), 0.98-0.92 (m, 6H), 0.92 (s, 9H), 0.13 (s, 3H), 0.11 (s, 3H) ppm. $^{13}$C NMR (CD$_3$OD, 100 MHz) δ: 178.3, 166.4, 165.1, 157.6, 86.7, 62.7, 61.0, 60.1, 54.2, 53.7, 52.6, 50.5, 44.0, 41.6, 28.9, 25.6, 25.2, 25.1, 25.1, 22.6, 20.7, 20.5, 17.9, –6.5, –6.5 ppm. MS (ESI) [MH]$^+$ calcd. 566.4. found 566.4

(1R,1aS,2R,6aS,12S,18S)-18-benzyl-N-tert-butyl-1,12-diisobutyl-7,10,13,16,19-pentaoxoicosahydroazirino[1,2-a]pyrrolo[1,2-d][1,4,7,10,13,16]hexaazacyclooctadecine-2-carboxamide (16)

$^1$H NMR (CDCl$_3$, 500 MHz) δ: 7.82 (bs, NH), 7.40-7.20 (m, 5H), 7.18 (bs, NH), 7.05 (bs, NH), 6.81 (bs, 2 NH), 4.64 (q, J=6.8 Hz, 1H), 4.13 (dd, J=16 Hz, 7.6 Hz, 1H), 4.10-3.90 (m, 2H), 3.57 (dd, J=16 Hz, 4.8 Hz, 1H), 3.50-3.39 (m, 2H), 3.26 (dd, J=14 Hz, 5.6 Hz, 1H), 3.12 (dd, J=14 Hz, 7.2 Hz, 1H), 3.12-3.08 (m, 1H), 3.00-2.92 (m, 2H), 2.63 (t, J=3.6 Hz, 1H), 2.28-2.18 (m, 1H), 1.90-1.70 (m, 2H), 1.37-1.25 (m, 9H), 1.10-0.88 (m, 12H) ppm. $^{13}$C NMR (CDCl$_3$, 125 MHz) δ: 181.4, 176.1, 175.7, 172.1, 170.1, 169.2, 136.4, 130.1, 128.7, 126.8, 56.2, 63.0, 43.2, 42.5, 40.2, 38.6, 37.9, 31.2, 30.0, 29.8, 29.5, 28.8, 28.7, 27.2, 25.1, 24.9, 24.3, 23.3, 23.1, 22.8, 22.7, 22.6, 22.4, 22.3, 21.9. MS (ESI) [MH]$^+$ calcd. 682.4. found 682.4

(1S,12aS,17R,17aR)-N-tert-butyl-1-isobutyl-3,6,9,12-tetraoxohexadecahydro-1H-azirino[1,2-a]pyrrolo[1,2-d][1,4,7,10,13]pentaazacyclopentadecine-17-carboxamide (17)

$^1$H NMR (400 MHz, CDCl$_3$) δ: 4.57-4.44 (m, 1H), 4.32-3.70 (m, 10H), 3.38 (d,J=5.4 Hz, 1H), 3.28 (s, 1H), 3.14 (dd, J=11.2, 5.6 Hz, 1H), 2.52-2.41 (m, 1H), 2.37 (d, J=6.9 Hz, 1H), 2.15-1.65 (m, 8H), 1.64-1.48 (m, 2H), 1.42-1.23 (m, 8H), 1.00 (dt, J=21.4, 7.4 Hz, 6H).
$^{13}$C NMR (100 MHz, CD$_3$OD) δ: 176.18, 171.23, 168.97, 165.90, 159.24, 86.37, 65.77, 63.49, 61.48, 59.76, 55.41, 51.43, 47.38, 45.65, 45.23, 44.59, 44.43, 44.19, 43.41, 42.46, 29.85, 29.43, 28.97, 28.58, 28.46, 27.72, 27.13, 26.74, 25.68, 23.84, 23.68, 23.14, 23.06, 22.16, 21.62.

tert-butyl 2-((1S,4S,7S,13S,15aS,20R,20aS)-20-(tert-butylcarbamoyl)-1-(((tert butyldimethylsilyl)oxy)methyl)-4-methyl-3,6,9,12,15-pentaoxo-13-(3-(3-(((2,2,4,6,7-pentamethyl-2,3-dihydrobenzofuran-5-yl)sulfonyl)guanidino)propyl)icosahydroazirino[1,2-a]pyrrolo[1,2-d][1,4,7,10,13,16]hexaazacyclooctadecin-7-yl)acetate (18)

$^1$H NMR (400 MHz, CDCl$_3$) δ: 7.84 (d, J=9.7 Hz, 2H), 7.58 (dd, J=18.1, 9.1 Hz, 2H), 7.07 (s, 1H), 6.41 (s, 2H), 5.68 (s, 1H), 4.85 (dq, J=13.7, 6.8 Hz, 1H), 4.70-4.58 (m, 1H), 4.35 (q, J=8.1 Hz, 1H), 4.17-4.07 (m, 1H), 3.97 (dd, J=14.2, 7.5 Hz, 2H), 3.74 (s, 1H), 3.69-3.57 (m, 1H), 3.56-3.42 (m, 2H), 3.42-3.13 (m, 4H), 2.96 (s, 2H), 2.93 (d, J=2.3 Hz, 1H), 2.89-2.76 (m, 4H), 2.66-2.53 (m, 7H), 2.42-2.15 (m, 2H), 2.10 (s, 3H), 2.07-1.98 (m, 1H), 1.87-1.55 (m, 8H), 1.46 (s, 6H), 1.44 (s, 9H), 1.34 (s, 9H), 0.87 (s, 9H), 0.09 (s, 3H), 0.05 (s, 3H). $^{13}$C NMR (101 MHz, CDCl$_3$) δ: 187.07, 176.14, 174.46, 171.46, 171.04, 169.11, 166.93, 158.77, 156.39, 138.63, 133.66, 132.55, 124.65, 117.55, 105.24, 86.49, 82.64, 63.92, 63.84, 60.81, 57.07, 51.69, 51.31, 50.37, 49.56, 45.47, 43.51, 40.43, 37.55, 35.99, 30.28, 29.17, 28.83, 28.22, 26.11, 24.61, 19.49, 18.71, 18.19, 17.31, 12.69, –5.11, –5.44. MS (ESI) [MH]$^+$ calcd. 1104.6. found 1104.6 tert-butyl (4-((1S,4S,7S,10S,13S,15aS,20R,20aS)-13-((R)-1-(tert-butoxy)ethyl)-20-(tert-butylcarbamoyl)-1-(((tert-butyldimethylsilypoxy)methyl)-4-methyl-10-(2-(methylthio)ethyl)-3,6,9,12,15-pentaoxoicosahydroazirino[1,2-a]pyrrolo[1,2d][1,4,7,10,13,16]hexaazacyclooctadecin-7-yl)butyl)carbamate (19)

$^1$H NMR (400 MHz, CDCl$_3$) δ: 7.83 (d, J=8.1 Hz, 1H), 7.77 (s, 1H), 7.50 (d, J=21.3 Hz, 1H), 7.35 (m, 2H), 7.08 (dd, J=15.7, 7.5 Hz, 1H), 6.90 (s, 1H), 6.82 (s, 1H), 4.98 (d, J=27.6 Hz, 1H), 4.84-4.67 (m, 1H), 4.60 (s, 1H), 4.40-4.30 (m, 1H), 4.16-3.93 (m, 4H), 3.82 (s, 2H), 3.77-3.69 (m, 3H), 3.67 (d, J=6.3 Hz, 1H), 3.45-3.28 (m, 2H), 3.27-2.99 (m, 6H), 3.00-2.86 (m, 2H), 2.84 (s, 1H), 2.78-2.55 (m, 3H), 2.45-2.19 (m, 5H), 2.12 (s, 4H), 2.06-1.97 (m, 3H), 1.89 (d, J=4.7 Hz, 7H), 1.71-1.55 (m, 3H), 1.54-1.39 (m, 21H), 1.36 (s, 13H), 1.31-1.26 (m, 12H), 1.06 (t, J=10.5 Hz, 4H), 0.93-0.82 (m, 14H), 0.06 (s, 3H), 0.05 (s, 3H). $^{13}$C NMR (101 MHz, CDCl$_3$) δ: 182.99, 175.20, 171.94, 170.75, 170.37, 168.93, 156.44, 77.43, 75.69, 66.32, 64.35, 63.93, 61.77, 57.52, 56.58, 54.28, 42.68, 40.37, 31.21, 30.95, 30.08, 29.88, 29.36, 28.85, 28.66, 26.01, 24.92, 24.16, 18.91, 18.48, 17.89, 15.48, –5.25, –5.29. MS (ESI) [MH]$^+$ calcd. 983.6, found 983.6

(1S,7S,10S,15aS,20R,20aS)-10-((1H-imidazol-5-yl)methyl)-7-(4-(tert-butoxy)benzyl)-N-(tert-butyl)-1-(((tert-butyldimethylsilyl)oxy)methyl)-3,6,9,12,15-pentaoxoicosahydroazirino[1,2-a]pyrrolo[1,2-d][1,4,7,10,13,16]hexaazacyclooctadecine-20-carboxamide (20)

$^1$H NMR (400 MHz, CDCl$_3$) δ: 9.92 (s, 1H), 7.49 (d, J=4.8 Hz, 2H), 7.39-7.27 (m, 11H), 7.17-7.02 (m, 11H), 6.78 (d, J=8.4 Hz, 2H), 6.69 (s, 1H), 4.48 (p, J=6.9 Hz, 1H), 4.42-4.18 (m, 2H), 4.06-3.99 (m, 1H), 3.91 (dd, J=11.4, 3.8 Hz, 1H), 3.78 (dd, J=11.3, 4.4 Hz, 1H), 3.61 (dd, J=9.8, 4.8 Hz, 1H), 3.48-3.37 (m, 1H), 3.32-2.99 (m, 8H), 2.83 (dd, J=6.8, 3.4 Hz, 1H), 2.41-1.95 (m, 2H), 1.91-1.72 (m, 2H), 1.61 (s, 12H), 1.41 (s, 10H), 1.35-1.24 (m, 20H), 0.72 (s, 1H), 0.07 (s, 3H), 0.05 (s, 3H). $^{13}$C NMR (101 MHz, CDCl$_3$) δ: 184.31, 175.20, 172.61, 170.67, 169.47, 168.12, 154.53, 142.31, 138.19, 136.81, 131.91, 129.97, 129.85, 128.43, 128.37, 120.09, 77.43, 63.49, 62.17, 61.55, 57.84, 54.97, 52.19, 51.15, 48.67, 43.36, 42.53, 41.75, 36.36, 31.84, 30.99, 29.92, 29.88, 29.44, 29.05, 28.67, 26.07, 24.49, 19.80, 18.56, –5.19. MS (ESI) [MH]$^+$ calcd. 866.5. found 866.5

(1S,4S,7S,13S,15aS,20R,20aS)-13-benzyl-N-(tert-butyl)-1-(((tert-butyldimethylsilyl)oxy)methyl)-4-methyl-3,6,9,12,15-pentaoxo-7-(2-oxo-2-(tritylamino)ethyl)icosahydroazirino[1,2-a]pyrrolo[1,2-d][1,4,7,10,13,16]hexaazacyclooctadecine-20-carboxamide (21)

$^1$H NMR (400 MHz, CDCl$_3$) δ: 7.94 (t, J=9.8 Hz, 2H), 7.73 (d, J=8.7 Hz, 1H), 7.51 (t, J=6.7 Hz, 1H), 7.34-7.11 (m, 23H), 6.79 (s, 1H), 4.92-4.72 (m, 2H), 4.59 (dd, J=16.3, 8.6 Hz, 1H), 4.25 (d, J=11.5 Hz, 1H), 4.01 (d, J=10.7 Hz, 1H), 3.82 (dd, J=14.2, 7.6 Hz, 1H), 3.73 (s, 1H), 3.59-3.51 (m, 2H), 3.48-3.24 (m, 3H), 3.09 (dd, J=13.8, 8.9 Hz, 1H), 2.96-2.68 (m, 6H), 2.59 (dd, J=15.8, 3.6 Hz, 1H), 2.45-2.08 (m, 2H), 2.07-1.96 (m, 1H), 1.62 (s, 5H), 1.52-1.17 (m, 18H), 0.94 (s, 9H), 0.15 (s, 3H), 0.13 (s, 3H). $^{13}$C NMR (101 MHz, CDCl$_3$) δ: 184.06, 175.64, 173.93, 171.01, 170.49, 169.15, 167.20, 144.28, 136.98, 129.61, 128.81, 128.49, 128.30, 127.48, 126.75, 77.55, 77.23, 76.91, 71.17, 63.63, 60.72, 57.12, 52.96, 51.54, 50.58, 49.71, 49.27, 45.35, 44.53, 37.27, 36.80, 33.93, 30.22, 29.24, 26.24, 24.32, 18.78, 17.89, 0.22, −5.11, −5.34. MS (ESI) [MH]$^+$ calcd. 1027.5. found 1027.6

(4S,10S,15aS,20R,20aS)-4-benzyl-N-(tert-butyl)-10-isobutyl-3,6,9,12,15-pentaoxoicosahydroazirino[1,2-a]pyrrolo[1,2-d][1,4,7,10,13,16]hexaazacyclooctadecine-20-carboxamide (22)

$^1$H NMR (CDCl$_3$, 400 MHz) δ: 8.33 (bs, 1H), 8.17 (d, J=9.1 Hz, 1H), 8.03 (d,J=7.4 Hz, 1H), 7.54 (s, 1H), 7.21 (m, 5H), 6.04 (bs, 1H), 5.08 (bs, 1H), 4.58 (m, 1H), 3.87 (dd, J=8.1 Hz, 5.0 Hz, 1H), 3.80 (bs, 1H), 2.48 (dd, J=3.6 Hz, 1.8 Hz, 2H), 2.16 (m, 2H), 1.62-1.57 (m, 7H), 1.48 (m, 2H), 1.42 (m, 2H), 1.35 (m, 2H), 1.20 (m, 9H), 1.07 (m, 2H), 0.81 (m, 6H) ppm. MS (ESI) [MH]$^+$ calcd. 626.8. found 626.3 and 313.7 for [M+2H]$^{2+}$/2

7-mmc conjugated 22 (23)

Cyclic peptide 22 was reacted as a crude material to yield conjugated peptide 23. (see page 39) $^1$H NMR (300 MHz, DMSO) δ 8.95 (s, 1H), 8.68 (d, J=8.2 Hz, 1H), 8.32 (t, J=6.3 Hz, 1H), 7.68 (d, J=8.4 Hz, 1H), 7.51 (d, J=9.4 Hz, 1H), 7.42-7.08 (m, 5H), 6.46 (s, 1H), 6.31 (s, 1H), 4.47-4.15 (m, 3H), 3.73 (dd, J=20.5, 14.1 Hz, 3H), 3.45-3.33 (m, 2H), 3.17 (dd, J=20.9, 13.0 Hz, 2H), 2.98-2.64 (m, 4H), 2.40 (s, 2H), 2.22-2.10 (m, 1H), 1.91 (ddd, J=22.9, 13.4, 6.6 Hz, 2H), 1.79-1.40 (m, 5H), 1.30-1.15 (m, 9H), 0.93-0.74 (m, 6H). MS (ESI) [MH]$^+$ calcd. 818.4. found 818.3

HATU-mediated Cyclization

Advantageously, the cyclization reaction can be run at least at 0.002M concentration of the starting amino acid/peptide. Preferably the concentration is run between 0.002M to 0.2M.

In another embodiment the process is run at a concentration of at least 0.1M of the starting amino acid/peptide. In another embodiment the process is run at a concentration of around 0.2M of the starting amino acid/peptide.

Traditionally, prior macrocyclizations cannot be performed at such high concentrations. This was demonstrated using a direct comparison with HATU process which fails in that the major products observed are derived from oligomerization and polymerization.

O-(7-Azabenzotriazol-1-yl)-N,N,N',N'-tetramethyluronium hexafluorophosphate ("HATU")-mediated cyclization of Pro-Gly-Gly-Gly was compared with the amino aldehyde/isocyanide cyclization method at 0.2 M. Upon completion, crude reaction mixtures were analyzed using liquid chromatography electrospray ionization mass spectrometry ("LC-MS(ESI)") to assess the level of selectivity for the desired cyclic peptide.

Mass spectrometry ("MS")-analysis of the HATU reaction revealed that cyclodimerization predominated at 0.2M (FIG. 28). The major peaks at m/z=537.2 and 559.2 correspond to the cyclodimer product, and its sodium chelate, respectively, while only trace amounts of the desired cyclic peptide was detected at m/z=269. The cyclotrimer (m/z=805) was also detected. The crude reaction mixture also contained several other unidentified byproducts.

Results from the MS peak analysis found 6 components.

Component 1: Peak at Scan 27.4. Top ions are 655 566 923

Component 2: Peak at Scan 28.4. Top ions are 982 744 714

Component 3: Peak at Scan 29.9. Top ions are 235 848 538

Component 4: Peak at Scan 30.9. Top ions are 559 827 560

Component 5: Peak at Scan 31.9. Top ions are 752 931

Component 6: Peak at Scan 32.7. Top ions are 537 295 446

The crude LC-MS(ESI) analysis for the isocyanide/amino aldehyde mediated cyclization revealed a high level of selectivity for the desired cyclic peptide (m/z=479) at 0.2M (FIG. 29). No trace peaks were detected for either dimer or trimer byproduct. Only characteristic fragmentation peaks and residual Pro-Gly-Gly-Gly remained in the reaction mixture.

Results from the MS peak analysis found 2 components.

Component 1: Peak at Scan 29.7. Top ions are 287 212 383 (Pro-Gly-Gly-Gly)

Component 2: Peak at Scan 30.9. Top ions are 479 396 240 (cyclic peptide)

Example 2

Methods and Materials

Method A: ring-opening of aziridine-containing cyclic peptide is conducted using an aromatic thiol as the nucleophile (Method A). In a screw-cap vial equipped with a magnetic stirring bar was added aziridine-containing cyclic peptide (0.06 mmol) and aromatic thiol (0.066 mmol) were added to 0.2 ml of degassed CHCl$_3$. NEt$_3$ (0.06 mmol) was then added to the solution and the reaction was stirred at room temperature for 3-4 hours. The reaction was then diluted with CH$_2$Cl$_2$, and washed twice with saturated aqueous NH$_4$Cl (3 ml) followed by one wash with brine (3 ml). The organic layer was subsequently dried over Na$_2$SO$_4$, filtered, and concentrated under reduced pressure. The crude ring-opened products were of high purity, but analytically pure samples were obtained following purification by flash column chromatography (5% MeOH in EtOAc).

Method B: ring-opening of aziridine-containing cyclic peptide is carried out using an aliphatic thiol or imide as the nucleophile (Method B). In a screw-cap vial equipped with a magnetic stirring bar was added aziridine-containing cyclic peptide (0.06 mmol) and aliphatic thiol or imide (0.066 mmol) to 0.2 ml of degassed CHCl$_3$. DBU (0.06 mmol) was then added to the solution and the reaction was stirred at room temperature for 3-4 hours. The reaction was then diluted with CH$_2$Cl$_2$, and washed twice with saturated aqueous NH$_4$Cl (3 ml) followed by one wash with brine (3 ml). The organic layer was subsequently dried over Na$_2$SO$_4$, filtered, and concentrated under reduced pressure. The crude ring-opened products were of high purity, but analytically pure samples were obtained following purification by flash column chromatography (5% MeOH in EtOAc).

Results

Side chains including, but not limited to, fluorescent substituents have been appended to the products of macrocyclization (Scheme 3).

Scheme 3. Late-stage, site-specific attachment of fluorescent tags to a cyclic peptide.

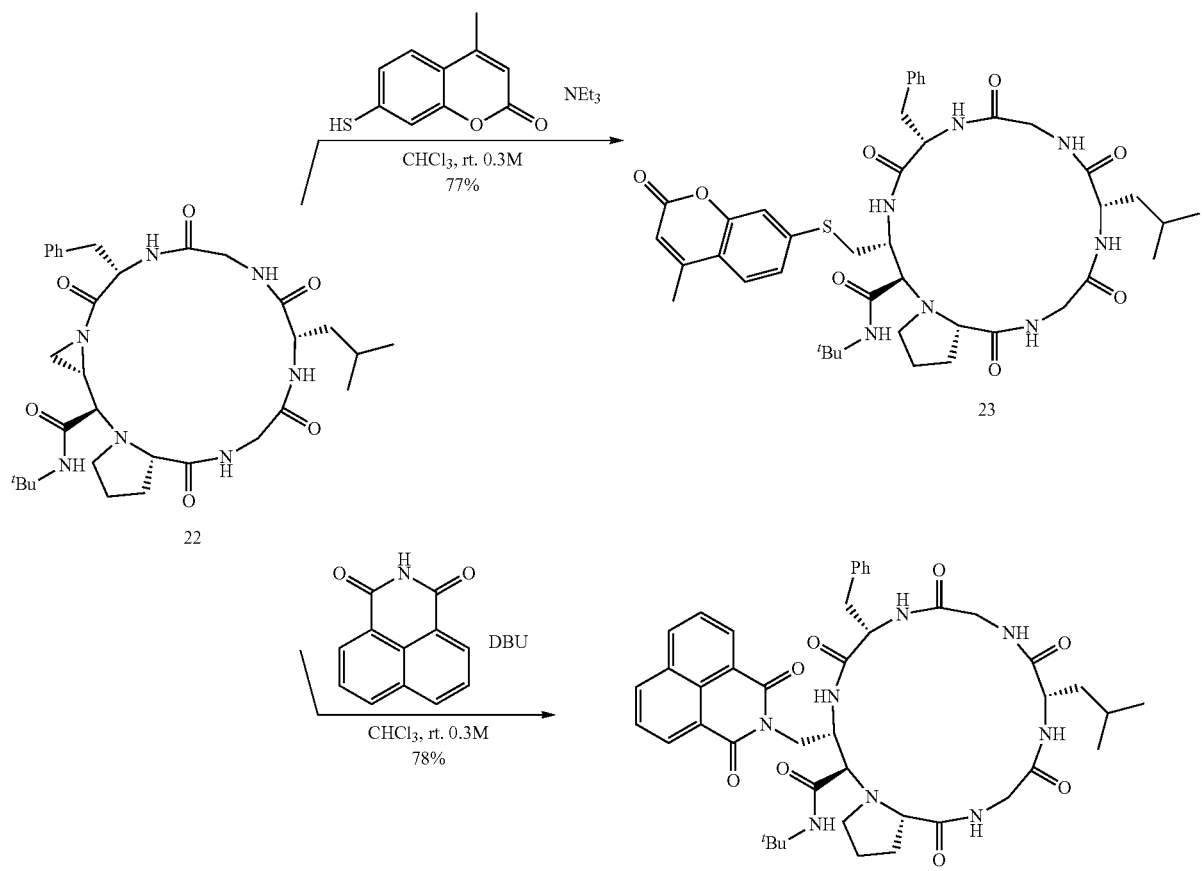

The incorporation of an activated aziridine ring into the framework of a cyclic peptide provides a useful point for conjugation to various side-chains via nucleophilic ring-opening, a well developed methodology that has been demonstrated using nucleophilic biomolecules ranging from carbohydrates to biotin and farnesyl derivatives.[14] As an example, cyclic peptide conjugation strategy can be demonstrated through the nucleophilic ring-opening of an aziridine moiety with the widely used fluorescent tag 7-mercapto-4-methyl-coumarin (7-mmc) (Scheme 3). In another aspect, a late-stage synthesis of a thioester residue by ring-opening of the cyclic peptide with commercially available thiobenzoic acid can also be used. The reaction proceeded smoothly, delivering the ring opened product in 98% yield. The late-stage incorporation of the thioester functionality avoids steps typically required for its protection from both oxidation and electrophilic reagents. Many other amino acid side chains, both natural and unnatural, can be installed by similar ring-opening protocols, opening doors for conformational optimization of cyclic peptides at a late stage of synthesis. Other nucleophiles such as aliphatic thiols, acids, secondary amines such as morpholine, and imides worked equally well during ring-opening.

In another aspect, cyclic peptides equipped with aziridine rings are subjected to ring-opening (FIG. 30). In the course of this process, a side-chain of interest can be appended to the cyclic peptide scaffold at a late stage of synthesis. The ring-opening reactions were carried out using an appropriate base/nucleophile system that was selected on the basis of $pK_a$. The preferred reactions involved the employment of a base/nucleophile pair satisfying $\Delta pK_a = pK_a[NR3H+] - pK_a[Nucleophile] \approx -1$ (FIG. 31).

These data suggest that strong ion pairing ($\Delta pK_a > 1$) between the base and nucleophile may result in decreased reactivity. The optimized conditions for ring-opening were found to proceed cleanly to afford the modified cyclic peptides in high purity following extractive work-up (FIG. 32).

Example 3

X-ray analysis of cyclic product 1 was conducted.
Results

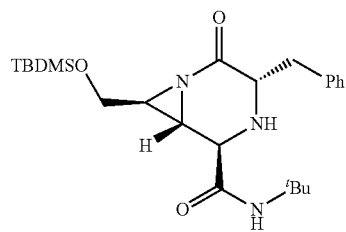 [SMILES: CC(C)(C)NC(=O)[C@@H]1N[C@@H](Cc2ccccc2)C(=O)N2[C@H]1[C@H]2CO[Si](C)(C)C(C)(C)C]

TABLE 4

Crystal data and structure refinement for k07227.

| | |
|---|---|
| Identification code | k07227 |
| Empirical formula | C24H38N3O3Si |
| Formula weight | 445.67 |
| Temperature | 150(2) K |
| Wavelength | 0.71073 Å |
| Crystal system | Monoclinic |
| Space group | P 21 |
| Unit cell dimensions | a = 14.590(2) Å  α = 90°. |
| | b = 12.326(2) Å  β = 94.718(7)°. |
| | c = 15.088(2) Å  γ = 90°. |
| Volume | 2704.2(7) Å$^3$ |
| Z | 4 |
| Density (calculated) | 1.097 Mg/m$^3$ |
| Absorption coefficient | 0.115 mm$^{-1}$ |
| F(000) | 968 |
| Crystal size | 0.32 × 0.10 × 0.08 mm$^3$ |
| Theta range for data collection | 2.62 to 23.05°. |
| Index ranges | −15 <= h <= 15, −13 <= k <= 12, |
| | −15 <= l <= 16 |
| Reflections collected | 10115 |
| Independent reflections | 3828 [R(int) = 0.1359] |
| Completeness to theta = 23.05° | 95.9% |
| Absorption correction | Semi-empirical from equivalents |
| Max. and min. transmission | 1.000 and 0.770 |
| Refinement method | Full-matrix least-squares on F$^2$ |
| Data/restraints/parameters | 3828/1/559 |
| Goodness-of-fit on F$^2$ | 1.044 |
| Final R indices [I > 2sigma(I)] | R1 = 0.0982, wR2 = 0.2560 |
| R indices (all data) | R1 = 0.1715, wR2 = 0.3055 |
| Largest diff. peak and hole | 0.492 and −0.316 e · Å$^{-3}$ |

TABLE 5

Atomic coordinates (× 10$^4$) and equivalent isotropic displacement parameters (Å$^2$ × 10$^3$) for k07227. U(eq) is defined as one third of the trace of the orthogonalized U$^{ij}$ tensor.

| | x | y | z | U(eq) |
|---|---|---|---|---|
| Si(1A) | 7245(3) | 4768(4) | 8396(3) | 68(1) |
| O(1A) | 3310(7) | 4696(12) | 6317(8) | 94(4) |
| O(2A) | 4778(6) | 4429(8) | 4729(7) | 62(3) |
| O(3A) | 4070(7) | 3807(11) | 8551(7) | 82(3) |
| O(4A) | 6881(6) | 4731(9) | 7332(6) | 64(3) |
| N(1A) | 5222(7) | 4298(9) | 6198(7) | 53(3) |
| N(2A) | 2735(8) | 3545(13) | 7673(8) | 74(4) |
| C(1A) | 4577(10) | 4187(12) | 5473(9) | 56(4) |
| C(2A) | 3624(9) | 3854(14) | 5700(9) | 61(4) |
| C(3A) | 3884(8) | 4758(14) | 7161(9) | 61(4) |
| C(4A) | 4916(9) | 4610(11) | 7073(9) | 57(4) |
| C(5A) | 5474(9) | 5392(12) | 6570(9) | 55(4) |
| C(6A) | 6464(10) | 5591(15) | 6823(10) | 72(5) |
| C(7A) | 7044(16) | 3423(18) | 8820(12) | 118(8) |
| C(8A) | 6568(12) | 5820(20) | 9009(13) | 105(6) |
| C(9A) | 8501(12) | 5097(14) | 8489(14) | 86(6) |
| C(10A) | 8607(13) | 6160(30) | 8022(19) | 150(11) |
| C(11A) | 9045(13) | 4350(30) | 8043(17) | 169(14) |
| C(12A) | 8846(14) | 5210(20) | 9454(15) | 133(9) |
| C(13A) | 3590(10) | 3973(17) | 7871(11) | 76(5) |
| C(14A) | 2268(10) | 2780(16) | 8263(10) | 74(5) |
| C(15A) | 2819(13) | 1767(18) | 8419(13) | 103(6) |
| C(16A) | 2093(11) | 3415(16) | 9107(10) | 86(6) |
| C(17A) | 1325(12) | 2540(20) | 7748(12) | 110(7) |
| C(18A) | 2957(9) | 3707(15) | 4897(9) | 66(4) |
| C(19A) | 2151(10) | 3006(18) | 5091(10) | 77(5) |
| C(20A) | 2294(13) | 1877(19) | 5232(12) | 90(5) |
| C(21A) | 1548(17) | 1230(20) | 5361(14) | 112(7) |
| C(22A) | 725(19) | 1640(30) | 5502(16) | 128(9) |
| C(23A) | 525(13) | 2770(30) | 5385(13) | 116(9) |
| C(24A) | 1270(12) | 3480(20) | 5217(11) | 101(7) |
| Si(1B) | 8204(3) | 2344(4) | 2871(3) | 68(1) |
| O(1B) | 6478(7) | 2195(11) | 6755(7) | 86(3) |
| O(2B) | 4724(6) | 1912(7) | 5174(6) | 53(2) |
| O(3B) | 8659(6) | 1106(10) | 6205(7) | 75(3) |
| O(4B) | 7241(6) | 2259(8) | 3360(6) | 66(3) |

TABLE 5-continued

Atomic coordinates (× 10$^4$) and equivalent isotropic displacement parameters (Å$^2$ × 10$^3$) for k07227. U(eq) is defined as one third of the trace of the orthogonalized U$^{ij}$ tensor.

| | x | y | z | U(eq) |
|---|---|---|---|---|
| N(1B) | 6249(7) | 1815(8) | 4890(7) | 48(3) |
| N(2B) | 7884(8) | 963(11) | 7449(9) | 69(3) |
| C(1B) | 5494(10) | 1740(12) | 5431(9) | 55(4) |
| C(2B) | 5816(9) | 1389(12) | 6398(9) | 53(4) |
| C(3B) | 7344(9) | 2232(14) | 6288(8) | 59(4) |
| C(4B) | 7165(9) | 2098(12) | 5256(9) | 60(4) |
| C(5B) | 6589(10) | 2897(14) | 4693(11) | 70(4) |
| C(6B) | 6790(11) | 3147(14) | 3790(11) | 74(5) |
| C(7B) | 8766(12) | 968(16) | 3042(13) | 97(6) |
| C(8B) | 8926(11) | 3466(19) | 3390(11) | 98(6) |
| C(9B) | 7893(10) | 2620(14) | 1666(10) | 71(5) |
| C(10B) | 7510(13) | 3777(14) | 1548(11) | 85(5) |
| C(11B) | 7165(14) | 1807(19) | 1279(12) | 103(6) |
| C(12B) | 8748(12) | 2536(19) | 1143(11) | 100(6) |
| C(13B) | 8015(10) | 1332(15) | 6630(12) | 69(4) |
| C(14B) | 8453(10) | 163(13) | 7952(11) | 66(4) |
| C(15B) | 8439(13) | −842(17) | 7445(15) | 111(7) |
| C(16B) | 9438(11) | 564(17) | 8135(13) | 97(6) |
| C(17B) | 8040(11) | 0(20) | 8825(11) | 103(7) |
| C(18B) | 5021(9) | 1225(13) | 6976(9) | 61(4) |
| C(19B) | 5242(8) | 526(15) | 7787(10) | 65(5) |
| C(20B) | 5337(10) | −610(14) | 7633(11) | 65(4) |
| C(21B) | 5477(11) | −1260(20) | 8343(13) | 101(7) |
| C(22B) | 5524(12) | −940(20) | 9202(18) | 105(7) |
| C(23B) | 5439(11) | 130(30) | 9374(13) | 100(7) |
| C(24B) | 5292(10) | 878(19) | 8643(11) | 86(6) |

TABLE 6

Bond lengths [Å] and angles [°] for k07227.

| | |
|---|---|
| Si(1A)—O(4A) | 1.649(10) |
| Si(1A)—C(7A) | 1.81(2) |
| Si(1A)—C(9A) | 1.871(18) |
| Si(1A)—C(8A) | 1.91(2) |
| O(1A)—C(3A) | 1.468(17) |
| O(1A)—C(2A) | 1.491(18) |
| O(2A)—C(1A) | 1.221(15) |
| O(3A)—C(13A) | 1.211(17) |
| O(4A)—C(6A) | 1.418(18) |
| N(1A)—C(1A) | 1.390(17) |
| N(1A)—C(4A) | 1.479(16) |
| N(1A)—C(5A) | 1.494(18) |
| N(2A)—C(13A) | 1.36(2) |
| N(2A)—C(14A) | 1.50(2) |
| C(1A)—C(2A) | 1.52(2) |
| C(2A)—C(18A) | 1.502(19) |
| C(3A)—C(13A) | 1.53(2) |
| C(3A)—C(4A) | 1.533(18) |
| C(4A)—C(5A) | 1.507(19) |
| C(5A)—C(6A) | 1.48(2) |
| C(9A)—C(11A) | 1.42(3) |
| C(9A)—C(10A) | 1.50(3) |
| C(9A)—C(12A) | 1.51(3) |
| C(14A)—C(15A) | 1.49(3) |
| C(14A)—C(16A) | 1.53(2) |
| C(14A)—C(17A) | 1.55(2) |
| C(18A)—C(19A) | 1.51(2) |
| C(19A)—C(20A) | 1.42(3) |
| C(19A)—C(24A) | 1.44(2) |
| C(20A)—C(21A) | 1.38(3) |
| C(21A)—C(22A) | 1.34(3) |
| C(22A)—C(23A) | 1.44(4) |
| C(23A)—C(24A) | 1.44(3) |
| Si(1B)—O(4B) | 1.643(9) |
| Si(1B)—C(9B) | 1.868(16) |
| Si(1B)—C(8B) | 1.871(19) |
| Si(1B)—C(7B) | 1.893(18) |
| O(1B)—C(2B) | 1.457(18) |
| O(1B)—C(3B) | 1.496(16) |
| O(2B)—C(1B) | 1.177(15) |

TABLE 6-continued

Bond lengths [Å] and angles [°] for k07227.

| Bond | Value |
|---|---|
| O(3B)—C(13B) | 1.214(16) |
| O(4B)—C(6B) | 1.457(18) |
| N(1B)—C(1B) | 1.428(17) |
| N(1B)—C(4B) | 1.446(17) |
| N(1B)—C(5B) | 1.461(19) |
| N(2B)—C(13B) | 1.344(19) |
| N(2B)—C(14B) | 1.461(19) |
| C(1B)—C(2B) | 1.56(2) |
| C(2B)—C(18B) | 1.522(18) |
| C(3B)—C(13B) | 1.54(2) |
| C(3B)—C(4B) | 1.567(18) |
| C(4B)—C(5B) | 1.51(2) |
| C(5B)—C(6B) | 1.45(2) |
| C(9B)—C(12B) | 1.53(2) |
| C(9B)—C(10B) | 1.54(2) |
| C(9B)—C(11B) | 1.54(2) |
| C(14B)—C(15B) | 1.45(3) |
| C(14B)—C(17B) | 1.51(2) |
| C(14B)—C(16B) | 1.52(2) |
| C(18B)—C(19B) | 1.51(2) |
| C(19B)—C(24B) | 1.36(2) |
| C(19B)—C(20B) | 1.43(2) |
| C(20B)—C(21B) | 1.34(2) |
| C(21B)—C(22B) | 1.35(3) |
| C(22B)—C(23B) | 1.35(3) |
| C(23B)—C(24B) | 1.44(3) |
| O(4A)—Si(1A)—C(7A) | 105.7(8) |
| O(4A)—Si(1A)—C(9A) | 108.3(7) |
| C(7A)—Si(1A)—C(9A) | 111.0(9) |
| O(4A)—Si(1A)—C(8A) | 110.6(8) |
| C(7A)—Si(1A)—C(8A) | 110.1(10) |
| C(9A)—Si(1A)—C(8A) | 111.0(9) |
| C(3A)—O(1A)—C(2A) | 113.3(11) |
| C(6A)—O(4A)—Si(1A) | 126.6(10) |
| C(1A)—N(1A)—C(4A) | 119.6(10) |
| C(1A)—N(1A)—C(5A) | 121.0(11) |
| C(4A)—N(1A)—C(5A) | 60.9(8) |
| C(13A)—N(2A)—C(14A) | 124.4(13) |
| O(2A)—C(1A)—N(1A) | 120.1(13) |
| O(2A)—C(1A)—C(2A) | 124.6(12) |
| N(1A)—C(1A)—C(2A) | 115.0(11) |
| O(1A)—C(2A)—C(18A) | 112.0(12) |
| O(1A)—C(2A)—C(1A) | 106.7(12) |
| C(18A)—C(2A)—C(1A) | 113.3(11) |
| O(1A)—C(3A)—C(13A) | 113.7(13) |
| O(1A)—C(3A)—C(4A) | 114.4(11) |
| C(13A)—C(3A)—C(4A) | 108.6(12) |
| N(1A)—C(4A)—C(5A) | 60.0(8) |
| N(1A)—C(4A)—C(3A) | 118.7(11) |
| C(5A)—C(4A)—C(3A) | 122.9(12) |
| C(6A)—C(5A)—N(1A) | 116.8(12) |
| C(6A)—C(5A)—C(4A) | 122.1(12) |
| N(1A)—C(5A)—C(4A) | 59.1(8) |
| O(4A)—C(6A)—C(5A) | 112.4(12) |
| C(11A)—C(9A)—C(10A) | 105(2) |
| C(11A)—C(9A)—C(12A) | 111.3(18) |
| C(10A)—C(9A)—C(12A) | 109(2) |
| C(11A)—C(9A)—Si(1A) | 113.9(16) |
| C(10A)—C(9A)—Si(1A) | 107.0(12) |
| C(12A)—C(9A)—Si(1A) | 109.9(13) |
| O(3A)—C(13A)—N(2A) | 125.1(16) |
| O(3A)—C(13A)—C(3A) | 121.6(14) |
| N(2A)—C(13A)—C(3A) | 113.2(14) |
| C(15A)—C(14A)—N(2A) | 110.8(13) |
| C(15A)—C(14A)—C(16A) | 114.8(16) |
| N(2A)—C(14A)—C(16A) | 106.7(15) |
| C(15A)—C(14A)—C(17A) | 111.4(17) |
| N(2A)—C(14A)—C(17A) | 104.4(13) |
| C(16A)—C(14A)—C(17A) | 108.1(14) |
| C(2A)—C(18A)—C(19A) | 112.2(12) |
| C(20A)—C(19A)—C(24A) | 120.2(19) |
| C(20A)—C(19A)—C(18A) | 118.9(16) |
| C(24A)—C(19A)—C(18A) | 121(2) |
| C(21A)—C(20A)—C(19A) | 119(2) |
| C(22A)—C(21A)—C(20A) | 122(3) |
| C(21A)—C(22A)—C(23A) | 122(3) |
| C(22A)—C(23A)—C(24A) | 118(2) |
| C(23A)—C(24A)—C(19A) | 118(2) |
| O(4B)—Si(1B)—C(9B) | 107.5(6) |
| O(4B)—Si(1B)—C(8B) | 109.4(7) |
| C(9B)—Si(1B)—C(8B) | 110.9(8) |
| O(4B)—Si(1B)—C(7B) | 105.0(7) |
| C(9B)—Si(1B)—C(7B) | 111.3(9) |
| C(8B)—Si(1B)—C(7B) | 112.5(9) |
| C(2B)—O(1B)—C(3B) | 114.0(11) |
| C(6B)—O(4B)—Si(1B) | 125.9(10) |
| C(1B)—N(1B)—C(4B) | 122.0(11) |
| C(1B)—N(1B)—C(5B) | 117.7(11) |
| C(4B)—N(1B)—C(5B) | 62.6(9) |
| C(13B)—N(2B)—C(14B) | 126.0(13) |
| O(2B)—C(1B)—N(1B) | 124.1(13) |
| O(2B)—C(1B)—C(2B) | 124.4(12) |
| N(1B)—C(1B)—C(2B) | 111.4(11) |
| O(1B)—C(2B)—C(18B) | 113.1(11) |
| O(1B)—C(2B)—C(1B) | 107.3(11) |
| C(18B)—C(2B)—C(1B) | 112.9(11) |
| O(1B)—C(3B)—C(13B) | 111.0(12) |
| O(1B)—C(3B)—C(4B) | 112.7(10) |
| C(13B)—C(3B)—C(4B) | 107.8(12) |
| N(1B)—C(4B)—C(5B) | 59.2(8) |
| N(1B)—C(4B)—C(3B) | 118.6(10) |
| C(5B)—C(4B)—C(3B) | 122.0(13) |
| C(6B)—C(5B)—N(1B) | 118.9(14) |
| C(6B)—C(5B)—C(4B) | 121.4(13) |
| N(1B)—C(5B)—C(4B) | 58.2(9) |
| C(5B)—C(6B)—O(4B) | 113.1(13) |
| C(12B)—C(9B)—C(10B) | 107.8(14) |
| C(12B)—C(9B)—C(11B) | 109.0(15) |
| C(10B)—C(9B)—C(11B) | 109.1(14) |
| C(12B)—C(9B)—Si(1B) | 110.2(11) |
| C(10B)—C(9B)—Si(1B) | 109.8(12) |
| C(11B)—C(9B)—Si(1B) | 110.8(12) |
| O(3B)—C(13B)—N(2B) | 125.6(15) |
| O(3B)—C(13B)—C(3B) | 119.1(14) |
| N(2B)—C(13B)—C(3B) | 114.7(13) |
| C(15B)—C(14B)—N(2B) | 108.6(13) |
| C(15B)—C(14B)—C(17B) | 110.9(16) |
| N(2B)—C(14B)—C(17B) | 107.0(13) |
| C(15B)—C(14B)—C(16B) | 110.2(15) |
| N(2B)—C(14B)—C(16B) | 111.3(13) |
| C(17B)—C(14B)—C(16B) | 108.9(15) |
| C(19B)—C(18B)—C(2B) | 114.7(11) |
| C(24B)—C(19B)—C(20B) | 118.0(16) |
| C(24B)—C(19B)—C(18B) | 125.4(18) |
| C(20B)—C(19B)—C(18B) | 116.5(14) |
| C(21B)—C(20B)—C(19B) | 117.9(18) |
| C(20B)—C(21B)—C(22B) | 125(3) |
| C(23B)—C(22B)—C(21B) | 119(2) |
| C(22B)—C(23B)—C(24B) | 119(2) |
| C(19B)—C(24B)—C(23B) | 121(2) |

TABLE 7

Anisotropic displacement parameters (Å² × 10³) for k07227.
The anisotropic displacement factor exponent takes the form:
$-2\pi^2[h^2 a^{*2}U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| Si(1A) | 59(2) | 75(3) | 67(3) | −5(2) | −2(2) | −7(2) |
| O(1A) | 67(6) | 116(10) | 101(8) | −29(8) | 23(6) | −1(7) |
| O(2A) | 66(6) | 55(6) | 64(7) | −6(5) | 11(5) | 0(5) |
| O(3A) | 61(6) | 118(10) | 66(7) | 14(7) | 8(5) | −7(6) |
| O(4A) | 55(5) | 64(6) | 76(6) | 5(6) | 11(4) | −3(5) |
| N(1A) | 54(7) | 54(7) | 54(7) | −6(6) | 19(6) | 1(6) |
| N(2A) | 51(7) | 99(11) | 74(8) | 17(8) | 12(6) | 6(7) |
| C(1A) | 77(10) | 49(9) | 40(8) | 1(7) | −2(7) | 3(7) |
| C(2A) | 60(9) | 70(10) | 52(8) | −9(8) | 3(7) | 6(8) |
| C(3A) | 44(7) | 70(10) | 70(9) | −7(9) | 5(6) | 7(7) |
| C(4A) | 61(8) | 46(9) | 65(9) | 9(7) | 7(7) | 0(7) |
| C(5A) | 51(8) | 48(9) | 64(9) | 4(7) | 4(7) | 4(7) |
| C(6A) | 62(10) | 86(13) | 69(10) | 20(10) | 18(8) | −7(9) |
| C(7A) | 170(20) | 110(17) | 71(12) | 20(12) | −25(12) | −17(16) |

TABLE 7-continued

Anisotropic displacement parameters (Å² × 10³) for k07227.
The anisotropic displacement factor exponent takes the form:
$-2\pi^2[h^2 a^{*2} U^{11} + \ldots + 2 h k a^* b^* U^{12}]$

|  | U¹¹ | U²² | U³³ | U²³ | U¹³ | U¹² |
|---|---|---|---|---|---|---|
| C(8A) | 83(12) | 124(18) | 109(14) | −12(13) | 23(10) | 3(12) |
| C(9A) | 69(10) | 59(11) | 130(16) | 44(11) | 17(11) | 11(9) |
| C(10A) | 47(11) | 180(30) | 220(30) | 30(20) | −10(13) | −16(14) |
| C(11A) | 61(13) | 300(50) | 140(20) | −60(20) | −2(13) | 13(19) |
| C(12A) | 101(14) | 170(20) | 122(17) | 57(17) | −40(13) | −18(15) |
| C(13A) | 49(9) | 122(15) | 59(9) | −5(10) | 12(8) | −2(10) |
| C(14A) | 58(9) | 101(14) | 64(10) | 15(9) | 17(7) | −2(9) |
| C(15A) | 95(14) | 103(16) | 113(15) | 37(13) | 27(11) | 15(12) |
| C(16A) | 85(11) | 105(15) | 68(11) | −27(10) | 17(8) | −17(10) |
| C(17A) | 82(12) | 150(20) | 95(13) | 10(14) | 15(10) | −60(13) |
| C(18A) | 63(9) | 86(12) | 51(8) | 3(8) | 8(7) | −16(9) |
| C(19A) | 59(10) | 122(18) | 49(9) | 5(10) | −2(7) | 2(10) |
| C(20A) | 97(13) | 92(15) | 85(12) | 4(11) | 31(10) | −19(12) |
| C(21A) | 118(18) | 121(19) | 100(15) | 8(13) | 21(13) | −48(16) |
| C(22A) | 95(19) | 190(30) | 102(17) | 11(19) | 0(13) | −26(19) |
| C(23A) | 50(11) | 210(30) | 86(14) | 9(17) | 1(9) | 1(16) |
| C(24A) | 63(12) | 170(20) | 68(11) | −7(13) | −7(8) | 0(13) |
| Si(1B) | 60(3) | 75(3) | 70(3) | 8(3) | 13(2) | 2(2) |
| O(1B) | 71(7) | 106(9) | 83(7) | 14(7) | 14(5) | 3(7) |
| O(2B) | 51(6) | 44(5) | 65(6) | −3(5) | 3(4) | 3(4) |
| O(3B) | 52(6) | 99(9) | 75(7) | 4(6) | 9(5) | 9(6) |
| O(4B) | 69(6) | 60(6) | 71(6) | 11(6) | 24(5) | 5(5) |
| N(1B) | 60(7) | 36(6) | 49(6) | −1(5) | 6(5) | 13(5) |
| N(2B) | 50(7) | 75(9) | 84(9) | 10(8) | 13(6) | 3(7) |
| C(1B) | 57(10) | 48(9) | 61(9) | −17(7) | 6(7) | −4(7) |
| C(2B) | 45(8) | 50(9) | 65(9) | −11(7) | 4(6) | 0(7) |
| C(3B) | 51(8) | 72(10) | 54(8) | −1(8) | 3(6) | 5(8) |
| C(4B) | 47(8) | 62(10) | 73(9) | 25(8) | 17(7) | 8(7) |
| C(5B) | 59(9) | 65(11) | 86(12) | 6(9) | 8(8) | −9(8) |
| C(6B) | 82(11) | 66(11) | 77(11) | 15(9) | 21(8) | 17(9) |
| C(7B) | 84(12) | 87(14) | 123(15) | 34(12) | 28(10) | 36(11) |
| C(8B) | 64(10) | 147(19) | 84(12) | −19(13) | 10(8) | −22(11) |
| C(9B) | 56(9) | 78(13) | 82(11) | 10(9) | 14(8) | −12(9) |
| C(10B) | 113(13) | 64(11) | 77(11) | 23(10) | 11(9) | −7(10) |
| C(11B) | 121(16) | 104(16) | 84(12) | −14(12) | 11(11) | −22(13) |
| C(12B) | 97(13) | 117(17) | 89(12) | 32(13) | 36(10) | 13(12) |
| C(13B) | 48(9) | 85(12) | 75(11) | −3(10) | 18(8) | −9(9) |
| C(14B) | 66(10) | 50(10) | 81(11) | 11(9) | 3(8) | 0(8) |
| C(15B) | 88(13) | 88(17) | 152(19) | 37(15) | −11(12) | 29(11) |
| C(16B) | 62(10) | 112(17) | 116(15) | 14(13) | −1(10) | −1(10) |
| C(17B) | 80(11) | 150(20) | 74(11) | 55(13) | 12(9) | 23(12) |
| C(18B) | 48(8) | 73(11) | 61(9) | −5(8) | 7(6) | 6(7) |
| C(19B) | 34(7) | 105(15) | 56(10) | 14(10) | 8(6) | −16(8) |
| C(20B) | 67(10) | 64(11) | 64(10) | 11(9) | 3(7) | 1(8) |
| C(21B) | 76(12) | 150(20) | 74(13) | 14(16) | 6(10) | −11(12) |
| C(22B) | 67(12) | 120(20) | 120(20) | 35(17) | 13(11) | −20(13) |
| C(23B) | 60(11) | 180(30) | 64(12) | 9(16) | 10(8) | −26(14) |
| C(24B) | 59(10) | 138(17) | 63(11) | −3(12) | 14(8) | −8(10) |

TABLE 8

Hydrogen coordinates (× 10⁴) and isotropic displacement parameters (Å² × 10³) for k07227.

|  | x | y | z | U(eq) |
|---|---|---|---|---|
| H(2A) | 2439 | 3731 | 7164 | 89 |
| H(2A8) | 3677 | 3148 | 6028 | 73 |
| H(3AA) | 3805 | 5507 | 7399 | 73 |
| H(4AA) | 5261 | 4254 | 7594 | 69 |
| H(5AA) | 5126 | 6016 | 6284 | 66 |
| H(6AA) | 6788 | 5688 | 6277 | 86 |
| H(6AB) | 6530 | 6272 | 7171 | 86 |
| H(7AA) | 7391 | 2890 | 8499 | 177 |
| H(7AB) | 6386 | 3254 | 8734 | 177 |
| H(7AC) | 7246 | 3395 | 9455 | 177 |
| H(8AA) | 5915 | 5621 | 8958 | 157 |
| H(8AB) | 6644 | 6535 | 8745 | 157 |
| H(8AC) | 6797 | 5834 | 9638 | 157 |
| H(10A) | 9261 | 6348 | 8041 | 225 |
| H(10B) | 8274 | 6725 | 8319 | 225 |
| H(10C) | 8356 | 6093 | 7402 | 225 |
| H(11A) | 9691 | 4578 | 8109 | 254 |
| H(11B) | 8832 | 4327 | 7410 | 254 |
| H(11C) | 8989 | 3625 | 8301 | 254 |
| H(12A) | 9506 | 5375 | 9499 | 199 |
| H(12B) | 8742 | 4534 | 9768 | 199 |
| H(12C) | 8516 | 5804 | 9723 | 199 |
| H(15A) | 3407 | 1942 | 8750 | 154 |
| H(15B) | 2933 | 1440 | 7847 | 154 |
| H(15C) | 2478 | 1254 | 8764 | 154 |
| H(16A) | 2680 | 3561 | 9449 | 128 |
| H(16B) | 1699 | 2986 | 9469 | 128 |
| H(16C) | 1788 | 4103 | 8942 | 128 |
| H(17A) | 1421 | 2134 | 7206 | 166 |
| H(17B) | 1014 | 3229 | 7588 | 166 |
| H(17C) | 944 | 2115 | 8123 | 166 |
| H(18A) | 3279 | 3371 | 4415 | 80 |
| H(18B) | 2729 | 4426 | 4688 | 80 |
| H(20A) | 2894 | 1576 | 5238 | 108 |
| H(21A) | 1622 | 461 | 5349 | 135 |
| H(22A) | 261 | 1165 | 5684 | 154 |
| H(23A) | −81 | 3040 | 5417 | 140 |
| H(24A) | 1185 | 4248 | 5190 | 122 |
| H(2B) | 7412 | 1227 | 7705 | 83 |
| H(2BB) | 6146 | 681 | 6365 | 64 |
| H(3BA) | 7647 | 2950 | 6413 | 71 |
| H(4BA) | 7677 | 1752 | 4955 | 72 |
| H(5BA) | 6321 | 3505 | 5026 | 84 |
| H(6BA) | 7190 | 3796 | 3799 | 89 |
| H(6BB) | 6209 | 3326 | 3435 | 89 |
| H(7BA) | 8930 | 851 | 3678 | 146 |
| H(7BB) | 9322 | 938 | 2721 | 146 |
| H(7BC) | 8336 | 402 | 2817 | 146 |
| H(8BA) | 8613 | 4161 | 3276 | 147 |
| H(8BB) | 9522 | 3478 | 3134 | 147 |
| H(8BC) | 9023 | 3346 | 4033 | 147 |
| H(10D) | 7339 | 3913 | 916 | 127 |
| H(10E) | 7981 | 4300 | 1769 | 127 |
| H(10F) | 6967 | 3855 | 1883 | 127 |
| H(11D) | 7007 | 1971 | 649 | 154 |
| H(11E) | 6613 | 1863 | 1604 | 154 |
| H(11F) | 7412 | 1069 | 1336 | 154 |
| H(12D) | 8576 | 2679 | 512 | 149 |
| H(12E) | 9009 | 1805 | 1211 | 149 |
| H(12F) | 9206 | 3070 | 1372 | 149 |
| H(15D) | 8712 | −718 | 6882 | 166 |
| H(15E) | 7802 | −1087 | 7323 | 166 |
| H(15F) | 8792 | −1398 | 7788 | 166 |
| H(16D) | 9719 | 649 | 7571 | 146 |
| H(16E) | 9792 | 36 | 8509 | 146 |
| H(16F) | 9437 | 1264 | 8442 | 146 |
| H(17D) | 7413 | −280 | 8715 | 154 |
| H(17E) | 8026 | 694 | 9140 | 154 |
| H(17F) | 8414 | −521 | 9189 | 154 |
| H(18C) | 4814 | 1945 | 7173 | 73 |
| H(18D) | 4502 | 892 | 6609 | 73 |
| H(20B) | 5304 | −894 | 7046 | 78 |
| H(21B) | 5548 | −2016 | 8234 | 121 |
| H(22B) | 5615 | −1446 | 9672 | 126 |
| H(23B) | 5475 | 386 | 9970 | 120 |
| H(24B) | 5229 | 1630 | 8761 | 104 |

Although preferred embodiments of the invention have been described herein, it will be understood by those skilled in the art that variations may be made thereto without departing from the spirit of the invention or the scope of the appended claims. All references mentioned herein are incorporated by reference in their entirety.

REFERENCES (1) Drahl, S. Chem. Eng. News 2009, 87, 31.
(2) a) Shao, Y.; Lu, W.; Kent, S. B. H. Tetrahedron. Lett. 1998, 39, 3911. b) Tam, J. P.; Lu, Y.-A.; Yu, Q. J. Am. Chem.

Soc. 1999, 121, 4316. c) Bernal, F.; Tyler, A. F.; Korsmeyer, S. J.; Walensky, L. D.; Verdine, G. L. J. Am. Chem. Soc. 2007, 129, 2456. d) Horne, W. S.; Stout, C. D.; Ghadiri, M. R. J. Am. Chem. Soc. 2003, 125, 9372. e) Blackwell, H. E.; Sadowsky, J. D.; Howard, R. J.; Sampson; J. N., Chao; J. A., Steinmetz, W. E.; O'Leary, D. J.; Grubbs, R. H. J. Org. Chem. 2001, 66, 5291. f) Kirshenbaum, K.; Arora, P. S. Nat. Chem. Bio. 2008, 4, 527. g) Hebach, C.; Kazmaier, U. Chem. Comm. 2003, 9, 596. h) Reid, R. C.; Kelso, M. J.; Scanlon, M. J.; Fairlie, D. P. J. Am. Chem. Soc. 2002, 124, 5673. i) Al-Obeidi, F.; de Castrucci, A. M. L.; Hadley, M. E.; Hruby, V. J. J. Med. Chem. 1989, 32, 2555. j) Geyer, A.; Mueller, G.; Kessler, H. J. Am. Chem. Soc. 1994, 116, 7735.

(3) Schmuck, C.; Wienand, W. J. Am. Chem. Soc. 2003, 125, 452.

(4) A. F. Spatola and P. Romanovskis, in Combinatorial Peptide and Nonpeptide Libraries; Jung, G., Ed.; VCH: Weinheim, 1996; p 328.

(5) H. C. Gilon, C. Mang, E. Lohof, A. Friedler, H. Kessler, in Synthesis of Peptides and Peptidomimetics; Goodman, M., Ed.; Thieme: Stuttgart, 2004; pp 461.

(6) Zimmer, S.; Hoffmann, E.; Jung, G.; Kessler, H. Liebigs. Ann. Chem. 1993, 497.

(7) Schmidt, U.; Langner, J. J. Pept. Res. 1997, 49, 67.

(8) a) Hili, R.; Yudin, A. K. J. Am. Chem. Soc. 2009, 131, 16404. b) Baktharaman, S.; Hili, R.; Yudin, A. K. Aldrichimica Acta 2008, 41, 109. c) Hili, R.; Baktharam, S.; Yudin, A. K. Eur. J. Org. Chem. 2008, 5201. d) Hili, R.; Yudin, A. K. Angew. Chem. Int. Ed. 2008, 47, 4188. e) Yudin, A. K.; Hili, R. Chem. Eur. J. 2007, 13, 6538. f) Hili, R.; Yudin, A. K. J. Am. Chem. Soc. 2006, 128, 14772.

(9) Roccatano, D., Colombo, G., Fioroni, M., Mark, A. E. Proc. Nat. Acad. Sci. 2002, 99, 12179.

(10) a) Domling, A.; Ugi, I. Angew. Chem. Int. Ed. 1997, 39, 3168. b) Domling, A.; Ugi, I. Angew. Chem. Int. Ed. 2000, 39, 3169. c) Thompson, M. J.; Chen, B. J. Org. Chem. 2009, 74, 7084.

(11) Demharter, A.; Hörl, W.; Herdtweck, E.; Ugi, I. Angew. Chem. Int. Ed. 1996, 36, 173.

(12) For a recent example describing consecutive Ugi reactions to access glycine-based peptoid structures from formaldehyde, see: Vercillo, O. E., Andrade, C. K. Z., Wessjohann, L. A. Org. Lett. 2008, 10, 205.

(13) A. Failli, H. Immer, M. Gotz, Can. J. Chem. 1979, 57, 3257.

(14) Galonio, D. P.; Ide, N. D.; van der Donk, W. A.; Gin, D. Y. J. Am. Chem. Chem. 2005, 127, 7359.

The invention claimed is:

1. A process to produce a cyclic molecule comprising reacting an amino acid molecule, having an amino terminus and a carboxyl terminus, with an isocyanide and a compound having formula (Ia) and/or (Ib):

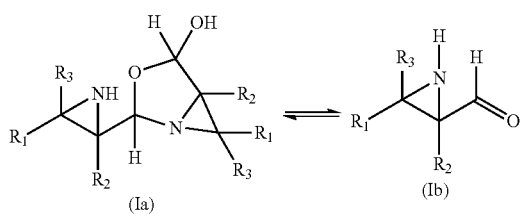

wherein:
$R_1$, $R_2$, $R_3$, are independently selected from H; lower alkyl; alkenyl; heterocycle; cyckoalkyl; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -lower alkyl-aryl, or —NR$_a$R$_b$, where $R_a$ and $R_b$ are independently selected from H, lower alkyl, aryl or -lower alkyl-aryl; —C(O)R$_c$, wherein R$_c$ is selected from lower alkyl, aryl or -lower alkyl-aryl; or -lower alkyl-OR$_d$, wherein R$_d$ is a suitable protecting group or OH group; all of which are optionally substituted at one or more substitutable positions with one or more suitable substituents; and
the aldehyde component thereof may optionally be in its bisulfite adduct form; and
the amino acid molecule is an amino acid, a linear peptide or a salt of the foregoing, provided that if the amino acid molecule is a linear peptide, the compound having formula (Ia) and/or (Ib) comprises an aziridine chiral center proximal to the aldehyde with matching stereochemistry to the carbon atom proximal to the amino terminus of the peptide;
wherein the cyclic molecule is of formula (II):

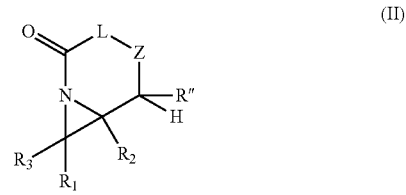

wherein Z is an amino terminus of an amino acid;
—C=O—C is the carboxy terminus of an amino acid;
L, along with Z and —C=O— is an amino acid or peptide; and
R″ is an optionally substituted amide.

2. The process of claim 1, wherein if L, along with Z and —C=O— is an amino acid then the amino terminus is a primary amino group or a secondary amino group but when L, along with Z and —C=O— is a linear peptide, then the amino terminus is a secondary amino group.

3. The process of claim 1, wherein any one of $R_1$ -$R_3$ is H.

4. The process of claim 1, wherein each of $R_1$ -$R_3$ is H.

5. The process of claim 1, wherein $R_2$ and $R_3$ are both H.

6. The process of claim 5, wherein $R_1$ is CH$_2$OTBDMS or CH$_2^i$Pr.

7. The process of claim 1 wherein the amino acid molecule is a linear peptide.

8. The process of claim 7, wherein the amino terminus amino acid of the linear peptide is selected from the group consisting of proline and an amino acid with an amino group substituted with NHBn, NHCH$_2$CH$_2$SO$_2$Ph or NHCH$_2$CH$_2$CN.

9. The process of claim 1 wherein the amino acid molecule is a D or L amino acid selected from the group consisting of: alanine, arginine, asparagine, aspartic acid, cysteine, glutamic acid, glutamine, glycine, histidine, isoleucine, leucine, lysine, methionine, phenylalanine, proline, selenocysteine, serine, tyrosine, threonine, tryptophan and valine.

10. The process of claim 1 wherein the amino acid molecule is an alpha-amino acid.

11. The process of claim 1 wherein the amino acid molecule is a beta-amino acid.

12. The process of claim 1 wherein the amino acid molecule is a gamma-amino acid.

13. The process of claim 1 wherein the isocyanide is selected from the group consisting of: (S)-(−)-α-Methylbenzyl isocyanide; 1,1,3,3,-Tetramethylbutyl isocyanide; 1-Pentyl isocyanide; 2,6-Dimethylphenyl isocyanide; 2-Morpholinoethyl isocyanide; 2-Naphthyl isocyanide; 2-Pentyl isocyanide; 4-Methoxyphenyl isocyanide; Benzyl isocyanide; Cutyl isocyanide; Cyclohexyl isocyanide; Isopropyl isocyanide; p-Toluenesulfonylmethyl isocyanide; Phenyl isocyanide dichloride; tert-Butyl isocyanide;(Trimethylsilyl) methyl isocyanide; 1H-Benzotriazol-1-ylmethyl isocyanide; 2-Chloro-6-methylphenyl isocyanide; Di-tert-butyl 2-isocyanosuccinate; tert-Butyl 2-isocyano-3-methylbutyrate; tert-Butyl 2-isocyano-3-phenylpropionate; tert-Butyl 2-isocyanopropionate; and tert-butyl 3-isocyanopropionate.

14. The process of claim 1 wherein the isocyanide is tert-Butyl isocyanide.

15. The process of claim 1 wherein the process is conducted in a non-nucleophilic reaction medium.

16. The process of claim 15 wherein the non-nucleophilic reaction medium is trifluoroethanol.

17. The process of claim 15 wherein the non-nucleophilic reaction medium is HFIP mixed with water.

18. The process of claim 1, wherein amino acid molecule is an amino acid and the process is conducted in water.

19. The process of claim 1 wherein the peptide is between 2 and 30 amino acids in length.

20. A cyclic molecule of formula (II):

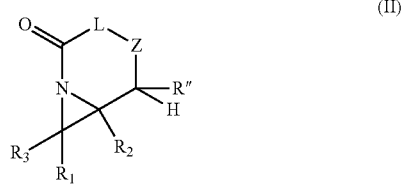

(II)

wherein,
$R_1$, $R_2$ and $R_3$ are independently selected from H; lower alkyl; aryl; heteroaryl; alkenyl; heterocycle; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -loweralkyl-aryl, or —NR$_a$R$_b$, where R$_a$ and R$_b$ are independently selected from H, lower alkyl, aryl or -loweralkyl-aryl; —C(O)R$_c$, wherein R$_c$ is selected from lower alkyl, aryl or -lower alkyl-aryl; or -lower alkyl-OR$_d$, wherein R$_d$ is a suitable protecting group or OH group; all of which are optionally substituted at one or more substitutable positions with one or more suitable substituents,
Z is an amino terminus of an amino acid;
—C=O— is the carboxy terminus of an amino acid;
L, along with Z and —C=O— is an amino acid or peptide and R″ is an optionally substituted amide.

21. The cyclic molecule of claim 20, wherein if L, along with Z and —C=O—is an amino acid then the amino terminus is a primary amino group or a secondary amino group but when L, along with Z and —C=O— is a linear peptide, then the amino terminus is a secondary amino group.

22. The process of claim 1, wherein the concentration of the amino acid molecule is at least at 0.002M.

23. The process of claim 1, wherein the concentration of the amino acid molecule is between 0.002M to 0.2M.

24. The process of claim 1, wherein the concentration of the amino acid molecule is at least 0.1M.

25. The process of claim 1, wherein the concentration of the amino acid molecule is around 0.2M.

26. The cyclic molecule of claim 20, wherein the molecule is a compound having the following formula:

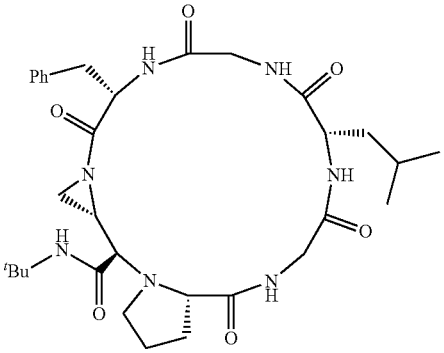

wherein Ph is a phenyl group and $^t$Bu is a tent-butyl group.

27. The cyclic molecule of claim 20, wherein any one of $R_1$ -$R_3$ is H.

28. The cyclic molecule of claim 20, wherein $R_1$ -$R_3$ are H.

29. The cyclic molecule of claim 27, wherein $R_2$ and $R_3$ are H.

30. The cyclic molecule of claim 29, wherein $R_1$ is CH$_2$OTBDMS or CH$_2^i$Pr.

31. The cyclic molecule of claim 20, wherein L, along with Z and —C=O— is a linear peptide.

32. The cyclic molecule of claim 31, wherein the amino terminus amino acid of the linear peptide is selected from the group consisting of proline and an amino acid with an amino group substituted with NHBn, NHCH$_2$CH$_2$SO$_2$Ph or NHCH$_2$CH$_2$CN.

33. The cyclic molecule of claim 20, wherein L, along with Z and —C=O— is a D- or L- amino acid selected from the group consisting of: alanine, arginine, asparagine, aspartic acid, cysteine, glutamic acid, glutamine, glycine, histidine, isoleucine, leucine, lysine, methionine, phenylalanine, proline, selenocysteine, serine, tyrosine, threonine, tryptophan and valine.

34. The cyclic molecule of claim 20 wherein L, along with Z and —C=O— is an alpha-amino acid.

35. The cyclic molecule of claim 20, wherein L, along with Z and —C=O— is a beta-amino acid.

36. The cyclic molecule of claim 20 wherein L, along with Z and —C=O— is a gamma-amino acid.

37. The cyclic molecule of claim 20, wherein R″ is tert-Butyl amide.

38. The cyclic molecule of claim 20, wherein —Z-L—C=O— is a peptide consisting of 2 amino acids.

39. The cyclic molecule of claim 20, wherein —Z-L—C=O— is a peptide consisting of 3 amino acids.

40. The cyclic molecule of claim 22, wherein —Z-L—C=O— is a peptide consisting of 4 amino acids.

41. The cyclic molecule of claim 20, wherein —Z-L—C=O— is a peptide consisting of 5 amino acids.

42. The cyclic molecule of claim 20, wherein —Z-L—C=O— is a peptide consisting of 6 amino acids.

43. The cyclic molecule of claim 20, wherein —Z-L—C=O— is a peptide consisting of 7 amino acids.

44. The cyclic molecule of claim 22, wherein —Z-L—C=O— is a peptide consisting of 8 amino acids.

45. The cyclic molecule of claim 22, wherein —Z-L—C=O— is a peptide consisting of 9 amino acids.

46. A process for producing a cyclic molecule of formula (III)

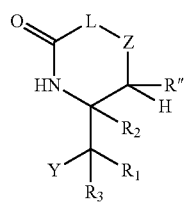
(III)

comprising reacting an amino acid molecule, having an amino terminus and a carboxyl terminus, with an isocyanide and a compound of formula (Ia) and/or (Ib)

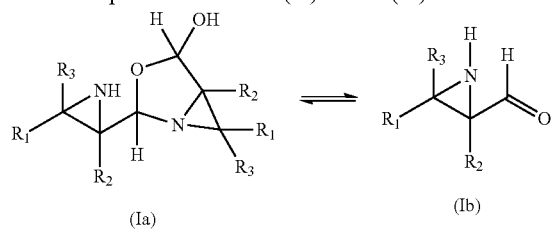

thereby forming a cyclic molecule of formula II :

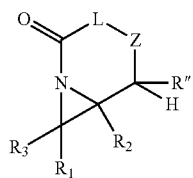
(II)

and subsequently reacting the cyclic molecule of formula (II) with a compound of formula Y—H under conditions effective to form the cyclic molecule of formula (III);

wherein $R_1$, $R_2$, and $R_3$ are independently selected from H; lower alkyl; alkenyl; heterocycle; cyckoalkyl; esters of the formula —C(O)OR* wherein R* is selected from alkyl and aryl; amides of the formula —C(O)NRR*, wherein R and R* are independently selected from alkyl and aryl; —CH$_2$C(O)R, wherein R is selected from —OH, lower alkyl, aryl, -lower alkyl-aryl, or —NR$_a$R$_b$, where R$_a$ and R$_b$ are independently selected from H, lower alkyl, aryl or -lower alkyl-aryl; —C(O)R$_c$, wherein R$_c$, is selected from lower alkyl, aryl or -lower alkyl-aryl; or -lower alkyl —OR$_d$, wherein R$_d$ is a suitable protecting group or OH group; all of which are optionally substituted at one or more substitutable positions with one or more suitable substituents; and the aldehyde component thereof may optionally be in its bisulfite adduct form; and the amino acid molecule is an amino acid, a linear peptide or a salt of the foregoing, provided that if the amino acid molecule is a linear peptide, the compound having formula (Ia) and/or (Ib) comprises an aziridine chiral center proximal to the aldehyde with matching stereochemistry to the carbon atom proximal to the amino terminus of the peptide;

Z is an amino terminus of an amino acid;

—C=O— is the carboxy terminus of an amino acid;

L, along with Z and —C=O— is an amino acid or peptide

R″ is an optionally substituted amide; and

Y—H comprises a nucleophilic moiety.

47. The process according to claim 46, wherein Y is a fluorescent moiety.

* * * * *